(12) United States Patent
Ikemoto et al.

(10) Patent No.: US 8,822,694 B2
(45) Date of Patent: Sep. 2, 2014

(54) PROCESS FOR PRODUCING PYRROLE COMPOUND

(75) Inventors: Tomomi Ikemoto, Osaka (JP); Misayo Sera, Osaka (JP); Naohiro Fukuda, Osaka (JP)

(73) Assignee: Takeda Pharmaceutical Company Limited, Osaka-shi (JP)

(*) Notice: Subject to any disclaimer, the term of this patent is extended or adjusted under 35 U.S.C. 154(b) by 67 days.

(21) Appl. No.: 13/203,441

(22) PCT Filed: Feb. 24, 2010

(86) PCT No.: PCT/JP2010/052874
§ 371 (c)(1),
(2), (4) Date: Aug. 25, 2011

(87) PCT Pub. No.: WO2010/098351
PCT Pub. Date: Sep. 2, 2010

(65) Prior Publication Data
US 2011/0306769 A1 Dec. 15, 2011

(30) Foreign Application Priority Data
Feb. 25, 2009 (JP) .................. 2009-042975

(51) Int. Cl.
*C07D 401/12* (2006.01)

(52) U.S. Cl.
USPC ........................................ 546/278.4

(58) Field of Classification Search
USPC ........................................ 546/278.4
See application file for complete search history.

(56) References Cited

U.S. PATENT DOCUMENTS

| | | | |
|---|---|---|---|
| 4,546,099 A | 10/1985 | Nyfeler | |
| 4,904,687 A | 2/1990 | Wollweber et al. | |
| 5,010,098 A | 4/1991 | Brown et al. | |
| 5,101,042 A | 3/1992 | Lowen | |
| 5,122,615 A | 6/1992 | Lowen | |
| 5,252,746 A | 10/1993 | Lowen | |
| 5,359,090 A | 10/1994 | Doehner et al. | |
| 5,563,279 A | 10/1996 | Kameswaran | |
| 7,498,337 B2 * | 3/2009 | Kajino et al. ............. | 514/277 |
| 2008/0090882 A1 | 4/2008 | Dorsch et al. | |
| 2008/0139639 A1 | 6/2008 | Kajino et al. | |
| 2011/0028476 A1 | 2/2011 | Kajino et al. | |

FOREIGN PATENT DOCUMENTS

| | | | |
|---|---|---|---|
| EP | 0358047 A2 | 3/1990 | |
| EP | 0491136 A2 | 6/1992 | |
| JP | 2-167203 A | 6/1990 | |
| JP | 6-9554 A | 1/1994 | |
| JP | 10-324687 A | 12/1998 | |
| WO | WO-02/30358 A2 | 4/2002 | |
| WO | WO-2004/103968 A1 | 12/2004 | |
| WO | WO-2005/040110 A1 | 5/2005 | |
| WO | WO-2006/036024 A1 | 4/2006 | |
| WO | WO-2006/064944 A1 | 6/2006 | |
| WO | WO-2007/026916 A1 | 3/2007 | |

OTHER PUBLICATIONS

Dorwald, Side Reactions in Organic Synthesis, 2005, Wiley: VCH Weinheim Preface, pp. 1-15 & Chapter 8, pp. 279-308.*
Gangjee, et al., "Novel 2,4-Diamino-5-Substituted-pyrrolo [2,3-d]pyrimidines as Classical and Nonclassical Antifolate Inhibitor of Dihydrofolate Reductases", J. Med. Chem., vol. 38, p. 2158-2165 (1995).
Krawczyk, S. et al, "Synthesis and Antiproliferative and Antiviral Activity of 2'-deoxy-2'-fluoroarabinofuranosyl Analogs of the Nucleoside Antibiotics Toyocamycin and Sangivamycin", J. Med. Chem. vol. 38, p. 4106-4114 (1995).
Khalifa F. et al, "Benzoin in Heterocyclic Synthesis: Synthesis and Reactions of 4-Cyano-2, 3-Diphenyl-2H-Pyrrol-5-Thione" Tetrahedron vol. 47, No. 38, pp. 8243-8250 (1991).
Moiseeva, I.V., et al. "Synthesis of BIS(3-Cyano-2-Pyrrolyl) Disulfides" Letters to the Editor, Translated from Khimiya Geterotsiklicheskikh Soedinenii, No. 2, p. 227, Feb. 1992.
Balow, G., et al., "Positioning of Functionalities in a Heteroduplex Major Groove: Synthesis of 7-Deaza-2-Amino-2'-deoxyadenosines", Nucleosides & Nucleotides, 16(7-9), p. 941-944 (1997).
Barnett G.H. et al., Pyrrole Chemistry. XXI. Synthetic Approaches to Cyanopyrroles, Canadian Journal Of Chemistry, vol. 58, pp. 409-411 (1980).

(Continued)

*Primary Examiner* — Patricia L Morris
(74) *Attorney, Agent, or Firm* — Edwards Wildman Palmer LLP; David G. Conlin; Lisa Swiszcz Hazzard

(57) ABSTRACT

The present invention provides a production method of a sulfonylpyrrole compound useful as a pharmaceutical product, a production method of an intermediate used for the method, and a novel intermediate. The present invention relates to a method of producing sulfonylpyrrole compound (VIII), which includes reducing compound (III) and hydrolyzing the reduced product to give compound (IV), subjecting compound (IV) to a sulfonylation reaction to give compound (VI), and subjecting compound (VI) to an amination reaction.

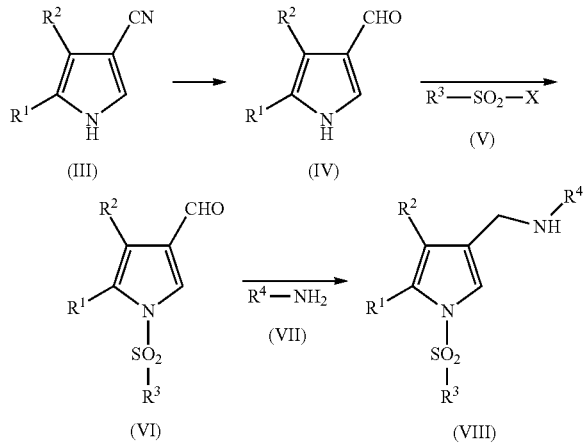

2 Claims, No Drawings

(56) References Cited

OTHER PUBLICATIONS

Tverdokhlebov A.V. et al., A Novel Approach to Pyrrolo [2,1 -*b*] [1,3] benzothiazines, Synthesis, No. 17, pp. 2701-2706 (2008).

Nasakin O.E. et al., Reactivity of β, β-γ, γ-Tetracyanoalkanones, β, β-Dicyanoalkanones, and 5-Amino-4-cyano-2,3-dihydrofurans, Russian Journal Of General Chemistry, vol. 69, No. 2, pp. 291-300 (1999).

International Search Reporting for PCT/JP2010/052874 (Mar. 30, 2010).

Koza "Organic Synthesis III, Aldehyde/Ketone/Quinone" in *Courses in Experimental Chemistry, 4th Edition*, vol. 21, pp. 90-92, Feb. 5, 1991, edited by the Chemical Society of Japan, Maruzen Co. Ltd. (with English Translation).

Supplemental European Search Report mailed Jul. 9, 2014, in corresponding European Patent Application No. 14152159.1.

Collins et al., "Novel pyrrole-containing progesterone receptor modulators", Bioorganic & Medicinal Chemistry Letters, vol. 14, pp. 2185-2189 (2004).

Pinna et al., "Synthesis and dopamine $D_2$-like receptor binding affinity of substituted 5-phenyl-pyrrole-3-carboxamides", II Farmaco, vol. 54, pp. 542-550 (1999).

\* cited by examiner

PROCESS FOR PRODUCING PYRROLE COMPOUND

CROSS-REFERENCE TO RELATED APPLICATIONS

This application is the national phase application pursuant to 35 U.S.C. §371 of International Application No. PCT/JP2010/052874, filed Feb. 24, 2010, which claims the benefit of priority of Japanese Patent No. 2009-042975, filed Feb. 25, 2009. These applications are hereby incorporated herein by reference in their entireties.

TECHNICAL FIELD

The present invention relates to a production method of a pyrrole compound useful as a pharmaceutical product, particularly an acid secretion inhibitor, a production method of an intermediate used for this method, a novel intermediate and the like.

BACKGROUND OF THE INVENTION

A pyrrole compound having a substituted sulfonyl group at the 1-position (hereinafter to be referred to as a sulfonylpyrrole compound) is useful as an acid secretion inhibitor (proton pump inhibitor), a therapeutic drug for a neoplastic disease or an autoimmune disease (patent documents 1-3).

For example, patent document 2 describes, as a compound having an acid secretion suppressive activity, a compound represented by the formula:

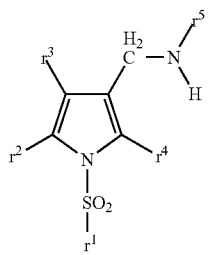

wherein $r^1$ is a monocyclic nitrogen-containing heterocyclic group optionally condensed with a benzene ring or a heterocycle, wherein the monocyclic nitrogen-containing heterocyclic group optionally condensed with a benzene ring or a heterocycle optionally has substituent(s), $r^2$ is an optionally substituted $C_{6-14}$ aryl group, an optionally substituted thienyl group or an optionally substituted pyridyl group, $r^3$ and $r^4$ are each a hydrogen atom, or one of $r^3$ and $r^4$ is a hydrogen atom and the other is an optionally substituted lower alkyl group, an acyl group, a halogen atom, a cyano group or a nitro group, and $r^5$ is an alkyl group, or a salt thereof.

Patent document 2 describes, as a production method of a sulfonylpyrrole compound, the following method using a pyrrole-3-carboxylate:

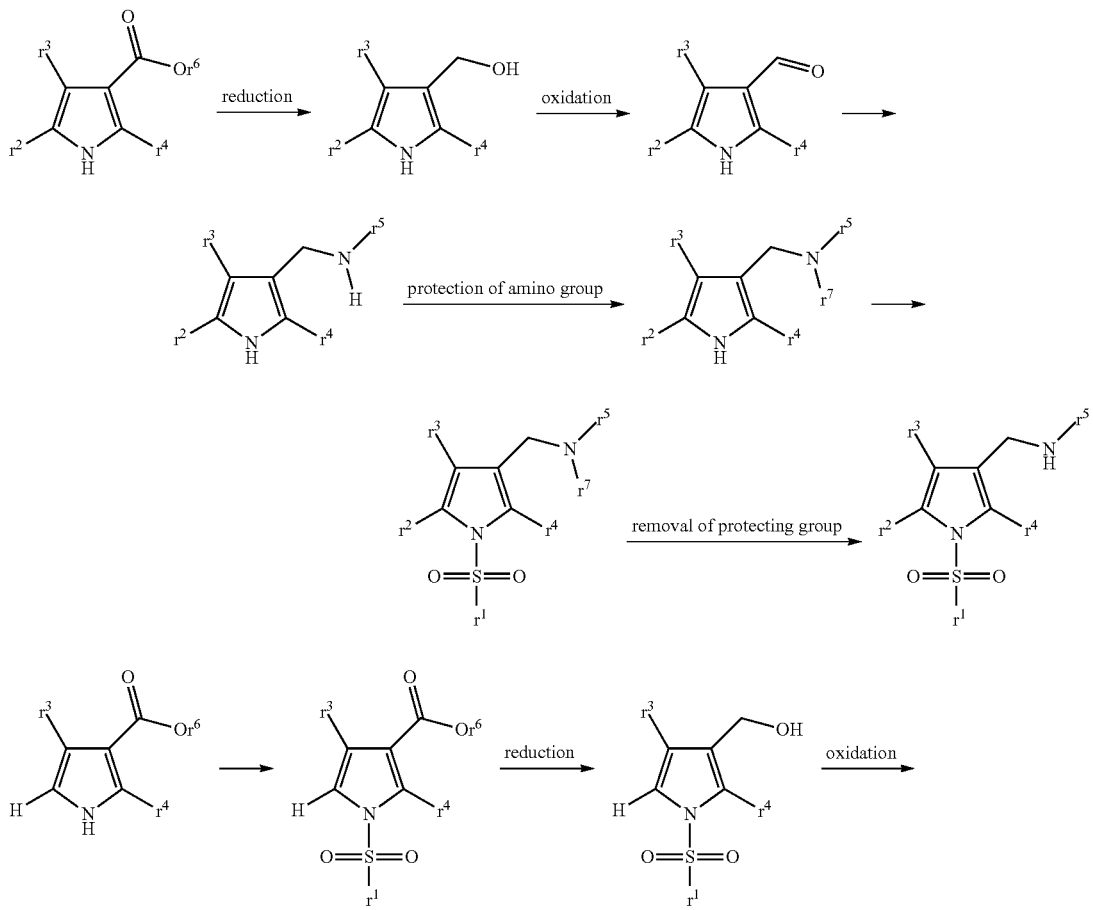

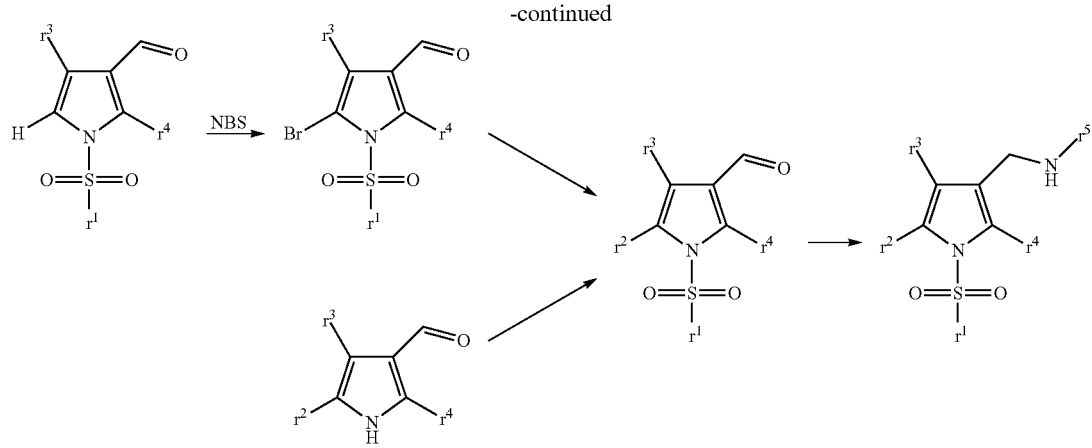

Patent document 3 describes the following production method of a sulfonylpyrrole compound:

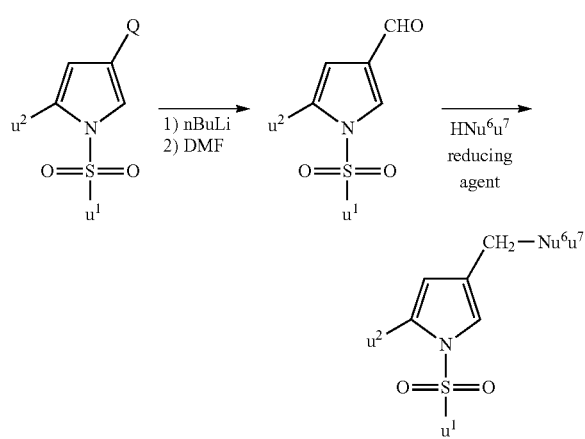

wherein Q is chlorine, bromine or iodine.

On the other hand, the following method is known as a production method of a 2-halogeno-3-cyanopyrrole compound.

Patent document 4

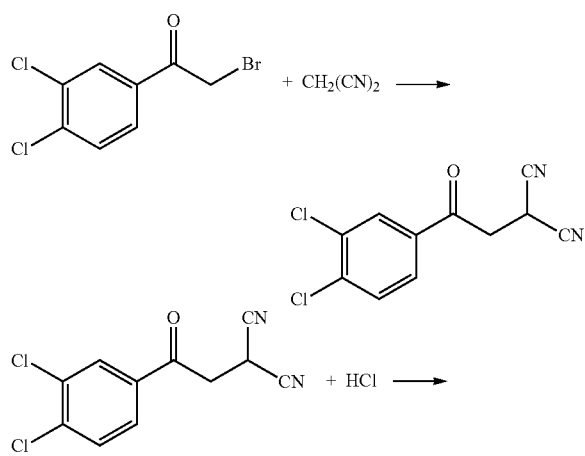

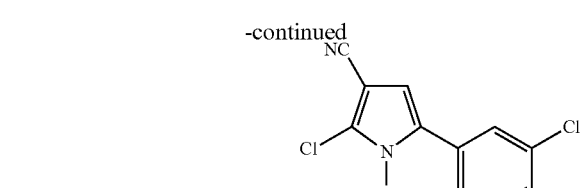

As a method for producing a 3-cyanopyrrole compound from a 2-halogeno-3-cyanopyrrole compound, the following methods are known.

Non-patent document 1, Non-patent document 2

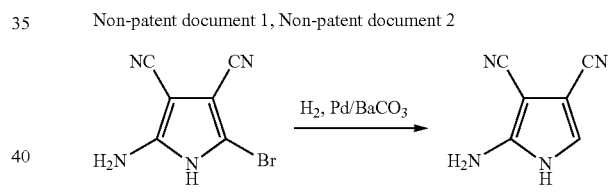

Non-patent document 3

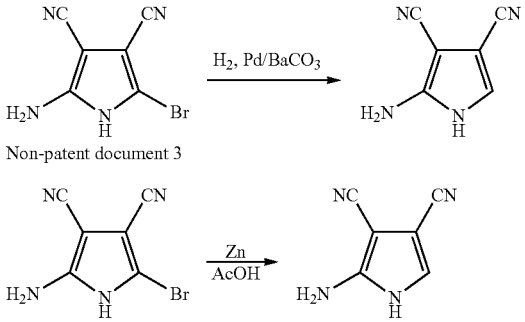

As a method for producing a 3-formylpyrrole compound from a 3-cyanopyrrole compound, the following methods are known.

Non-patent document, Non-patent document 2

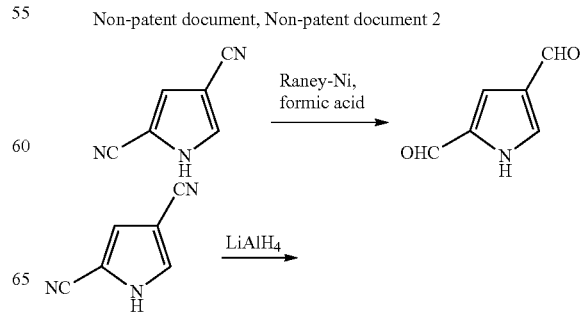

-continued

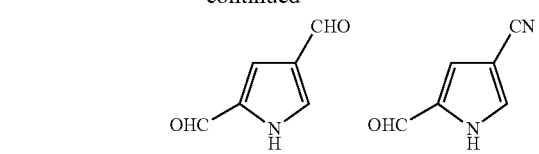

Patent document 5

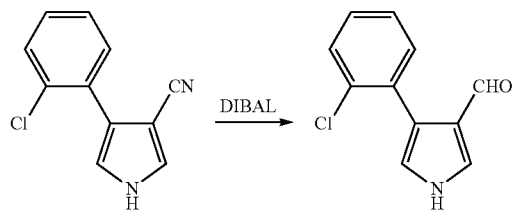

In addition, as a 3-cyanopyrrole compound, the following compounds are known.

Patent document 6

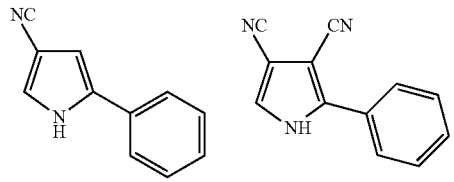

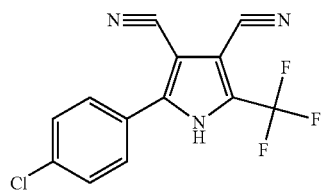

Patent document 7

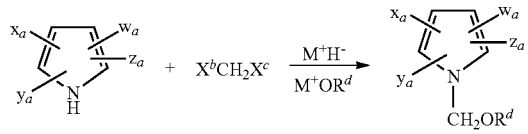

Patent document 8

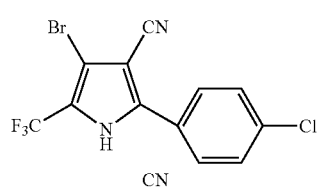

Patent document 9

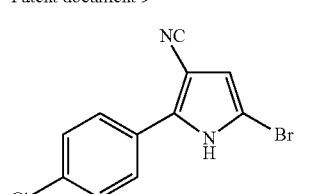

Patent document 10

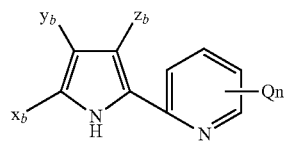

TABLE 1

| $w_a$ | $x_a$ | $y_a$ | $z_a$ | $R^d$ |
|---|---|---|---|---|
| 3-CN | 4-Cl | 5-Cl | 2-(p-CF$_3$O—C$_6$H$_5$) | C$_2$H$_5$ |
| 4-NO$_2$ | 2-Br | 3-Br | 5-(p-Cl—C$_6$H$_5$) | C$_2$H$_5$ |
| 4-NO$_2$ | 2-Cl | 3-Cl | 5-(3,4-diCl—C$_6$H$_5$) | C$_2$H$_5$ |
| 4-NO$_2$ | 2-Cl | 3-Cl | 5-(p-Br—C$_6$H$_5$) | C$_2$H$_5$ |
| 3-CN | 4-Cl | 5-Cl | 2-(p-CF$_3$—C$_6$H$_5$) | C$_2$H$_5$ |
| 3-CN | 4-Cl | 5-Cl | 2-(3,4-diCl—C$_6$H$_5$) | C$_2$H$_5$ |
| 3-CN | 4-Cl | 5-Cl | 2-(p-Cl—C$_6$H$_5$) | C$_2$H$_5$ |
| 4-NO$_2$ | 2-(p-Cl—C$_6$H$_5$) | 5-CF$_3$ | 2-(p-Cl—C$_6$H$_5$) | C$_2$H$_5$ |
| 3-CN | 4-Br | 5-Br | 2-Br | C$_2$H$_5$ |
| 3-CN | 4-Br | 5-CF$_3$ | 2-(p-Cl—C$_6$H$_5$) | C$_2$H$_5$ |
| 3-CN | 4-Cl | 5-CF$_3$ | 2-(p-Cl—C$_6$H$_5$) | C$_2$H$_5$ |
| 4-NO$_2$ | 3-(p-Cl—C$_6$H$_5$) | 5-CF$_3$ | 2-(p-Cl—C$_6$H$_5$) | C$_2$H$_5$ |
| 3-NO$_2$ | 4-(3,4-diCl—C$_6$H$_5$) | 5-CF$_3$ | 2-(p-Cl—C$_6$H$_5$) | C$_2$H$_5$ |
| 4-NO$_2$ | 3-(m-CN—C$_6$H$_5$) | 2-CF$_3$ | 5-(p-Cl—C$_6$H$_5$) | C$_2$H$_5$ |
| 3-CN | 4-Br | 5-Br | 2-(p-CF$_3$—C$_6$H$_5$) | C$_2$H$_5$ |
| 3-CN | 2-Cl | 4-Cl | 5-(3,4-diCl—C$_6$H$_5$) | C$_2$H$_5$ |
| 3-CN | 2-Cl | 4-Br | 5-(p-Br—C$_6$H$_5$) | C$_2$H$_5$ |

TABLE 2

| Compound No | Qn | $x_b$ | $y_b$ | $z_b$ |
|---|---|---|---|---|
| 2-5 | 3-Cl | H | CN | H |
| 2-6 | 3-Cl | CH$_3$ | CN | H |
| 2-7 | 3-Cl | Cl | CN | H |
| 2-8 | 3-Cl | Br | CN | H |
| 2-31 | 3-Cl | H | CN | CH$_3$ |
| 2-32 | 3-Cl | H | CN | CHO |
| 2-57 | 3-Me | H | CN | H |
| 2-58 | 3-Me | CH$_3$ | CN | H |
| 2-59 | 3-Me | Cl | CN | H |
| 2-60 | 3-Me | Br | CN | H |
| 2-72 | 3-Me | H | CN | CH$_3$ |
| 2-73 | 3-Me | H | CN | CHO |
| 2-92 | 3-cyclopropyl | H | CN | H |
| 2-93 | 3-cyclopropyl | CH$_3$ | CN | H |
| 2-94 | 3-cyclopropyl | Cl | CN | H |
| 2-95 | 3-cyclopropyl | Br | CN | H |
| 2-108 | 3-cyclopropyl | H | CN | CH$_3$ |
| 2-109 | 3-cyclopropyl | H | CN | CHO |

TABLE 3

| Compound No | Qn | $x_b$ | $y_b$ | $z_b$ |
|---|---|---|---|---|
| 2-128 | 5-cyclopropyl | H | CN | H |
| 2-129 | 5-cyclopropyl | CH$_3$ | CN | H |
| 2-130 | 5-cyclopropyl | Cl | CN | H |
| 2-131 | 5-cyclopropyl | Br | CN | H |
| 2-145 | 5-cyclopropyl | H | CN | CH$_3$ |
| 2-146 | 5-cyclopropyl | H | CN | CHO |
| 2-157 | 5-Et | H | CN | H |
| 2-158 | 5-Et | CH$_3$ | CN | H |
| 2-159 | 5-Et | Cl | CN | H |
| 2-160 | 5-Et | Br | CN | H |
| 2-175 | 5-Et | H | CN | CH$_3$ |
| 2-176 | 5-Et | H | CN | CHO |
| 2-195 | 3-C≡CH | H | CN | H |

TABLE 3-continued

| Compound No | Qn | $x_b$ | $y_b$ | $z_b$ |
| --- | --- | --- | --- | --- |
| 2-196 | 3-C≡CH | CH₃ | CN | H |
| 2-197 | 3-C≡CH | Cl | CN | H |
| 2-198 | 3-C≡CH | Br | CN | H |
| 2-212 | 3-C≡CH | H | CN | CH₃ |
| 2-213 | 3-C≡CH | H | CN | CHO |

In addition, as a 2-mercaptopyrrole derivative, the following compounds are known.

For example, non-patent document 5 describes 2-mercaptopyrrole derivative (A) having a cyano group at the 3-position:

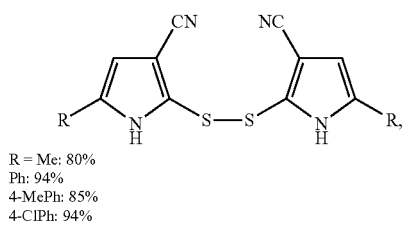

R = Me: 80%
Ph: 94%
4-MePh: 85%
4-ClPh: 94% non-patent document 6 describes 2-mercaptopyrrole derivative (B) having a cyano group at the 3-position:

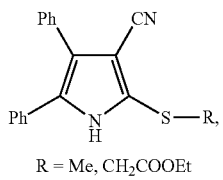

R = Me, CH₂COOEt patent document 11 describes 2-mercaptopyrrole derivative (C) having a cyano group at the 3-position:

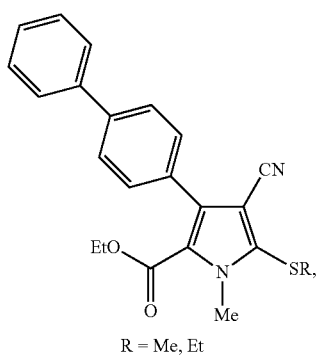

R = Me, Et and patent document 12 describes 2-mercaptopyrrole derivative (D) having a cyano group at the 3-position:

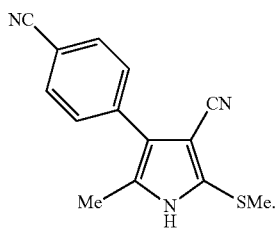

As a synthesis method of these 2-mercaptopyrrole derivatives having a cyano group at the 3-position, non-patent document 5 describes, as shown in the following reaction scheme, a synthesis method of mercaptopyrrole derivative (A) by a reaction of a (2-oxoethyl)malononitrile derivative with hydrogen sulfide; however, a desulfurization reaction is not described.

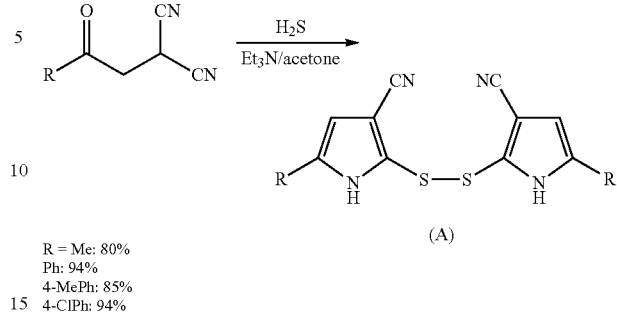

R = Me: 80%
Ph: 94%
4-MePh: 85%
4-ClPh: 94%

In addition, non-patent document 6 describes, as shown in the following reaction scheme, a synthesis method of 2-mercaptopyrrole derivative (B) having a cyano group at the 3-position is described; however, it is not by a ring closure reaction of a (2-oxoethyl)malononitrile derivative and a sulfur compound. Furthermore, a desulfurization reaction of the obtained 2-mercaptopyrrole derivative is not described.

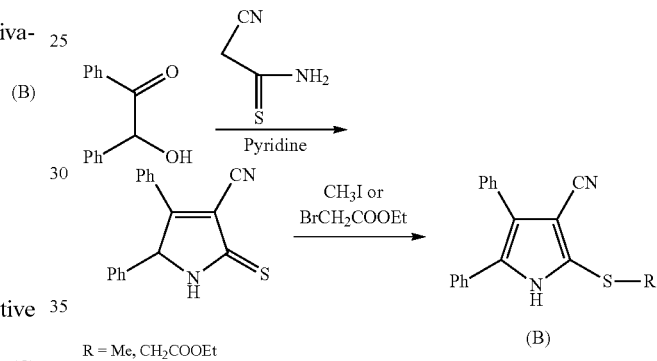

R = Me, CH₂COOEt

Moreover, patent document 11 describes, as shown in the following reaction scheme, a synthesis method of 2-mercaptopyrrole derivative (C) having a cyano group at the 3-position; however, it is not by a ring closure reaction of a (2-oxoethyl)malononitrile derivative and a sulfur compound. Furthermore, a desulfurization reaction of the obtained 2-mercaptopyrrole derivative is not described.

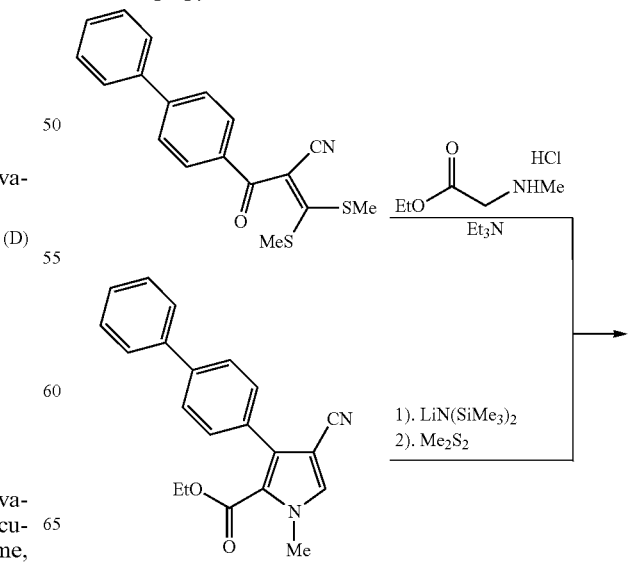

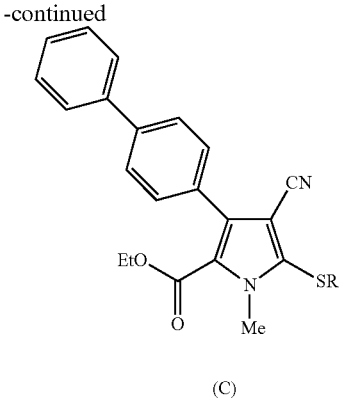

(C)

R = Me, Et

Moreover, patent document 12 describes, as shown in the following reaction scheme, a synthesis method of 2-mercaptopyrrole derivative (D) having a cyano group at the 3-position; however, it is not by a ring closure reaction of a (2-oxoethyl)malononitrile derivative and a sulfur compound. In addition, a desulfurization reaction of the obtained 2-mercaptopyrrole derivative is not described.

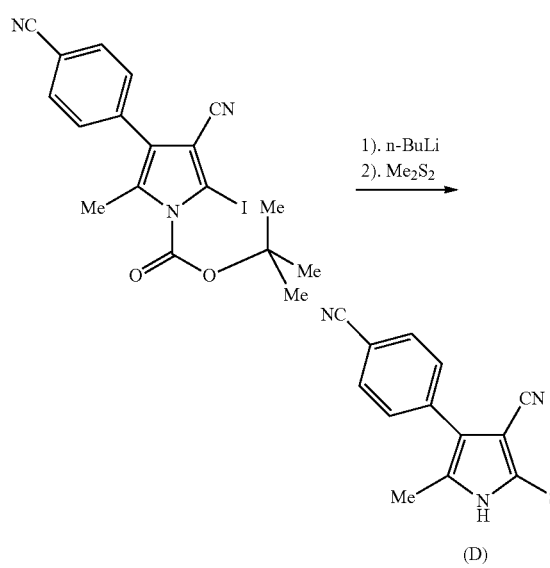

(D)

DOCUMENT LIST

Patent Documents patent document 1: WO2006/036024
patent document 2: WO2007/026916
patent document 3: WO2004/103968
patent document 4: JP-A-6-9554
patent document 5: U.S. Pat. No. 4,904,687
patent document 6: EP-A-358047
patent document 7: EP-A-491136
patent document 8: U.S. Pat. No. 5,359,090
patent document 9: U.S. Pat. No. 5,563,279
patent document 10: JP-A-10-324687
patent document 11: WO2005/040110
patent document 12: WO2006/064944

Non-Patent Documents non-patent document 1: J. Med. Chem., 1995, 38 (12), 2158-2165
non-patent document 2: Nucleosides Nucleotides, 1997, 16 (7-9), 941-944
non-patent document 3: J. Med. Chem., 1995, 38 (20), 4106-4144
non-patent document 4: Can. J. Chem., 1980, 58, 409-411
non-patent document 5: Chemistry Heterocyclic Compound, 1992, vol. 2, page 277
non-patent document 6: Tetrahedron, 1991, vol. 47, page 8243

SUMMARY OF THE INVENTION

A more efficient production method of a sulfonylpyrrole compound useful as a pharmaceutical product is desired. In addition, provision of an intermediate used for this method is desired.

The present inventors have intensively studied a production method of a sulfonylpyrrole compound useful as an acid secretion inhibitor, particularly a compound represented by the formula (VIII):

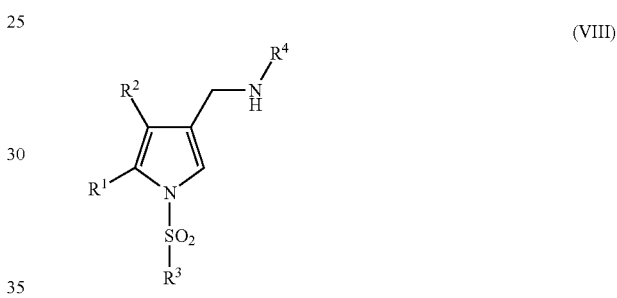

(VIII)

wherein $R^1$ is an optionally substituted hydrocarbon group or an optionally substituted heterocyclic group, $R^2$ is a hydrogen atom, an optionally substituted alkyl group, an acyl group, an optionally substituted hydroxy group, an optionally substituted amino group, a chlorine atom or a fluorine atom, $R^3$ is an optionally substituted hydrocarbon group or an optionally substituted heterocyclic group, and $R^4$ is an alkyl group, or a salt thereof. As a result, they have found a novel production method of a sulfonylpyrrole compound, which uses a 3-cyanopyrrole compound. In addition, they have found a novel production method of a 3-cyanopyrrole compound, which is an intermediate, and a novel intermediate, which resulted in the completion of the present invention.

Accordingly, the present invention relates to the following invention.

(1) A method of producing a compound represented by the formula

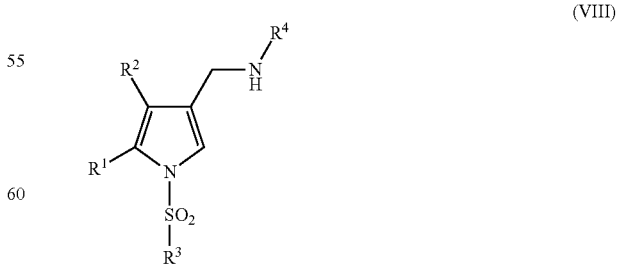

(VIII)

wherein $R^1$ is an optionally substituted hydrocarbon group or an optionally substituted heterocyclic group, $R^2$ is a hydrogen atom, an optionally substituted alkyl group, an acyl group, an optionally substituted hydroxy group, an optionally substituted amino group, a chlorine atom or a fluorine atom, $R^3$ is an optionally substituted hydrocarbon group or an optionally substituted heterocyclic group, and $R^4$ is an alkyl group, or a salt thereof, comprising
(I) reducing a compound represented by the formula

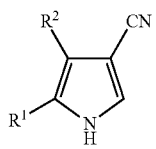

(III)

wherein each symbol is as defined above, or a salt thereof, and hydrolyzing the reduced product to give a compound represented by the formula

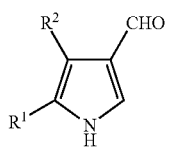

(IV)

wherein each symbol is as defined above, or a salt thereof,
(II) reacting the obtained compound with a compound represented by the formula $$R^3\text{—}SO_2\text{—}X \quad (V)$$

wherein $R^3$ is as defined above and X is a leaving group, or a salt thereof, to give a compound represented by the formula

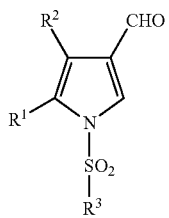

(VI)

wherein each symbol is as defined above, or a salt thereof, and
(III) reacting the obtained compound with a compound represented by the formula $$R^4\text{—}NH_2 \quad (VII)$$

wherein $R^4$ is as defined above, or a salt thereof, in the presence of a reducing agent;
(2) a method of producing a compound represented by the formula

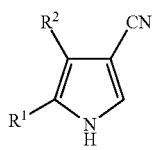

(III)

wherein $R^1$ is an optionally substituted hydrocarbon group or an optionally substituted heterocyclic group, and $R^2$ is a hydrogen atom, an optionally substituted alkyl group, an acyl group, an optionally substituted hydroxy group, an optionally substituted amino group, a chlorine atom or a fluorine atom, or a salt thereof, comprising subjecting a compound represented by the formula

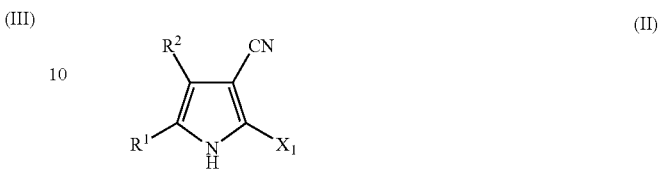

(II)

wherein $X_1$ is a halogen atom and other symbols are as defined above, or a salt thereof, to dehalogenation;
(3) the production method of the aforementioned (2), wherein the dehalogenation is performed in the presence of a base;
(4) a method of producing a compound represented by the formula

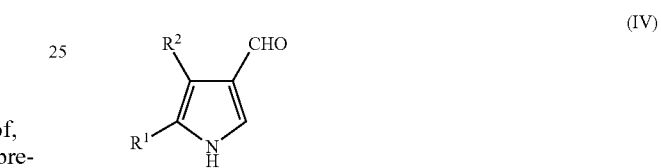

(IV)

wherein $R^1$ is an optionally substituted hydrocarbon group or an optionally substituted heterocyclic group, and $R^2$ is a hydrogen atom, an optionally substituted alkyl group, an acyl group, an optionally substituted hydroxy group, an optionally substituted amino group, a chlorine atom or a fluorine atom, or a salt thereof, comprising reducing a compound represented by the formula

(III)

wherein each symbol is as defined above, or a salt thereof, and hydrolyzing the reduced product;
(5) a method of producing a compound represented by the formula

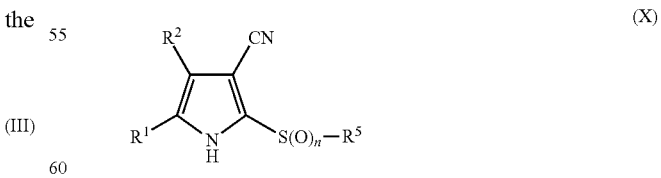

(X)

wherein $R^1$ is an optionally substituted hydrocarbon group or an optionally substituted heterocyclic group, $R^2$ is a hydrogen atom, an optionally substituted alkyl group, an acyl group, an optionally substituted hydroxy group, an optionally substituted amino group, a chlorine atom or a fluorine atom, $R^5$ is an optionally substituted hydrocarbon group, an optionally substituted heterocyclic group, an acyl group or a group represented by —S—R⁶ (R⁶ is an optionally substituted hydrocarbon group or an optionally substituted heterocyclic group), and n is 0, 1 or 2, or a salt thereof, comprising reacting a compound represented by the formula

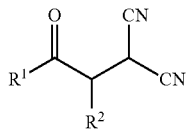
(I)

wherein each symbol is as defined above, or a salt thereof, with a compound represented by the formula

R⁵S(O)ₙH wherein R⁵ and n are as defined above, or a salt thereof;
(6) a method of producing a compound represented by the formula

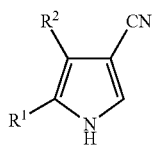
(III)

wherein R¹ is an optionally substituted hydrocarbon group or an optionally substituted heterocyclic group, and R² is a hydrogen atom, an optionally substituted alkyl group, an acyl group, an optionally substituted hydroxy group, an optionally substituted amino group, a chlorine atom or a fluorine atom, or a salt thereof, comprising subjecting a compound represented by the formula

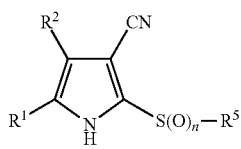
(X)

wherein R¹ and R² are as defined above, R⁵ is an optionally substituted hydrocarbon group, an optionally substituted heterocyclic group, an acyl group or a group represented by —S—R⁶ (R⁶ is an optionally substituted hydrocarbon group or an optionally substituted heterocyclic group), and n is 0, 1 or 2, or a salt thereof, to a desulfurization reaction;
(7) a method of producing a compound represented by the formula

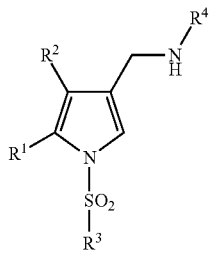
(VIII)

wherein R¹ is an optionally substituted hydrocarbon group or an optionally substituted heterocyclic group, R² is a hydrogen atom, an optionally substituted alkyl group, an acyl group, an optionally substituted hydroxy group, an optionally substituted amino group, a chlorine atom or a fluorine atom, R³ is an optionally substituted hydrocarbon group or an optionally substituted heterocyclic group, and R⁴ is an alkyl group, or a salt thereof, comprising (I) reacting a compound represented by the formula

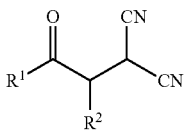
(I)

wherein each symbol is as defined above, or a salt thereof, with a compound represented by the formula

R⁵S(O)ₙH wherein R⁵ is an optionally substituted hydrocarbon group, an optionally substituted heterocyclic group, an acyl group or a group represented by —S—R⁶ (R⁶ is an optionally substituted hydrocarbon group or an optionally substituted heterocyclic group), and n is 0, 1 or 2, or a salt thereof, to give a compound represented by the formula

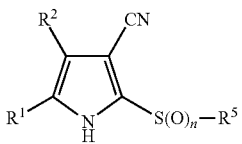
(X)

wherein each symbol is as defined above, or a salt thereof, (II) subjecting the obtained compound to a desulfurization reaction to give a compound represented by the formula

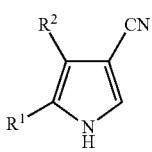
(III)

wherein each symbol is as defined above, or a salt thereof, (III) reacting the obtained compound with a compound represented by the formula

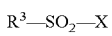
R³—SO₂—X          (V)

wherein R³ is as defined above, and X is a leaving group, or a salt thereof, to give a compound represented by the formula

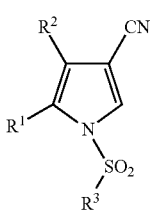
(XVII)

wherein each symbol is as defined above, or a salt thereof, (IV) reducing the obtained compound and hydrolyzing the reduced product to give a compound represented by the formula

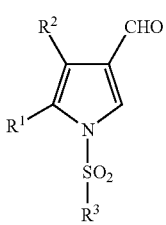
(VI)

wherein each symbol is as defined above, or a salt thereof, and (V) reacting the obtained compound with a compound represented by the formula

    (VII)

wherein R⁴ is as defined above, or a salt thereof;

(8) a method of producing a compound represented by the formula

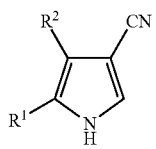    (III)

wherein $R^1$ is an optionally substituted hydrocarbon group or an optionally substituted heterocyclic group, and $R^2$ is a hydrogen atom, an optionally substituted alkyl group, an acyl group, an optionally substituted hydroxy group, an optionally substituted amino group, a chlorine atom or a fluorine atom, or a salt thereof, comprising subjecting a compound represented by the formula

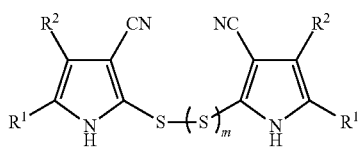    (XI)

wherein m is 0 or 1 and other symbols are as defined above, or a salt thereof, to a desulfurization reaction;

(9) a method of producing a compound represented by the formula

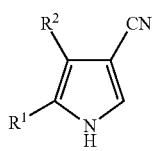    (III)

wherein $R^1$ is an optionally substituted hydrocarbon group or an optionally substituted heterocyclic group, and $R^2$ is a hydrogen atom, an optionally substituted alkyl group, an acyl group, an optionally substituted hydroxy group, an optionally substituted amino group, a chlorine atom or a fluorine atom, or a salt thereof, comprising reacting a compound represented by the formula

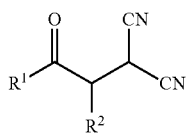    (I)

wherein each symbol is as defined above, or a salt thereof, with a sulfur reagent to give a compound represented by the formula

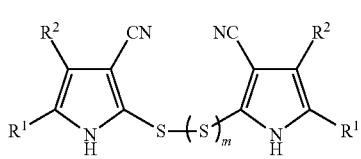    (XI)

wherein m is 0 or 1, and other symbols are as defined above, or a salt thereof, and subjecting the obtained compound to a desulfurization reaction;

(10) a method of producing a compound represented by the formula

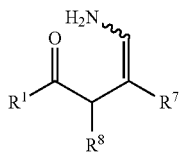    (XIII)

wherein $R^1$ is an optionally substituted hydrocarbon group or an optionally substituted heterocyclic group, $R^7$ is a cyano group or a substituted carboxyl group, and $R^8$ is a hydrogen atom, an optionally substituted hydrocarbon group, an optionally substituted heterocyclic group, a chlorine atom or a fluorine atom, or a salt thereof, comprising subjecting a compound represented by the formula

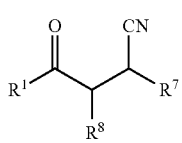    (XII)

wherein each symbol is as defined above, or a salt thereof, to a reduction reaction;

(11) a method of producing a compound represented by the formula

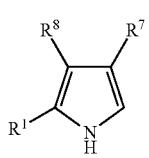    (XIV)

wherein $R^1$ is an optionally substituted hydrocarbon group or an optionally substituted heterocyclic group, $R^7$ is a cyano group or a substituted carboxyl group, and $R^8$ is a hydrogen atom, an optionally substituted hydrocarbon group, an optionally substituted heterocyclic group, a chlorine atom or a fluorine atom, or a salt thereof, comprising cyclizing a compound represented by the formula

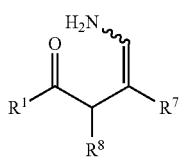    (XIII)

wherein each symbol is as defined above, or a salt thereof;

(12) a method of producing a compound represented by the formula

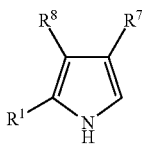
(XIV)

wherein R¹ is an optionally substituted hydrocarbon group or an optionally substituted heterocyclic group, R⁷ is a cyano group or a substituted carboxyl group, and R⁸ is a hydrogen atom, an optionally substituted hydrocarbon group, an optionally substituted heterocyclic group, a chlorine atom or a fluorine atom, or a salt thereof, comprising reducing a compound represented by the formula

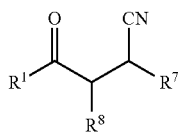
(XII)

wherein each symbol is as defined above, or a salt thereof, and cyclizing the reduced product;

(13) a method of producing a compound represented by the formula

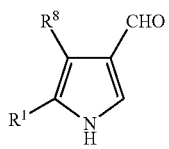
(XVI)

wherein R¹ is an optionally substituted hydrocarbon group or an optionally substituted heterocyclic group, and R⁸ is a hydrogen atom, an optionally substituted hydrocarbon group, an optionally substituted heterocyclic group, a chlorine atom or a fluorine atom, or a salt thereof, comprising cyclizing a compound represented by the formula

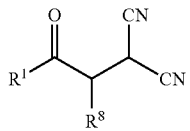
(XV)

wherein each symbol is as defined above, or a salt thereof, in the presence of a reducing agent;

(14) a compound represented by the formula

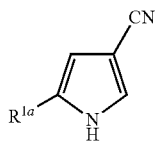

wherein $R^{1a}$ is an aryl group having substituent(s), or a salt thereof;

(15) a compound represented by the formula

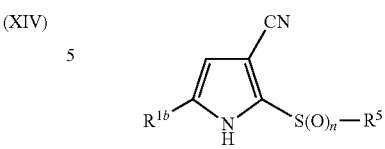

wherein $R^{1b}$ is an optionally substituted hydrocarbon group or an optionally substituted heterocyclic group, R⁵ is an optionally substituted hydrocarbon group, an optionally substituted heterocyclic group, an acyl group or a group represented by —S—R⁶ (R⁶ is an optionally substituted hydrocarbon group or an optionally substituted heterocyclic group), and n is 0, 1 or 2 (excluding 2,2'-dithiobis(5-methyl-1H-pyrrole-3-carbonitrile), 2,2'-dithiobis(5-phenyl-1H-pyrrole-3-carbonitrile), 2,2'-dithiobis[5-(4-chlorophenyl)-1H-pyrrole-3-carbonitrile], 2,2'-dithiobis[5-(4-methylphenyl)-1H-pyrrole-3-carbonitrile] and 2,2'-dithiobis[5-(4-methoxyphenyl)-1H-pyrrole-3-carbonitrile]), or a salt thereof.

Effect of the Invention

According to the method of the present invention, since a sulfonylpyrrole compound is obtained in a short step as compared to conventional methods, the sulfonylpyrrole compound can be produced at a low cost.

In addition, as a synthesis method of the above-mentioned intermediate 3-cyanopyrrole compound, a (2-oxoethyl)malononitrile compound is reacted with a sulfur compound to give a 2-mercapto-3-cyanopyrrole compound, which is then subjected to a desulfurization reaction to give the object compound in a high yield. Furthermore, 2-mercapto-3-cyanopyrrole can be used as a novel intermediate for a 3-cyanopyrrole compound.

The present invention relates to a production method of a sulfonylpyrrole compound useful as an acid secretion inhibitor, particularly, a compound represented by the formula (VIII):

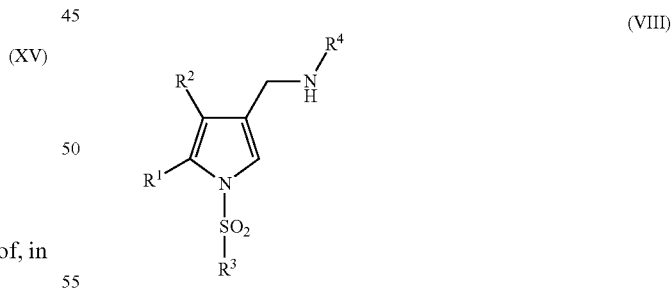
(VIII)

wherein R¹ is an optionally substituted hydrocarbon group or an optionally substituted heterocyclic group, R² is a hydrogen atom, an optionally substituted alkyl group, an acyl group, an optionally substituted hydroxy group, an optionally substituted amino group, a chlorine atom or a fluorine atom, R³ is an optionally substituted hydrocarbon group or an optionally substituted heterocyclic group, and R⁴ is an alkyl group (hereinafter sometimes to be abbreviated as compound (VIII)) or a salt thereof, a production method of an intermediate therefor and the like. Compound (VIII) or a salt thereof shows a highly strong proton pump inhibitory effect. Since compound (VIII)

or a salt thereof inhibits the proton pump ($H^+/K^+$-ATPase) activity reversibly and in a $K^+$ antagonist inhibitory manner to consequently suppress acid secretion, it is sometimes referred to as a potassium-competitive acid blocker: P-CAB or an acid pump antagonist (APA). Compound (VIII) or a salt thereof rapidly expresses action, and shows maximum efficacy from the initial administration. Furthermore, it is characterized by a small influence of metabolism polymorphisms (dispersion among patients), low cytotoxicity, weak cytochrome P450 (CYP) inhibitory activity and hERG inhibitory activity, and long duration of action. Therefore, compound (VIII) or a salt thereof obtained according to the production method of the present invention is useful as an agent clinically useful for the prophylaxis and/or treatment of peptic ulcer (e.g., gastric ulcer, duodenal ulcer, anastomotic ulcer, ulcer caused by non-steroidal anti-inflammatory agents, ulcer due to postoperative stress etc.); Zollinger-Ellison syndrome; gastritis; erosive esophagitis; symptomatic gastroesophageal reflux disease (symptomatic GERD); Barrett esophagus, functional dyspepsia; gastric cancer; stomach MALT lymphoma; gastric hyperacidity; or an inhibitor of upper gastrointestinal hemorrhage due to peptic ulcer, acute stress ulcer, hemorrhagic gastritis or invasive stress or recurrence of ulcer due to non-steroidal anti-inflammatory agents and the like. Since compound (VIII) or a salt thereof shows low toxicity and is superior in water-solubility, in vivo kinetics and efficacy expression, it is useful as a pharmaceutical composition. Moreover, since compound (VIII) or a salt thereof is stable even under acidic conditions, it can be administered orally as a conventional tablet and the like without being formulated as an enteric-coated preparation. This has a consequence that the preparation of tablet and the like can be made smaller, which is advantageous in that it is easily swallowed by patients having difficulty in swallowing, particularly the elderly and children. In addition, since a sustained release effect afforded by enteric-coated preparations is absent, expression of a gastric acid secretion-suppressive action is rapid, and alleviation of symptoms such as pain and the like is rapid.

DETAILED DESCRIPTION OF THE INVENTION

The definition of each symbol in the formula is explained in detail in the following.

Examples of the halogen atom for $X_1$ include chlorine, bromine and the like.

Examples of the "hydrocarbon group" of the "optionally substituted hydrocarbon group" for $R^1$ include a chain or cyclic hydrocarbon group (e.g., alkyl, alkenyl, alkynyl, cycloalkyl, aryl, aralkyl etc.). Of these, a chain or cyclic hydrocarbon group having a carbon number of 1 to 16 and the like are preferable.

Examples of the "alkyl" include $C_{1-6}$ alkyl (e.g., methyl, ethyl, propyl, isopropyl, butyl, isobutyl, sec-butyl, tert-butyl, pentyl, hexyl etc.) and the like.

Examples of the "alkenyl" include $C_{2-6}$ alkenyl (e.g., vinyl, allyl, isopropenyl, 1-butenyl, 2-butenyl, 3-butenyl, 2-methyl-2-propenyl, 1-methyl-2-propenyl, 2-methyl-1-propenyl etc.) and the like.

Examples of the "alkynyl" include $C_{2-6}$ alkynyl (e.g., ethynyl, propargyl, 1-butynyl, 2-butynyl, 3-butynyl, 1-hexynyl etc.) and the like.

Examples of the "cycloalkyl" include $C_{3-7}$ cycloalkyl (e.g., cyclopropyl, cyclobutyl, cyclopentyl, cyclohexyl, cycloheptyl etc.) and the like.

Examples of the "aryl" include $C_{6-14}$ aryl (e.g., phenyl, 1-naphthyl, 2-naphthyl, 2-biphenylyl, 3-biphenylyl, 4-biphenylyl, 2-anthryl etc.) and the like.

Examples of the "aralkyl" include $C_{7-16}$ aralkyl (e.g., phenyl-$C_{1-6}$ alkyl such as benzyl, phenethyl, diphenylmethyl, 1-naphthylmethyl, 2-naphthylmethyl, 2,2-diphenylethyl, 3-phenylpropyl, 4-phenylbutyl, 5-phenylpentyl and the like, naphthyl-$C_{1-6}$ alkyl, diphenyl-$C_{1-4}$ alkyl etc.) and the like.

When the above-mentioned hydrocarbon group is alkyl, alkenyl or alkynyl, it is optionally substituted by 1 to 3 substituents selected from (1) a halogen atom (e.g., a fluorine atom, a chlorine atom, a bromine atom, an iodine atom etc.), (2) nitro, (3) cyano, (4) hydroxy, (5) $C_{1-6}$ alkoxy (e.g., methoxy, ethoxy, propoxy, isopropoxy, butoxy, isobutoxy, sec-butoxy, pentyloxy, hexyloxy, fluoromethoxy etc.) optionally having 1 to 3 halogen atoms (e.g., a fluorine atom, a chlorine atom, a bromine atom, an iodine atom), (6) $C_{6-14}$ aryloxy (e.g., phenyloxy, naphthyloxy etc.), (7) $C_{7-16}$ aralkyloxy (e.g., benzyloxy, phenethyloxy, diphenylmethyloxy, 1-naphthylmethyloxy, 2-naphthylmethyloxy, 2,2-diphenylethyloxy, 3-phenylpropyloxy, 4-phenylbutyloxy, 5-phenylpentyloxy etc.), (8) mercapto, (9) $C_{1-6}$ alkylthio (e.g., methylthio, difluoromethylthio, trifluoromethylthio, ethylthio, propylthio, isopropylthio, butylthio, 4,4,4-trifluorobutylthio, pentylthio, hexylthio etc.) optionally having 1 to 3 halogen atoms (e.g., fluorine atom, chlorine atom, bromine atom, iodine atom), (10) $C_{6-14}$ arylthio (e.g., phenylthio, naphthylthio etc.), (11) $C_{7-16}$ aralkylthio (e.g., benzylthio, phenethylthio, diphenylmethylthio, 1-naphthylmethylthio, 2-naphthylmethylthio, 2,2-diphenylethylthio, 3-phenylpropylthio, 4-phenylbutylthio, 5-phenylpentylthio etc.), (12) amino, (13) mono-$C_{1-6}$ alkylamino (e.g., methylamino, ethylamino etc.), (14) mono-$C_{6-14}$ arylamino (e.g., phenylamino, 1-naphthylamino, 2-naphthylamino etc.), (15) mono-$C_{7-16}$ aralkylamino (e.g., benzylamino etc.), (16) di-$C_{1-6}$ alkylamino (e.g., dimethylamino, diethylamino etc.), (17) di-$C_{6-14}$ arylamino (e.g., diphenylamino etc.), (18) di-$C_{7-16}$ aralkylamino (e.g., dibenzylamino etc.), (19) formyl, (20) $C_{1-6}$ alkyl-carbonyl (e.g., acetyl, propionyl etc.), (21) $C_{6-14}$ aryl-carbonyl (e.g., benzoyl, 1-naphthoyl, 2-naphthoyl etc.), (22) carboxyl, (23) $C_{1-6}$ alkoxy-carbonyl (e.g., methoxycarbonyl, ethoxycarbonyl, propoxycarbonyl, tert-butoxycarbonyl etc.), (24) $C_{6-14}$ aryloxy-carbonyl (e.g., phenoxycarbonyl etc.), (25) carbamoyl, (26) thiocarbamoyl, (27) mono-$C_{1-6}$ alkyl-carbamoyl (e.g., methylcarbamoyl, ethylcarbamoyl etc.), (28) di-$C_{1-6}$ alkyl-carbamoyl (e.g., dimethylcarbamoyl, diethylcarbamoyl, ethylmethylcarbamoyl etc.), (29) $C_{6-14}$ aryl-carbamoyl (e.g., phenylcarbamoyl, 1-naphthylcarbamoyl, 2-naphthylcarbamoyl etc.), (30) $C_{1-6}$ alkylsulfonyl (e.g., methylsulfonyl, ethylsulfonyl etc.), (31) $C_{6-14}$ arylsulfonyl (e.g., phenylsulfonyl, 1-naphthylsulfonyl, 2-naphthylsulfonyl etc.), (32) $C_{1-6}$ alkylsulfinyl (e.g., methylsulfinyl, ethylsulfinyl etc.), (33) $C_{6-14}$ arylsulfinyl (e.g., phenylsulfinyl, 1-naphthylsulfinyl, 2-naphthylsulfinyl etc.), (34) formylamino, (35) $C_{1-6}$ alkyl-carbonylamino (e.g., acetylamino etc.), (36) $C_{6-14}$ aryl-carbonylamino (e.g., benzoylamino, naphthoylamino etc.), (37) $C_{1-6}$ alkoxy-carbonylamino (e.g., methoxycarbonylamino, ethoxycarbonylamino, propoxycarbonylamino, butoxycarbonylamino etc.), (38) $C_{1-6}$ alkylsulfonylamino (e.g., methylsulfonylamino, ethylsulfonylamino etc.), (39) $C_{6-14}$ arylsulfonylamino (e.g., phenylsulfonylamino, 2-naphthylsulfonylamino, 1-naphthylsulfonylamino etc.), (40) $C_{1-6}$ alkyl-carbonyloxy (e.g., acetoxy, propionyloxy etc.), (41) $C_{6-14}$ aryl-carbonyloxy (e.g., benzoyloxy, naphthylcarbonyloxy etc.), (42) $C_{1-6}$ alkoxy-carbonyloxy (e.g., methoxycarbonyloxy, ethoxycarbonyloxy, propoxycarbonyloxy, butoxycarbonyloxy etc.), (43) mono-$C_{1-6}$ alkyl-carbamoyloxy (e.g., methylcarbamoyloxy, ethylcarbamoyloxy etc.), (44) di-$C_{1-6}$ alkyl-carbamoyloxy (e.g., dimethylcarbamoyloxy, diethylcarbamoyloxy etc.), (45) $C_{6-14}$ aryl-carbamoyloxy (e.g., phenylcarbamoyloxy, naphthylcarbamoyloxy etc.), (46) a 5- to 7-membered saturated cyclic amino (e.g., pyrrolidin-1-yl, piperidino, piperazin-1-yl, morpholino, thiomorpholino, hexahydroazepin-1-yl etc.) optionally containing, besides one nitrogen atom and carbon atom, 1 or 2 kinds of 1 to 4 hetero atoms selected from a nitrogen atom, a sulfur atom and an oxygen atom, (47) a 5- to 10-membered aromatic heterocyclic group (e.g., 2-thienyl, 3-thienyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl etc.) containing, besides carbon atom, 1 or 2 kinds of 1 to 4 hetero atoms selected from a nitrogen atom, a sulfur atom and an oxygen atom, (48) $C_{1-3}$ alkylenedioxy (e.g., methylenedioxy, ethylenedioxy etc.), (49) $C_{3-7}$ cycloalkyl (e.g., cyclopropyl, cyclobutyl, cyclopentyl, cyclohexyl, cycloheptyl etc.), and the like.

In addition, when the above-mentioned hydrocarbon group is cycloalkyl, aryl or aralkyl, it is optionally substituted by 1 to 5 (preferably 1 to 3) substituents selected from (1) a halogen atom (e.g., a fluorine atom, a chlorine atom, a bromine atom, an iodine atom etc.), (2) nitro, (3) cyano, (4) hydroxy, (5) $C_{1-6}$ alkoxy (e.g., methoxy, ethoxy, propoxy, isopropoxy, butoxy, isobutoxy, sec-butoxy, pentyloxy, hexyloxy, fluoromethoxy etc.) optionally having 1 to 3 halogen atoms (e.g., a fluorine atom, a chlorine atom, a bromine atom, an iodine atom), (6) $C_{6-14}$ aryloxy (e.g., phenyloxy, naphthyloxy etc.), (7) $C_{7-16}$ aralkyloxy (e.g., benzyloxy, phenethyloxy, diphenylmethyloxy, 1-naphthylmethyloxy, 2-naphthylmethyloxy, 2,2-diphenylethyloxy, 3-phenylpropyloxy, 4-phenylbutyloxy, 5-phenylpentyloxy etc.), (8) mercapto, (9) $C_{1-6}$ alkylthio (e.g., methylthio, difluoromethylthio, trifluoromethylthio, ethylthio, propylthio, isopropylthio, butylthio, 4,4,4-trifluorobutylthio, pentylthio, hexylthio etc.) optionally having 1 to 3 halogen atoms (e.g., fluorine atom, chlorine atom, bromine atom, iodine atom), (10) $C_{6-14}$ arylthio (e.g., phenylthio, naphthylthio etc.), (11) $C_{7-16}$ aralkylthio (e.g., benzylthio, phenethylthio, diphenylmethylthio, 1-naphthylmethylthio, 2-naphthylmethylthio, 2,2-diphenylethylthio, 3-phenylpropylthio, 4-phenylbutylthio, 5-phenylpentylthio etc.), (12) amino, (13) mono-$C_{1-6}$ alkylamino (e.g., methylamino, ethylamino etc.), (14) mono-$C_{6-14}$ arylamino (e.g., phenylamino, 1-naphthylamino, 2-naphthylamino etc.), (15) mono-$C_{7-16}$ aralkylamino (e.g., benzylamino etc.), (16) di-$C_{1-6}$ alkylamino (e.g., dimethylamino, diethylamino etc.), (17) di-$C_{6-14}$ arylamino (e.g., diphenylamino etc.), (18) di-$C_{7-16}$ aralkylamino (e.g., dibenzylamino etc.), (19) formyl, (20) $C_{1-6}$ alkyl-carbonyl (e.g., acetyl, propionyl etc.), (21) $C_{6-14}$ aryl-carbonyl (e.g., benzoyl, 1-naphthoyl, 2-naphthoyl etc.), (22) carboxyl, (23) $C_{1-6}$ alkoxy-carbonyl (e.g., methoxycarbonyl, ethoxycarbonyl, propoxycarbonyl, tert-butoxycarbonyl etc.), (24) $C_{6-14}$ aryloxy-carbonyl (e.g., phenoxycarbonyl etc.), (25) carbamoyl, (26) thiocarbamoyl, (27) mono-$C_{1-6}$ alkyl-carbamoyl (e.g., methylcarbamoyl, ethylcarbamoyl etc.), (28) di-$C_{1-6}$ alkyl-carbamoyl (e.g., dimethylcarbamoyl, diethylcarbamoyl, ethylmethylcarbamoyl etc.), (29) $C_{6-14}$ aryl-carbamoyl (e.g., phenylcarbamoyl, 1-naphthylcarbamoyl, 2-naphthylcarbamoyl etc.), (30) $C_{1-6}$ alkylsulfonyl (e.g., methylsulfonyl, ethylsulfonyl, trifluoromethylsulfonyl etc.) optionally having 1 to 3 halogen atoms (e.g., a fluorine atom, a chlorine atom, a bromine atom, an iodine atom), (31) $C_{6-14}$ arylsulfonyl (e.g., phenylsulfonyl, 1-naphthylsulfonyl, 2-naphthylsulfonyl etc.), (32) $C_{1-6}$ alkyl-sulfinyl (e.g., methylsulfinyl, ethylsulfinyl etc.), (33) $C_{6-14}$ arylsulfinyl (e.g., phenylsulfinyl, 1-naphthylsulfinyl, 2-naphthylsulfinyl etc.), (34) formylamino, (35) $C_{1-6}$ alkyl-carbonylamino (e.g., acetylamino etc.), (36) $C_{6-14}$ aryl-carbonylamino (e.g., benzoylamino, naphthoylamino etc.), (37) $C_{1-6}$ alkoxy-carbonylamino (e.g., methoxycarbonylamino, ethoxycarbonylamino, propoxycarbonylamino, butoxycarbonylamino etc.), (38) $C_{1-6}$ alkylsulfonylamino (e.g., methylsulfonylamino, ethylsulfonylamino etc.), (39) $C_{6-14}$ arylsulfonylamino (e.g., phenylsulfonylamino, 2-naphthylsulfonylamino, 1-naphthylsulfonylamino etc.), (40) $C_{1-6}$ alkyl-carbonyloxy (e.g., acetoxy, propionyloxy etc.), (41) $C_{6-14}$ aryl-carbonyloxy (e.g., benzoyloxy, naphthylcarbonyloxy etc.), (42) $C_{1-6}$ alkoxy-carbonyloxy (e.g., methoxycarbonyloxy, ethoxycarbonyloxy, propoxycarbonyloxy, butoxycarbonyloxy etc.), (43) mono-$C_{1-6}$ alkyl-carbamoyloxy (e.g., methylcarbamoyloxy, ethylcarbamoyloxy etc.), (44) di-$C_{1-6}$ alkyl-carbamoyloxy (e.g., dimethylcarbamoyloxy, diethylcarbamoyloxy etc.), (45) $C_{6-14}$ aryl-carbamoyloxy (e.g., phenylcarbamoyloxy, naphthylcarbamoyloxy etc.), (46) a 5- to 7-membered saturated cyclic amino (e.g., pyrrolidin-1-yl, piperidino, piperazin-1-yl, morpholino, thiomorpholino, hexahydroazepin-1-yl etc.) optionally containing, besides one nitrogen atom and carbon atom, 1 or 2 kinds of 1 to 4 hetero atoms selected from a nitrogen atom, a sulfur atom and an oxygen atom, (47) a 5- to 10-membered aromatic heterocyclic group (e.g., 2-thienyl, 3-thienyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl etc.) containing, besides carbon atom, 1 or 2 kinds of 1 to 4 hetero atoms selected from a nitrogen atom, a sulfur atom and an oxygen atom, (48) $C_{1-3}$ alkylenedioxy (e.g., methylenedioxy, ethylenedioxy etc.), (49) $C_{3-7}$ cycloalkyl (e.g., cyclopropyl, cyclobutyl, cyclopentyl, cyclohexyl, cycloheptyl etc.), (50) $C_{1-6}$ alkyl group (e.g., methyl, ethyl, n-propyl, isopropyl, n-butyl, isobutyl, sec-butyl, tert-butyl, n-pentyl, sec-pentyl, isopentyl, neopentyl, n-hexyl, isohexyl etc.) optionally having 1 to 3 halogen atoms (e.g., fluorine, chlorine, bromine, iodine), (51) a $C_{2-6}$ alkenyl group (e.g., allyl, isopropenyl, isobutenyl, 1-methylallyl, 2-pentenyl, 2-hexenyl etc.) optionally having 1 to 3 halogen atoms (e.g., fluorine, chlorine, bromine, iodine), (52) a $C_{2-6}$ alkynyl group (e.g., propargyl, 2-butynyl, 3-butynyl, 3-pentynyl, 3-hexynyl etc.), (53) mono-$C_{3-7}$ cycloalkyl-carbamoyl (e.g., cyclopropylcarbamoyl, cyclobutylcarbamoyl etc.), and (54) 5- to 10-membered heterocyclyl-carbonyl containing, besides carbon atom, 1 or 2 kinds of 1 to 4 hetero atoms selected from a nitrogen atom, a sulfur atom and an oxygen atom (e.g., 4-morpholinocarbonyl etc.) and the like.

Examples of the "heterocyclic group" of the "optionally substituted heterocyclic group" for $R^1$ include a 3- to 8-membered heterocyclic group (preferably a 5- or 6-membered heterocyclic group) containing 1 to 4 hetero atoms such as a nitrogen atom (optionally oxidized), an oxygen atom, a sulfur atom (optionally mono- or dioxidized) and the like, or a 3- to 8-membered heterocyclic group (preferably a 5- or 6-membered heterocyclic group) containing 1 to 4 hetero atoms such as a nitrogen atom (optionally oxidized), an oxygen atom, a sulfur atom (optionally mono- or dioxidized) and the like, with a benzene ring; or a group formed by condensing a 3- to 8-membered heterocyclic group (preferably 5- or 6-membered heterocyclic group) containing 1 to 4 hetero atoms such as a nitrogen atom (optionally oxidized), an oxygen atom, a sulfur atom (optionally mono- or dioxidized) and the like, preferably a group formed by condensing the 5- or 6-membered heterocyclic group with a 5- or 6-membered ring containing 1 to 4 hetero atoms such as a nitrogen atom (optionally oxidized), an oxygen atom, a sulfur atom (optionally mono- or dioxidized) and the like.

Specifically, aziridinyl (e.g., 1- or 2-aziridinyl), azirinyl (e.g., 1- or 2-azirinyl), azetyl (e.g., 2-, 3- or 4-azetyl), azetidinyl (e.g., 1-, 2- or 3-azetidinyl), perhydroazepinyl (e.g., 1-, 2-, 3- or 4-perhydroazepinyl), perhydroazocinyl (e.g., 1-, 2-, 3-, 4- or 5-perhydroazocinyl), pyrrolyl (e.g., 1-, 2- or 3-pyrrolyl), pyrazolyl (e.g., 1-, 3-, 4- or 5-pyrazolyl), imidazolyl (e.g., 1-, 2-, 4- or 5-imidazolyl), triazolyl (e.g., 1,2,3-triazole-1-, 4- or 5-yl, 1,2,4-triazol-1-, 3-, 4- or 5-yl), tetrazolyl (e.g., tetrazol-1-, 2- or 5-yl), furyl (e.g., 2- or 3-furyl), thienyl (e.g., 2- or 3-thienyl), thienyl wherein sulfur atom is oxidized (e.g., 2- or 3-thienyl-1,1-dioxide), oxazolyl (e.g., 2-, 4- or 5-oxazolyl), isoxazolyl (e.g., 3-, 4- or 5-isoxazolyl), oxadiazolyl (e.g., 1,2,3-oxadiazol-4- or 5-yl, 1,2,4-oxadiazol-3- or 5-yl, 1,2,5-oxadiazol-3-yl, 1,3,4-oxadiazol-2-yl), triazolyl (e.g., 2-, 4- or 5-thiazolyl), isothiazolyl (e.g., 3-, 4- or 5-isothiazolyl), thiadiazolyl (e.g., 1,2,3-thiadiazol-4- or 5-yl, 1,2,4-thiadiazol-3- or 5-yl, 1,2,5-thiadiazol-3-yl, 1,3,4-thiadiazol-2-yl), pyrrolidinyl (e.g., 1-, 2- or 3-pyrrolidinyl), pyridyl (e.g., 2-, 3- or 4-pyridyl), pyridyl wherein nitrogen atom is oxidized (e.g., 2-, 3- or 4-pyridyl-N-oxide), pyridazinyl (e.g., 3- or 4-pyridazinyl), pyridazinyl wherein one or both of nitrogen atoms is/are oxidized (e.g., 3-, 4-, 5- or 6-pyridazinyl-N-oxide), pyrimidinyl (e.g., 2-, 4- or 5-pyrimidinyl), pyrimidinyl wherein one or both of nitrogen atoms is/are oxidized (e.g., 2-, 4-, 5- or 6-pyrimidinyl-N-oxide), pyrazinyl, piperidinyl (e.g., 1-, 2-, 3- or 4-piperidinyl), piperazinyl (e.g., 1- or 2-piperazinyl), indolyl (e.g., 3H-indol-2-, 3-, 4-, 5-, 6- or 7-yl), pyranyl (e.g., 2-, 3- or 4-pyranyl), thiopyranyl (e.g., 2-, 3- or 4-thiopyranyl), thiopyranyl wherein sulfur atom is oxidized (e.g., 2-, 3- or 4-thiopyranyl-1,1-dioxide), morpholinyl (e.g., 2-, 3- or 4-morpholinyl), thiomorpholinyl, quinolyl (e.g., 2-, 3-, 4-, 5-, 6-, 7- or 8-quinolyl), isoquinolyl, pyrido[2,3-d]pyrimidinyl (e.g., pyrido[2,3-d]pyrimidin-2-yl), naphthyridinyl such as 1,5-, 1,6-, 1,7-, 1,8-, 2,6- or 2,7-naphthyridinyl and the like (e.g., 1,5-naphthyridin-2- or 3-yl), thieno[2,3-d]pyridyl (e.g., thieno[2,3-d]pyridin-3-yl), pyrazinoquinolyl (e.g., pyrazino[2,3-d]quinolin-2-yl), chromenyl (e.g., 2H-chromen-2- or 3-yl), 2-benzo[b]thienyl, 3-benzo[b]thienyl, 2-benzo[b]furanyl, 3-benzo[b]furanyl, 2,3-dihydro-1-benzofuranyl, 2,1,3-benzothiadiazolyl, 2,3-dihydro-1,4-benzodioxin-5- or -6-yl, 1,3-benzothiazol-6-yl, 1,1-dioxide-2,3-dihydro-1-benzothien-6-yl, 1-benzothienyl and the like are used.

Examples of the "substituent" of the heterocyclic group include those similar to the substituents optionally present when the "hydrocarbon group" for the above-mentioned $R^1$ is cycloalkyl, aryl or aralkyl. The number of the substituents is 1 to 5, preferably 1 to 3.

Examples of the "alkyl group" of the "optionally substituted alkyl group" for $R^2$ include $C_{1-6}$ alkyl groups such as methyl, ethyl, propyl, isopropyl, butyl, isobutyl, sec-butyl, tert-butyl, pentyl, hexyl and the like, and the like.

As the substituent that the "alkyl group" optionally has, (1) a halogen atom (e.g., fluorine atom, chlorine atom, bromine atom, iodine atom etc.), (2) nitro, (3) cyano, (4) hydroxy, (5) $C_{1-6}$ alkoxy (e.g., methoxy, ethoxy, propoxy, isopropoxy, butoxy, isobutoxy, sec-butoxy, pentyloxy, hexyloxy, fluoromethoxy etc.) optionally having 1 to 3 halogen atoms (e.g., fluorine, chlorine, bromine, iodine), (6) $C_{6-14}$ aryloxy (e.g., phenyloxy, naphthyloxy etc.), (7) $C_{7-16}$ aralkyloxy (e.g., benzyloxy, phenethyloxy, diphenylmethyloxy, 1-naphthylmethyloxy, 2-naphthylmethyloxy, 2,2-diphenylethyloxy, 3-phenylpropyloxy, 4-phenylbutyloxy, 5-phenylpentyloxy etc.), (8) mercapto, (9) $C_{1-6}$ alkylthio (e.g., methylthio, difluoromethylthio, trifluoromethylthio, ethylthio, propylthio, isopropylthio, butylthio, 4,4,4-trifluorobutylthio, pentylthio, hexylthio etc.) optionally having 1 to 3 halogen atoms (e.g., fluorine, chlorine, bromine, iodine), (10) $C_{6-14}$ arylthio (e.g., phenylthio, naphthylthio etc.), (11) $C_{7-16}$ aralkylthio (e.g., benzylthio, phenethylthio, diphenylmethylthio, 1-naphthylmethylthio, 2-naphthylmethylthio, 2,2-diphenylethylthio, 3-phenylpropylthio, 4-phenylbutylthio, 5-phenylpentylthio etc.) (12) amino, (13) mono-$C_{1-6}$ alkylamino (e.g., methylamino, ethylamino etc.), (14) mono-$C_{6-14}$ arylamino (e.g., phenylamino, 1-naphthylamino, 2-naphthylamino etc.), (15) mono-$C_{7-16}$ aralkylamino (e.g., benzylamino etc.), (16) di-$C_{1-6}$ alkylamino (e.g., dimethylamino, diethylamino etc.), (17) di-$C_{6-14}$ arylamino (e.g., diphenylamino etc.), (18) di-$C_{7-16}$ aralkylamino (e.g., dibenzylamino etc.), (19) formyl, (20) $C_{1-6}$ alkyl-carbonyl (e.g., acetyl, propionyl etc.), (21) $C_{6-14}$ aryl-carbonyl (e.g., benzoyl, 1-naphthoyl, 2-naphthoyl etc.), (22) carboxyl, (23) $C_{1-6}$ alkoxy-carbonyl (e.g., methoxycarbonyl, ethoxycarbonyl, propoxycarbonyl, tert-butoxycarbonyl etc.), (24) $C_{6-14}$ aryloxy-carbonyl (e.g., phenoxycarbonyl etc.), (25) carbamoyl, (26) thiocarbamoyl, (27) mono-$C_{1-6}$ alkyl-carbamoyl (e.g., methylcarbamoyl, ethylcarbamoyl etc.), (28) di-$C_{1-6}$ alkyl-carbamoyl (e.g., dimethylcarbamoyl, diethylcarbamoyl, ethylmethylcarbamoyl etc.), (29) $C_{6-14}$ aryl-carbamoyl (e.g., phenylcarbamoyl, 1-naphthylcarbamoyl, 2-naphthylcarbamoyl etc.), (30) $C_{1-6}$ alkylsulfonyl (e.g., methylsulfonyl, ethylsulfonyl etc.), (31) $C_{6-14}$ arylsulfonyl (e.g., phenylsulfonyl, 1-naphthylsulfonyl, 2-naphthylsulfonyl etc.), (32) $C_{1-6}$ alkylsulfinyl (e.g., methylsulfinyl, ethylsulfinyl etc.), (33) $C_{6-14}$ arylsulfinyl (e.g., phenylsulfinyl, 1-naphthylsulfinyl, 2-naphthylsulfinyl etc.), (34) formylamino, (35) $C_{1-6}$ alkyl-carbonylamino (e.g., acetylamino etc.), (36) $C_{6-14}$ aryl-carbonylamino (e.g., benzoylamino, naphthoylamino etc.), (37) $C_{1-6}$ alkoxy-carbonylamino (e.g., methoxycarbonylamino, ethoxycarbonylamino, propoxycarbonylamino, butoxycarbonylamino etc.), (38) $C_{1-6}$ alkylsulfonylamino (e.g., methylsulfonylamino, ethylsulfonylamino etc.), (39) $C_{6-14}$ arylsulfonylamino (e.g., phenylsulfonylamino, 2-naphthylsulfonylamino, 1-naphthylsulfonylamino etc.), (40) $C_{1-6}$ alkyl-carbonyloxy (e.g., acetoxy, propionyloxy etc.), (41) $C_{6-14}$ aryl-carbonyloxy (e.g., benzoyloxy, naphthylcarbonyloxy etc.), (42) $C_{1-6}$ alkoxy-carbonyloxy (e.g., methoxycarbonyloxy, ethoxycarbonyloxy, propoxycarbonyloxy, butoxycarbonyloxy etc.), (43) mono-$C_{1-6}$ alkyl-carbamoyloxy (e.g., methylcarbamoyloxy, ethylcarbamoyloxy etc.), (44) di-$C_{1-6}$ alkyl-carbamoyloxy (e.g., dimethylcarbamoyloxy, diethylcarbamoyloxy etc.), (45) $C_{6-14}$ aryl-carbamoyloxy (e.g., phenylcarbamoyloxy, naphthylcarbamoyloxy etc.), (46) a 5- to 7-membered saturated cyclic amino optionally containing, besides one nitrogen atom and carbon atom, 1 or 2 kinds of 1 to 4 hetero atoms selected from a nitrogen atom, a sulfur atom and an oxygen atom (e.g., pyrrolidin-1-yl, piperidino, piperazin-1-yl, morpholino, thiomorpholino, hexahydroazepin-1-yl etc.), (47) a 5- to 10-membered aromatic heterocyclic group containing, besides carbon atom, 1 or 2 kinds of 1 to 4 hetero atoms selected from a nitrogen atom, a sulfur atom and an oxygen atom (e.g., 2-thienyl, 3-thienyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl etc.), (48) $C_{1-3}$ alkylenedioxy (e.g., methylenedioxy, ethylenedioxy etc.), and (49) $C_{3-7}$ cycloalkyl (e.g., cyclopropyl, cyclobutyl, cyclopentyl, cyclohexyl, cycloheptyl etc.) and the like can be mentioned.

The number of the substituents is 1 to 3.

As the "acyl group" for $R^2$, an acyl group having 1 to 20 carbon atoms, which is derived from organic carboxylic acid can be mentioned. For example, $C_{1-7}$ alkanoyl groups (e.g., formyl; $C_{1-6}$ alkyl-carbonyl such as acetyl, propionyl, butyryl, isobutyryl, pentanoyl, hexanoyl, heptanoyl and the like; etc.), $C_{6-14}$ aryl-carbonyl groups (e.g., benzoyl, naphthalenecarbonyl etc.), $C_{1-6}$ alkoxy-carbonyl groups (e.g., methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl etc.), $C_{6-14}$ aryloxy-carbonyl groups (e.g., phenoxycarbonyl group), $C_{7-19}$ aralkyl-carbonyl groups (e.g., phenyl-$C_{1-4}$ alkylcarbonyl such as benzylcarbonyl, phenethylcarbonyl, phenylpropylcarbonyl and the like, benzhydrylcarbonyl, naphthyl-$C_{1-4}$ alkylcarbonyl such as naphthylethylcarbonyl and the like, etc.), $C_{7-19}$ aralkyloxy-carbonyl groups (e.g., phenyl-$C_{1-4}$ alkyloxycarbonyl such as benzyloxycarbonyl and the like, etc.), 5- or 6-membered heterocyclyl-carbonyl group or condensed heterocyclyl-carbonyl groups thereof (e.g., a 5- or 6-membered heterocyclyl-carbonyl group containing 1 to 4 hetero atoms such as nitrogen atom (optionally oxidized), oxygen atom, sulfur atom (optionally mono or dioxidized), e.g., pyrrolylcarbonyl such as 2- or 3-pyrrolylcarbonyl and the like; pyrazolylcarbonyl such as 3-, 4- or 5-pyrazolylcarbonyl and the like; imidazolylcarbonyl such as 2-, 4- or 5-imidazolylcarbonyl and the like; triazolylcarbonyl such as 1,2,3-triazol-4-ylcarbonyl, 1,2,4-triazol-3-ylcarbonyl and the like; tetrazolylcarbonyl such as 1H- or 2H-tetrazol-5-ylcarbonyl and the like; furylcarbonyl such as 2- or 3-furylcarbonyl and the like; thienylcarbonyl such as 2- or 3-thienylcarbonyl and the like; oxazolylcarbonyl such as 2-, 4- or 5-oxazolylcarbonyl and the like; isoxazolylcarbonyl such as 3-, 4- or 5-isoxazolylcarbonyl and the like; oxadiazolylcarbonyl such as 1,2,3-oxadiazol-4- or 5-ylcarbonyl, 1,2,4-oxadiazol-3- or 5-ylcarbonyl, 1,2,5-oxadiazol-3- or 4-ylcarbonyl, 1,3,4-oxadiazol-2-ylcarbonyl and the like; thiazolylcarbonyl such as 2-, 4- or 5-thiazolylcarbonyl and the like; isothiazolylcarbonyl such as 3-, 4- or 5-isothiazolylcarbonyl and the like; thiadiazolylcarbonyl such as 1,2,3-thiadiazol-4- or 5-ylcarbonyl, 1,2,4-thiadiazol-3- or 5-ylcarbonyl, 1,2,5-thiadiazol-3- or 4-ylcarbonyl, 1,3,4-thiadiazol-2-ylcarbonyl and the like; pyrrolidinylcarbonyl such as 2- or 3-pyrrolidinylcarbonyl and the like; pyridylcarbonyl such as 2-, 3- or 4-pyridylcarbonyl and the like; pyridylcarbonyl wherein nitrogen atom is oxidized such as 2-, 3- or 4-pyridyl-N-oxidocarbonyl and the like; pyridazinylcarbonyl such as 3- or 4-pyridazinylcarbonyl and the like; pyridazinylcarbonyl wherein one or both nitrogen atoms are oxidized, such as 3-, 4-, 5- or 6-pyridazinyl-N-oxidocarbonyl and the like; pyrimidinylcarbonyl such as 2-, 4- or 5-pyrimidinylcarbonyl and the like; pyrimidinylcarbonyl wherein one or both nitrogen atoms are oxidized, such as 2-, 4-, 5- or 6-pyrimidinyl-N-oxidocarbonyl and the like; pyrazinylcarbonyl; piperidinylcarbonyl such as 2-, 3- or 4-piperidinylcarbonyl and the like; piperazinylcarbonyl; indolylcarbonyl such as 3H-indol-2- or 3-ylcarbonyl and the like; pyranylcarbonyl such as 2-, 3- or 4-pyranylcarbonyl and the like; thiopyranylcarbonyl such as 2-, 3- or 4-thiopyranylcarbonyl and the like; quinolylcarbonyl such as 3-, 4-, 5-, 6-, 7- or 8-quinolylcarbonyl and the like; isoquinolylcarbonyl; pyrido[2,3-d]pyrimidinylcarbonyl (e.g., pyrido[2,3-d]pyrimidin-2-ylcarbonyl); naphthyridinylcarbonyl such as 1,5-, 1,6-, 1,7-, 1,8-, 2,6- or 2,7-naphthyridinylcarbonyl and the like (e.g., 1,5-naphthyridin-2- or 3-ylcarbonyl); thieno[2,3-d]pyridylcarbonyl (e.g., thieno[2,3-d]pyridin-3-ylcarbonyl); pyrazinoquinolylcarbonyl (e.g., pyrazino[2,3-b]quinolin-2-ylcarbonyl); chromenylcarbonyl (e.g., 2H-chromen-2- or 3-ylcarbonyl etc.) and the like), a 5- or 6-membered heterocyclyl-acetyl group (e.g., 5- or 6-membered heterocyclyl-acetyl group containing 1 to 4 hetero atoms such as nitrogen atom (optionally oxidized), oxygen atom, sulfur atom (optionally mono or dioxidized) and the like), such as 2-pyrrolylacetyl, 3-imidazolylacetyl, 5-isoxazolylacetyl and the like, and the like can be used.

As regards the substituent of acyl group, for example, when the above-mentioned acyl group is an alkanoyl group or alkoxy-carbonyl group, the acyl group is optionally substituted by 1 to 3 alkylthio groups (e.g., $C_{1-4}$ alkylthio such as methylthio, ethylthio, n-propylthio, isopropylthio and the like, and the like), halogen (e.g., fluorine, chlorine, bromine, iodine), alkoxy groups (e.g., $C_{1-6}$ alkoxy such as methoxy, ethoxy, n-propoxy, tert-butoxy, n-hexyloxy and the like, and the like), nitro groups, alkoxy-carbonyl groups (e.g., $C_{1-6}$ alkoxy-carbonyl such as methoxycarbonyl, ethoxycarbonyl, n-propoxycarbonyl, isopropoxycarbonyl, n-butoxycarbonyl, isobutoxycarbonyl, sec-butoxycarbonyl, tert-butoxycarbonyl and the like, and the like), alkylamino groups (e.g., mono- or di-$C_{1-6}$ alkylamino such as methylamino, ethylamino, n-propylamino, n-butylamino, tert-butylamino, n-pentylamino, n-hexylamino, dimethylamino, diethylamino, methylethylamino, di-(n-propyl)amino, di-(n-butyl)amino and the like, and the like), alkoxyimino groups (e.g., $C_{1-6}$ alkoxyimino such as methoxyimino, ethoxyimino, n-propoxyimino, tert-butoxyimino, n-hexyloxy-imino and the like, and the like) or hydroxyimino.

When the above-mentioned acyl group is an aryl-carbonyl group, an aryloxy-carbonyl group, an aralkyl-carbonyl group, an aralkyloxycarbonyl group, a 5- or 6-membered heterocyclyl-carbonyl group or a 5- or 6-membered heterocyclyl-acetyl group, it is optionally substituted by 1 to 5 (preferably 1 to 3) alkyl groups (e.g., $C_{1-6}$ alkyl such as methyl, ethyl, n-propyl, isopropyl, n-butyl, isobutyl, sec-butyl, tert-butyl, n-pentyl, sec-pentyl, isopentyl, neopentyl, n-hexyl, isohexyl and the like, $C_{3-6}$ cycloalkyl such as cyclohexyl and the like, and the like), alkenyl groups (e.g., $C_{2-6}$ alkenyl such as allyl, isopropenyl, isobutenyl, 1-methylallyl, 2-pentenyl, 2-hexenyl and the like, and the like), alkynyl groups (e.g., $C_{2-6}$ alkynyl such as propargyl, 2-butynyl, 3-butynyl, 3-pentynyl, 3-hexynyl and the like, and the like), alkoxy groups (e.g., $C_{1-6}$ alkoxy such as methoxy, ethoxy, n-propoxy, tert-butoxy, n-hexyloxy and the like, and the like), acyl groups [e.g., $C_{1-7}$ alkanoyl such as formyl, acetyl, propionyl, butyryl, isobutyryl, pentanoyl, hexanoyl, heptanoyl and the like; $C_{6-14}$ arylcarbonyl such as benzoyl, naphthalenecarbonyl and the like; $C_{1-6}$ alkoxy-carbonyl such as methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl and the like; $C_{6-14}$ aryloxy-carbonyl such as phenoxycarbonyl and the like; $C_{7-19}$ aralkyl-carbonyl such as phenyl-$C_{1-4}$ alkyl-carbonyl (e.g., benzylcarbonyl, phenethylcarbonyl, phenylpropylcarbonyl and the like) and the like; $C_{7-19}$ aralkyloxy-carbonyl such as phenyl-$C_{1-4}$ alkyloxy-carbonyl (e.g., benzyloxycarbonyl and the like) and the like, and the like], nitro, amino, hydroxy, cyano, sulfamoyl, mercapto, halogen (e.g., fluorine, chlorine, bromine, iodine), or alkylthio groups ($C_{1-4}$ alkylthio such as methylthio, ethylthio, n-propylthio, isobutylthio and the like, and the like).

Examples of the "optionally substituted hydroxy group" for $R^2$ include hydroxy; $C_{1-6}$ alkoxy (e.g., methoxy, ethoxy, propoxy, isopropoxy, butoxy, isobutoxy, sec-butoxy, pentyloxy, hexyloxy, trifluoromethoxy etc.) optionally having 1 to 3 halogen atoms (e.g., fluorine, chlorine, bromine, iodine), $C_{6-14}$ aryloxy (e.g., phenyloxy, naphthyloxy etc.), $C_{7-16}$ aralkyloxy (e.g., benzyloxy, phenethyloxy, diphenylmethyloxy, 1-naphthylmethyloxy, 2-naphthylmethyloxy, 2,2- diphenylethyloxy, 3-phenylpropyloxy, 4-phenylbutyloxy, 5-phenylpentyloxy etc.), $C_{1-6}$ alkyl-carbonyloxy (e.g., acetoxy, propionyloxy etc.), $C_{6-14}$ aryl-carbonyloxy (e.g., benzoyloxy, naphthylcarbonyloxy etc.), $C_{1-6}$ alkoxy-carbonyloxy (e.g., methoxycarbonyloxy, ethoxycarbonyloxy, propoxycarbonyloxy, butoxycarbonyloxy etc.), mono-$C_{1-6}$ alkyl-carbamoyloxy (e.g., methylcarbamoyloxy, ethylcarbamoyloxy etc.), di-$C_{1-6}$ alkyl-carbamoyloxy (e.g., dimethylcarbamoyloxy, diethylcarbamoyloxy etc.), $C_{6-14}$ aryl-carbamoyloxy (e.g., phenylcarbamoyloxy, naphthylcarbamoyloxy etc.), and the like.

Examples of the "optionally substituted amino group" for $R^2$ include amino; mono-$C_{1-6}$ alkylamino (e.g., methylamino, ethylamino etc.); mono-$C_{6-14}$ arylamino (e.g., phenylamino, 1-naphthylamino, 2-naphthylamino etc.); mono-$C_{1-7-16}$ aralkylamino (e.g., benzylamino etc.); di-$C_{1-6}$ alkylamino (e.g., dimethylamino, diethylamino etc.); di-$C_{6-14}$ arylamino (e.g., diphenylamino etc.); di-$C_{7-16}$ aralkylamino (e.g., dibenzylamino etc.); formylamino; $C_{1-6}$ alkyl-carbonylamino (e.g., acetylamino etc.); $C_{6-14}$ aryl-carbonylamino (e.g., benzoylamino, naphthoylamino etc.); $C_{1-6}$ alkoxy-carbonylamino (e.g., methoxycarbonylamino, ethoxycarbonylamino, propoxycarbonylamino, tert-butoxycarbonylamino etc.); $C_{7-16}$ aralkyloxycarbonylamino (e.g., benzyloxycarbonylamino etc.); $C_{1-6}$ alkylsulfonylamino (e.g., methylsulfonylamino, ethylsulfonylamino etc.); $C_{6-14}$ arylsulfonylamino (e.g., phenylsulfonylamino, 2-naphthylsulfonylamino, 1-naphthylsulfonylamino etc.) and the like.

Examples of the "optionally substituted hydrocarbon group" for $R^3$ include groups similar to the "optionally substituted hydrocarbon group" for the aforementioned $R^1$.

Examples of the "optionally substituted heterocyclic group" for $R^3$ include groups similar to the "optionally substituted heterocyclic group" for the aforementioned $R^1$.

Examples of the "leaving group" for X include halogen atoms such as chlorine, bromine and the like, a hydroxy group, a methanesulfonyloxy group, a trifluoromethanesulfonyloxy group, a benzenesulfonyloxy group, a p-toluenesulfonyloxy group, a p-nitrobenzenesulfonyloxy group, an o-nitrobenzenesulfonyloxy group and the like.

Examples of the "alkyl group" for $R^4$ include $C_{1-4}$ alkyl groups such as methyl, ethyl, propyl, isopropyl, butyl, isobutyl, sec-butyl, tert-butyl etc. and the like.

Examples of the "optionally substituted hydrocarbon group" for $R^5$ include groups similar to the "optionally substituted hydrocarbon group" for the aforementioned $R^1$.

Examples of the "optionally substituted heterocyclic group" for $R^5$ include groups similar to the "optionally substituted heterocyclic group" for the aforementioned $R^1$.

Examples of the "acyl group" for $R^5$ include groups similar to the "acyl group" for the aforementioned $R^2$.

Examples of the "optionally substituted hydrocarbon group" for $R^6$ include groups similar to the "optionally substituted hydrocarbon group" for the aforementioned $R^1$.

Examples of the "optionally substituted heterocyclic group" for $R^6$ include groups similar to the "optionally substituted heterocyclic group" for the aforementioned $R^1$.

Examples of the "substituted carboxyl group" for $R^7$ include $C_{1-4}$ alkoxy-carbonyl (e.g., methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl).

Examples of the "optionally substituted hydrocarbon group" for $R^8$ include groups similar to the "optionally substituted hydrocarbon group" for the aforementioned $R^1$.

Examples of the "optionally substituted heterocyclic group" for $R^8$ include groups similar to the "optionally substituted heterocyclic group" for the aforementioned $R^1$.

Examples of the "aryl group" of the "aryl group having substituent(s)" for $R^{1a}$ include $C_{6-14}$ aryl (e.g., phenyl, 1-naphthyl, 2-naphthyl, 2-biphenylyl, 3-biphenylyl, 4-biphenylyl, 2-anthryl etc.) and the like.

Examples of the "substituent" of the aryl group include substituents similar to the substituents optionally present when the "hydrocarbon group" for the above-mentioned $R^1$ is cycloalkyl, aryl or aralkyl. The number of the substituents is 1 to 5, preferably 1 to 3.

Examples of the "optionally substituted hydrocarbon group" for $R^{1b}$ include groups similar to the "optionally substituted hydrocarbon group" for the aforementioned $R^1$.

Examples of the "optionally substituted heterocyclic group" for $R^{1b}$ include groups similar to the "optionally substituted heterocyclic group" for the aforementioned $R^1$.

As $R^3$, a "nitrogen-containing monocyclic heterocyclic group optionally condensed with a benzene ring or a heterocycle (as the heterocyclic group, groups similar to the heterocyclic group of the "optionally substituted heterocyclic group" for the aforementioned $R^1$ can be mentioned)" (e.g., 5- or 6-membered aromatic nitrogen-containing monocyclic heterocyclic groups such as thiazolyl, imidazolyl, pyrazolyl, pyridyl, pyrimidinyl, pyridazinyl, pyrazinyl and the like, and the like) optionally substituted by 1 to 3 substituents selected from (i) halogen (e.g., fluorine, chlorine, bromine, iodine), (ii) hydroxy, (iii) cyano, (iv) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogens (e.g., fluorine, chlorine, bromine, iodine), (v) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1 to 5 (preferably 1 to 3) halogens (e.g., fluorine, chlorine, bromine, iodine), (vi) amino group optionally substituted by $C_{1-6}$ alkyl (e.g., methyl, ethyl, propyl, isopropyl, butyl, isobutyl, sec-butyl, tert-butyl, pentyl, hexyl etc.), (vii) oxo and (viii) $C_{1-6}$ alkoxy-carbonyl (e.g., methoxycarbonyl, ethoxycarbonyl, propoxycarbonyl, tert-butoxycarbonyl etc.) is preferable.

As $R^3$, particularly, a 6-membered nitrogen-containing aromatic heterocyclic group (e.g., pyridyl groups (e.g., 2-, 3- or 4-pyridyl etc.), pyrimidinyl groups (e.g., 2-, 4- or 5-pyrimidinyl etc.), pyridazinyl groups (e.g., 3- or 4-pyridazinyl etc.) etc.) optionally substituted by 1 to 3 substituents selected from (i) halogen (e.g., fluorine, chlorine, bromine, iodine), (ii) hydroxy, (iii) cyano, (iv) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogens (e.g., fluorine, chlorine, bromine, iodine), (v) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1 to 5 (preferably 1 to 3) halogens (e.g., fluorine, chlorine, bromine, iodine) and (vi) an amino group optionally substituted by $C_{1-6}$ alkyl (e.g., methyl, ethyl, propyl, isopropyl, butyl, isobutyl, sec-butyl, tert-butyl, pentyl, hexyl etc.) is preferable, and a pyridyl group optionally substituted by 1 to 3 substituents selected from (i) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogens (e.g., fluorine, chlorine, bromine, iodine) and (ii) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1 to 5 (preferably 1 to 3) halogens (e.g., fluorine, chlorine, bromine, iodine) is particularly preferable. As $R^3$, a pyridyl group is particularly preferable.

As $R^1$, [1] a $C_{6-14}$ aryl group (e.g., phenyl group) optionally substituted by 1 to 5 (preferably 1 to 3) substituents selected from (i) a halogen atom (e.g., fluorine, chlorine, bromine, iodine), (ii) cyano, (iii) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogens (e.g., fluorine, chlorine, bromine, iodine), (iv) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1 to 5 (preferably 1 to 3) halogens (e.g., fluorine, chlorine, bromine, iodine), (v) acetyl, (vi) $C_{3-7}$ cycloalkyl (e.g., cyclopropyl, cyclobutyl, cyclopentyl, cyclohexyl, cycloheptyl etc.), (vii) $C_{1-6}$ alkylsulfonyl (e.g., methylsulfonyl, ethylsulfonyl etc.), (viii) a $C_{1-6}$ alkyl group substituted by 1 to 3 hydroxy (e.g., hydroxymethyl, hydroxyethyl etc.), (ix) $C_{1-6}$ alkylthio (e.g., methylthio, ethylthio, propylthio, isopropylthio, butylthio, isobutylthio, sec-butylthio, pentylthio, hexylthio etc.) optionally substituted by 1 to 5 (preferably 1 to 3) halogens (e.g., fluorine, chlorine, bromine, iodine) and (x) $C_{1-6}$ alkylsulfinyl (e.g., methylsulfinyl, ethylsulfinyl etc.),

[2] a thienyl group optionally substituted by 1 to 3 substituents selected from (i) a halogen atom (e.g., fluorine, chlorine, bromine, iodine), (ii) cyano, (iii) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogens (e.g., fluorine, chlorine, bromine, iodine), (iv) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1 to 5 (preferably 1 to 3) halogens (e.g., fluorine, chlorine, bromine, iodine) and (v) acetyl, or

[3] a pyridyl group optionally substituted by 1 to 4 substituents selected from (i) a halogen atom (e.g., fluorine, chlorine, bromine, iodine), (ii) cyano, (iii) lower (specifically $C_{1-6}$) alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogens (e.g., fluorine, chlorine, bromine, iodine), (iv) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1 to 5 (preferably 1 to 3) halogens (e.g., fluorine, chlorine, bromine, iodine), (v) acyl (e.g., acetyl), (vi) nitro and (vii) amino is preferable.

Of these, as $R^1$, [1] a $C_{6-14}$ aryl group (e.g., phenyl group) optionally substituted by 1 to 5 (preferably 1 to 3) substituents selected from (i) a halogen atom (e.g., fluorine, chlorine, bromine, iodine), (ii) cyano, (iii) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogens (e.g., fluorine, chlorine, bromine, iodine), (iv) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1 to 5 (preferably 1 to 3) halogens (e.g., fluorine, chlorine, bromine, iodine) and (v) acetyl,

[2] a thienyl group optionally substituted by 1 to 3 substituents selected from (i) a halogen atom (e.g., fluorine, chlorine, bromine, iodine), (ii) cyano, (iii) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogens (e.g., fluorine, chlorine, bromine, iodine), (iv) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1 to 5 (preferably 1 to 3) halogens (e.g., fluorine, chlorine, bromine, iodine) and (v) acetyl, or

[3] a pyridyl group optionally substituted by 1 to 4 substituents selected from (i) a halogen atom (e.g., fluorine, chlorine, bromine, iodine), (ii) cyano, (iii) lower (specifically $C_{1-6}$) alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogens (e.g., fluorine, chlorine, bromine, iodine), (iv) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1 to 5 (preferably 1 to 3) halogens (e.g., fluorine, chlorine, bromine, iodine), (v) acyl (e.g., acetyl), (vi) nitro and (vii) amino is preferable.

Particularly, [1] a phenyl group optionally substituted by 1 to 5 (preferably 1 to 3) substituents selected from (i) a halogen atom (e.g., fluorine, chlorine, bromine, iodine) and (ii) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogens (e.g., fluorine, chlorine, bromine, iodine),

[2] a thienyl group optionally substituted by 1 to 3 substituents selected from (i) a halogen atom (e.g., fluorine, chlorine, bromine, iodine) and (ii) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogens (e.g., fluorine, chlorine, bromine, iodine), or

[3] a pyridyl group optionally substituted by 1 to 4 substituents selected from (i) a halogen atom (e.g., fluorine, chlorine, bromine, iodine) and (ii) lower (specifically $C_{1-6}$) alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogens (e.g., fluorine, chlorine, bromine, iodine) is preferable.

Of those mentioned above, a preferable embodiment of $R^1$ include [1] a phenyl group optionally substituted by 1 to 5 substituents selected from (i) a halogen atom and (ii) $C_{1-6}$ alkyl optionally substituted by 1 to 5 halogen atoms, [2] a pyridyl group optionally substituted by 1 to 4 substituents selected from lower ($C_{1-6}$) alkyl, a halogen atom, alkoxy ($C_{1-6}$ alkoxy), cyano, acyl (e.g., acetyl), nitro and amino, and the like.

As $R^1$, a phenyl group, a 2-fluorophenyl group, a 2-methylphenyl group, a 2-fluoropyridin-3-yl group, a 3-fluoropyridin-4-yl group, a 2-chloropyridin-3-yl group, a 6-chloropyridin-3-yl group, a 4-methylpyridin-3-yl group, a 2-methylpyridin-3-yl group, a 3-methylpyridin-2-yl group, a 2-trifluoromethylpyridin-3-yl group and a 6'-chloro-2,3'-bipyridin-5-yl group are particularly preferable.

Preferably, $R^2$ is a hydrogen atom, a $C_{1-6}$ alkyl group (e.g., methyl, ethyl, n-propyl, isobutyl etc.), a $C_{1-6}$ alkyl-carbonyl group (e.g., acetyl, propionyl, butyryl, isobutyryl, pentanoyl, hexanoyl, heptanoyl etc.), a fluorine atom or a chlorine atom, and a hydrogen atom is particularly preferable.

As $R^4$, methyl or ethyl is preferable, and methyl is particularly preferable.

The above-mentioned preferable embodiments of the substituents for $R^1$ to $R^4$ may be optionally combined to achieve a preferable embodiment.

In a preferable embodiment, for example, $R^3$ is a 5- or 6-membered aromatic nitrogen-containing monocyclic heterocyclic group (e.g., thiazolyl, imidazolyl, pyrazolyl, pyridyl, pyrimidinyl, pyridazinyl, pyrazinyl and the like) or an imidazo[1,2-a]pyrimidinyl group, which are optionally substituted by 1 to 3 substituents selected from (i) halogen (e.g., fluorine, chlorine, bromine, iodine), (ii) hydroxy, (iii) cyano, (iv) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogens (e.g., fluorine, chlorine, bromine, iodine), (v) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1 to 5 (preferably 1 to 3) halogens (e.g., fluorine, chlorine, bromine, iodine), (vi) amino group optionally substituted by $C_{1-6}$ alkyl (e.g., methyl, ethyl, propyl, isopropyl, butyl, isobutyl, sec-butyl, tert-butyl, pentyl, hexyl etc.) and (vii) $C_{1-6}$ alkoxy-carbonyl (e.g., methoxycarbonyl, ethoxycarbonyl, propoxycarbonyl, tert-butoxycarbonyl etc.);

$R^1$ is [1] a $C_{6-14}$ aryl group (e.g., phenyl group) optionally substituted by 1 to 5 (preferably 1 to 3) substituents selected from (i) a halogen atom (e.g., fluorine, chlorine, bromine, iodine), (ii) cyano, (iii) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogens (e.g., fluorine, chlorine, bromine, iodine), (iv) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1 to 5 (preferably 1 to 3) halogens (e.g., fluorine, chlorine, bromine, iodine), (v) acetyl, (vi) $C_{3-7}$ cycloalkyl (e.g., cyclopropyl, cyclobutyl, cyclopentyl, cyclohexyl, cycloheptyl etc.), (vii) $C_{1-6}$ alkylsulfonyl (e.g., methylsulfonyl, ethylsulfonyl etc.), (viii) a $C_{1-6}$ alkyl group substituted by 1 to 3 hydroxy (e.g., hydroxymethyl, hydroxyethyl etc.), (ix) $C_{1-6}$ alkylthio (e.g., methylthio, ethylthio, propylthio, isopropylthio, butylthio, isobutylthio, sec-butylthio, pentylthio, hexylthio etc.) optionally substituted by 1 to 5 (preferably 1 to 3) halogens (e.g., fluorine, chlorine, bromine, iodine) and (x) $C_{1-6}$ alkylsulfinyl (e.g., methylsulfinyl, ethylsulfinyl etc.),

[2] a thienyl group optionally substituted by 1 to 3 substituents selected from (i) a halogen atom (e.g., fluorine, chlorine, bromine, iodine), (ii) cyano, (iii) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogens (e.g., fluorine, chlorine, bromine, iodine), (iv) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1 to 5 (preferably 1 to 3) halogens (e.g., fluorine, chlorine, bromine, iodine) and (v) acetyl,

[3] a pyridyl group optionally substituted by 1 to 4 substituents selected from (i) a halogen atom (e.g., fluorine, chlorine, bromine, iodine), (ii) cyano, (iii) lower (specifically $C_{1-6}$) alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogens (e.g., fluorine, chlorine, bromine, iodine), (iv) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1 to 5 (preferably 1 to 3) halogens (e.g., fluorine, chlorine, bromine, iodine), (v) acyl (e.g., acetyl), (vi) nitro and (vii) amino, or

[4] a bipyridyl group optionally substituted by 1 to 3 halogen atoms (e.g., fluorine, chlorine, bromine, iodine);

$R^2$ is a hydrogen atom, a $C_{1-6}$ alkyl group (e.g., methyl, ethyl, n-propyl, isobutyl etc.), a $C_{1-6}$ alkyl-carbonyl group (e.g., acetyl, propionyl, butyryl, isobutyryl, pentanoyl, hexanoyl, heptanoyl etc.), a fluorine atom or a chlorine atom, and $R^4$ is methyl or ethyl is preferable, In a particularly preferable embodiment, $R^3$ is a pyridyl group optionally substituted by 1 to 3 substituents selected from (i) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogens (e.g., fluorine, chlorine, bromine, iodine) and (ii) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1 to 5 (preferably 1 to 3) halogens (e.g., fluorine, chlorine, bromine, iodine), $R^1$ is [1] a phenyl group optionally substituted by 1 to 5 (preferably 1 to 3) substituents selected from (i) a halogen atom (e.g., fluorine, chlorine, bromine, iodine) and (ii) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogens (e.g., fluorine, chlorine, bromine, iodine),

[2] a thienyl group optionally substituted by 1 to 3 substituents selected from (i) a halogen atom (e.g., fluorine, chlorine, bromine, iodine) and (ii) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogens (e.g., fluorine, chlorine, bromine, iodine), or

[3] a pyridyl group optionally substituted by 1 to 4 substituents selected from (i) a halogen atom (e.g., fluorine, chlorine, bromine, iodine) and (ii) lower (specifically $C_{1-6}$) alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogens (e.g., fluorine, chlorine, bromine, iodine), and $R^2$ is a hydrogen atom, and $R^4$ is methyl.

As the halogen atom for $X_1$, chlorine or bromine is preferable, and chlorine is more preferable.

As the leaving group for X, a halogen atom such as chlorine, bromine or the like or a hydroxy group is preferable, and a halogen atom is more preferable.

As the "optionally substituted hydrocarbon group" and "optionally substituted heterocyclic group" for $R^5$, substituents similar to the "optionally substituted hydrocarbon group" and "optionally substituted heterocyclic group" for the aforementioned $R^1$ are used. Of these,

[1] an optionally substituted $C_{1-6}$ alkyl group (e.g., methyl, ethyl, propyl, isopropyl, butyl, isobutyl, sec-butyl, tert-butyl, pentyl, hexyl etc.),

[2] an optionally substituted $C_{6-14}$ aryl group (e.g., phenyl, 1-naphthyl, 2-naphthyl, 2-biphenylyl, 3-biphenylyl, 4-biphenylyl, 2-anthryl etc.), or

[3] an optionally substituted 5- to 10-membered aromatic heterocyclic group containing, besides carbon atom, 1 or 2 kinds of 1 to 4 hetero atoms selected from a nitrogen atom, a sulfur atom or an oxygen atom (e.g., 2-furyl, 3-furyl, 2-thienyl, 3-thienyl, 2-imidazolyl, 4-imidazolyl, 3-pyrazolyl, 4-pyrazolyl, 2-oxazolyl, 4-oxazolyl, 5-oxazolyl, 2-thiazolyl, 4-thiazolyl, 5-thiazolyl, 3-isoxazolyl, 4-isoxazolyl, 5-isoxazolyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, 1-indolyl, 2-indolyl, 3-indolyl, 2-benzo[b]furanyl, 3-benzo[b]furanyl etc.) is preferably used.

As the "acyl group" for $R^5$, substituents similar to the "acyl group" for the aforementioned $R^2$ are used. Of these,

[1] an optionally substituted $C_{1-6}$ alkoxy-carbonyl group (e.g., methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl etc.),

[2] an optionally substituted $C_{6-14}$ aryl-carbonyl group (e.g., benzoyl, naphthalenecarbonyl etc.),

[3] an optionally substituted 5- or 6-membered heterocyclylcarbonyl group or a condensed heterocyclyl-carbonyl group thereof (e.g., pyrazolylcarbonyl such as 3-, 4- or 5-pyrazolylcarbonyl and the like; imidazolylcarbonyl such as 2-, 4- or 5-imidazolylcarbonyl and the like; triazolylcarbonyl such as 1,2,3-triazol-4-ylcarbonyl, 1,2,4-triazol-3-ylcarbonyl and the like; tetrazolylcarbonyl such as 1H- or 2H-tetrazol-5-ylcarbonyl and the like; furylcarbonyl such as 2- or 3-furylcarbonyl and the like; thienylcarbonyl such as 2- or 3-thienylcarbonyl and the like; oxazolylcarbonyl such as 2-, 4- or 5-oxazolylcarbonyl and the like; isoxazolylcarbonyl such as 3-, 4- or 5-isoxazolylcarbonyl and the like; oxadiazolylcarbonyl such as 1,2,3-oxadiazol-4- or 5-ylcarbonyl, 1,2,4-oxadiazol-3- or 5-ylcarbonyl, 1,2,5-oxadiazol-3- or 4-ylcarbonyl, 1,3,4-oxadiazol-2-ylcarbonyl and the like; thiazolylcarbonyl such as 2-, 4- or 5-thiazolylcarbonyl and the like; isothiazolylcarbonyl such as 3-, 4- or 5-isothiazolylcarbonyl and the like; thiadiazolylcarbonyl such as 1,2,3-thiadiazol-4- or 5-ylcarbonyl, 1,2,4-thiadiazol-3- or 5-ylcarbonyl, 1,2,5-thiadiazol-3- or 4-ylcarbonyl, 1,3,4-thiadiazol-2-ylcarbonyl and the like; pyrrolidinylcarbonyl such as 2- or 3-pyrrolidinylcarbonyl and the like; pyridylcarbonyl such as 2-, 3- or 4-pyridylcarbonyl and the like; pyridylcarbonyl wherein nitrogen atom is oxidized such as 2-, 3- or 4-pyridyl-N-oxidocarbonyl and the like, or

[4] an optionally substituted $C_{1-7}$ alkanoyl group (e.g., formyl; $C_{1-6}$ alkyl-carbonylacetyl such as propionyl, butyryl, isobutyryl, pentanoyl, hexanoyl, heptanoyl and the like, etc.) is preferable.

Particularly, as the "acyl group" for $R^5$, the above-mentioned [1], [2] or [3] is preferable.

In addition, as $R^5$, a group represented by —S—$R^6$ wherein $R^6$ is as defined above can be mentioned. As $R^6$,

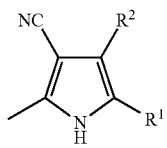

wherein the symbols in the formula are as defined above, is preferable, and

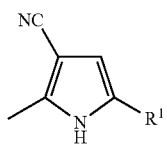

wherein the symbols in the formula are as defined above, is more preferable.

As $R^5$, a $C_{6-14}$ aryl-carbonyl group (e.g., benzoyl) is particularly preferable.

As n, 0 is preferable.

As m, 1 is preferable.

As $R^7$, a cyano group or a $C_{1-4}$ alkoxy-carbonyl group (e.g., methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl) is preferable, and a cyano group is more preferable.

As $R^8$, a hydrogen atom, a $C_{1-6}$ alkyl group (e.g., methyl, ethyl, n-propyl, isobutyl etc.), a $C_{1-6}$ alkyl-carbonyl group (e.g., acetyl, propionyl, butyryl, isobutyryl, pentanoyl, hexanoyl, heptanoyl etc.), a fluorine atom or a chlorine atom is preferable.

As $R^{1a}$, a phenyl group having 1 to 5 (preferably 1 to 3) substituents selected from (i) a halogen atom (e.g., fluorine, chlorine, bromine, iodine) or (ii) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogens (e.g., fluorine, chlorine, bromine, iodine) is preferable.

As $R^{1b}$, the "optionally substituted hydrocarbon group" and "optionally substituted heterocyclic group" used for the aforementioned $R^1$ can be mentioned. Of these, an optionally substituted $C_{6-14}$ aryl group (e.g., phenyl, 1-naphthyl, 2-naphthyl), an optionally substituted 3- to 8-membered heterocyclic group (e.g., thienyl, pyridyl) or an optionally substituted $C_{1-6}$ alkyl group (e.g., methyl) is preferable.

More preferable examples of $R^{1b}$ include

[1] a phenyl group optionally substituted by 1 to 5 (preferably 1 to 3) substituents selected from (i) a halogen atom (e.g., fluorine, chlorine, bromine, iodine) and (ii) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogens (e.g., fluorine, chlorine, bromine, iodine),

[2] a thienyl group optionally substituted by 1 to 3 substituents selected from (i) a halogen atom (e.g., fluorine, chlorine, bromine, iodine) and (ii) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogens (e.g., fluorine, chlorine, bromine, iodine), or

[3] a pyridyl group optionally substituted by 1 to 4 substituents selected from (i) a halogen atom (e.g., fluorine, chlorine, bromine, iodine) and (ii) lower (specifically $C_{1-6}$) alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogens (e.g., fluorine, chlorine, bromine, iodine) is preferable.

Preferable examples of compound (VIII), which is an object compound, include

1-{5-(2-fluorophenyl)-1-[(6-methylpyridin-3-yl)sulfonyl]-1H-pyrrol-3-yl}-N-methylmethanamine or a salt thereof, 1-[4-fluoro-5-phenyl-1-(pyridin-3-ylsulfonyl)-1H-pyrrol-3-yl]-N-methylmethanamine or a salt thereof, N-methyl-1-[5-(4-methyl-3-thienyl)-1-(pyridin-3-ylsulfonyl)-1H-pyrrol-3-yl]methanamine or a salt thereof, 1-[5-(2-fluoropyridin-3-yl)-1-(pyridin-3-ylsulfonyl)-1H-pyrrol-3-yl]-N-methylmethanamine or a salt thereof, 1-[5-(2-fluorophenyl)-1-(pyridin-3-ylsulfonyl)-1H-pyrrol-3-yl]-N-methylmethanamine or a salt thereof, N-methyl-1-[5-(2-methylphenyl)-1-(pyridin-3-ylsulfonyl)-1H-pyrrol-3-yl]methanamine or a salt thereof, and the like.

The production method of the present invention is explained in detail in the following.

As salts of compounds (I)-(XVII) in reaction wherein metal salt, ammonium salt, salts with organic bases, salts with inorganic bases, salts with organic acids, salts with basic or acidic amino acids and the like can be mentioned. Preferable examples of metal salt include alkali metal salts such as sodium salt, potassium salt and the like; alkaline earth metal salts such as calcium salt, magnesium salt, barium salt and the like; aluminum salt and the like. Preferable examples of the salt with organic base include a salt with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. Preferable examples of the salt with inorganic acid include a salt with hydrochloric acid, hydrobromic acid, nitric acid, sulfuric acid, phosphoric acid and the like. Preferable examples of the salt with organic acid include a salt with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of the salt with basic amino acid include a salt with arginine, lysine, ornithine and the like. Preferable examples of the salt with acidic amino acid include a salt with aspartic acid, glutamic acid and the like.

While the compounds obtained in respective steps can be used for the next reaction in the form of a reaction mixture or a crude product, they can also be easily isolated and purified from the reaction mixture by a known separation and purification means, such as recrystallization, distillation, chromatography and the like.

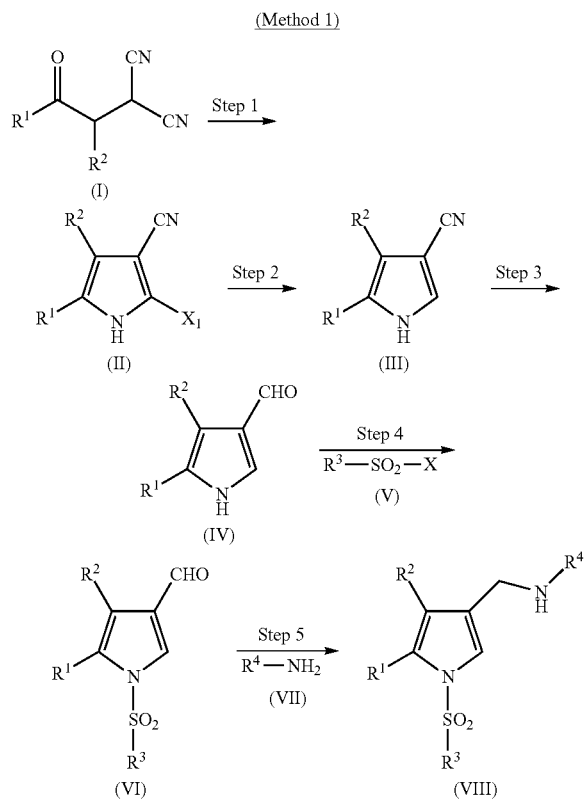

wherein each symbol is as defined above.

Step 1

Compound (II) or a salt thereof can be produced by cyclizing compound (I) or a salt thereof in the presence of hydrogen halide.

This reaction can be performed according to the method described in JP-A-6-9554 and the like, or a method analogous thereto.

Compound (I) or a salt thereof can be produced according to, for example, the method described in JP-A-6-9554 and the like, or a method analogous thereto.

Step 2

Compound (III) or a salt thereof can be produced by subjecting compound (II) or a salt thereof to dehalogenation.

As the dehalogenation, a method of catalytic hydrogenation can be mentioned.

The catalytic hydrogenation can be performed in the presence of a hydrogen source and a metal catalyst. Examples of the metal catalyst include palladium catalyst (e.g., palladium carbon, palladium hydroxide carbon, palladium oxide and the like), nickel catalyst (e.g., Raney-nickel and the like), platinum catalyst (e.g., platinum oxide, platinum carbon and the like), rhodium catalyst (e.g., rhodium carbon and the like), cobalt catalyst (e.g., Raney-cobalt and the like) and the like. Of these, palladium carbon or Raney-nickel is preferable. The amount of the metal catalyst to be used is about 0.001 to about 10 mol, preferably about 0.001 to about 5 mol, per 1 mol of compound (II).

Examples of the hydrogen source include hydrogen gas, formic acid, ammonium formate, triethylammonium formate, sodium phosphinate, hydrazine and the like. When a hydrogen source other than hydrogen gas is used, a compound of a hydrogen source is used in about 1 to about 10 mol, preferably about 1 to about 5 mol, per 1 mol of compound (II).

The dehalogenation is preferably performed in the presence of a base. As the base, for example, inorganic bases such as sodium hydride, sodium hydroxide, potassium hydroxide and the like, basic salts such as sodium carbonate, potassium carbonate, cesium carbonate, sodium hydrogen carbonate and the like, metal bases such as potassium ethoxide, potassium tert-butoxide, sodium methoxide, sodium ethoxide and the like, aromatic amines such as pyridine, lutidine and the like, tertiary amines such as diisopropylethylamine, triethylamine, tripropylamine, tributylamine, cyclohexyldimethylamine, 4-N,N-dimethylaminopyridine, N,N-dimethylaniline, N-methylpiperidine, N-methylpyrrolidine, N-methylmorpholine and the like, and the like can be mentioned. Preferred are tertiary amines such as diisopropylethylamine and the like. The amount of the base to be used is about 1 to about 10 mol, preferably about 1 to about 5 mol, per 1 mol of compound (II).

The dehalogenation is generally performed in a solvent inert to the reaction. Examples of such solvent include alcohols (e.g., methanol, ethanol, propanol, butanol and the like), hydrocarbons (e.g., benzene, toluene, xylene and the like), halogenated hydrocarbons (e.g., dichloromethane, chloroform and the like), ethers (e.g., diethyl ether, dioxane, tetrahydrofuran and the like), esters (e.g., ethyl acetate and the like), amides (e.g., N,N-dimethylformamide, N,N-dimethylacetamide and the like), carboxylic acids (e.g., acetic acid and the like), water and a mixture thereof. The amount of the solvent to be used is generally about 1 to about 100 ml, preferably about 1 to about 50 ml, per 1 g of compound (II).

The hydrogen pressure under which the reaction is performed is generally about 0 to about 10 atm, preferably about 0 to about 5 atm. The reaction temperature is generally about −50° C. to about 100° C., preferably about −20° C. to about 50° C. The reaction time is generally about 0.5 to about 24 hr, preferably about 0.5 to about 10 hr.

Step 3

Compound (IV) or a salt thereof can be produced by reducing compound (III) or a salt thereof and hydrolyzing the reduced product.

As the reduction, a method using metal hydride and a method using catalytic hydrogenation can be mentioned.

Examples of the metal hydride include boron reagent (e.g., sodium borohydride, lithium borohydride, zinc borohydride, sodium cyanoborohydride, sodium triacetoxyborohydride, lithium cyanoborohydride and the like), aluminum reagent (e.g., diisobutylaluminum hydride, aluminum hydride, lithium aluminum hydride and the like), borane complex (e.g., borane-THF complex, borane-dimethylsulfide, borane-pyridine and the like), catechol borane and the like. The amount of the metal hydride to be used is, for example, about 0.2 to about 10 mol, preferably about 0.2 to about 5 mol, per 1 mol of compound (III).

The reduction reaction by metal hydride is generally performed in a solvent inert to the reaction. Examples of such solvent include aromatic hydrocarbons (e.g., toluene, xylene, chlorobenzene and the like), aliphatic hydrocarbons (e.g., heptane, hexane and the like), halogenated hydrocarbons (e.g., chloroform, dichloromethane and the like), ethers (e.g., diethyl ether, tetrahydrofuran, dioxane and the like), and a mixture thereof. The amount of the solvent to be used is generally about 1 to about 100 ml, preferably about 1 to about 50 ml, per 1 g of compound (III).

The reaction temperature is generally about −100° C. to about 100° C., preferably about −70° C. to about 50° C. The reaction time is generally about 0.5 to about 24 hr, preferably about 0.5 hr to about 5 hr.

The catalytic hydrogenation can be performed in the presence of a hydrogen source and a metal catalyst. Examples of the metal catalyst include palladium catalyst (e.g., palladium carbon, palladium hydroxide carbon, palladium oxide and the like), nickel catalyst (e.g., Raney-nickel and the like), platinum catalyst (e.g., platinum oxide, platinum carbon and the like), rhodium catalyst (e.g., rhodium carbon and the like) and the like. Of these, palladium carbon or Raney-nickel is preferable. The amount of the metal catalyst to be used is about 0.0001 to about 10 mol, preferably about 0.001 to about 5 mol, per 1 mol of compound (III), or about 0.1 g to about 10 g, preferably about 0.3 g to about 5 g, per 1 g of compound (III).

Examples of the hydrogen source include hydrogen gas, formic acid, ammonium formate, triethylammonium formate, sodium phosphinate, hydrazine and the like. When a hydrogen source other than hydrogen gas is used, a compound of a hydrogen source is used in about 1 to about 100 mol, preferably about 1 to about 50 mol, more preferably about 1 to about 10 mol, for example, about 1 to about 5 mol, per 1 mol of compound (III).

The catalytic hydrogenation is generally performed in a solvent inert to the reaction. Examples of such solvent include alcohols (e.g., methanol, ethanol, propanol, butanol and the like), aromatic hydrocarbons (e.g., benzene, toluene, xylene, chlorobenzene and the like), halogenated hydrocarbons (e.g., dichloromethane, chloroform and the like), ethers (e.g., diethyl ether, dioxane, tetrahydrofuran and the like), esters (e.g., ethyl acetate and the like), amides (e.g., N,N-dimethylformamide, N,N-dimethylacetamide and the like), carboxylic acids (e.g., acetic acid and the like), water and a mixture thereof. The amount of the solvent to be used is generally about 1 to about 1000 ml, preferably about 1 to about 100 ml, per 1 g of compound (III).

The hydrogen pressure under which the reaction is performed is generally about 0 to about 10 atm, preferably about 0 to about 5 atm. The reaction temperature is generally about −50° C. to about 100° C., preferably about −20° C. to about 50° C. The reaction time is generally about 1 to about 100 hr, preferably about 1 to about 24 hr, for example, about 1 to about 10 hr.

The hydrolysis can be performed in the presence of an acid or a base. Examples of the acid include inorganic acid (hydrochloric acid, sulfuric acid, nitric acid, phosphoric acid, boric acid and the like), organic carboxylic acid (formic acid, acetic acid, propionic acid and the like), organic sulfonic acid (methanesulfonic acid, benzenesulfonic acid, p-toluenesulfonic acid, trifluoromethanesulfonic acid and the like) and the like. The amount of the acid to be used is about 0.1 to about 10 mol, preferably about 0.1 to about 5 mol, per 1 mol of compound (III). Examples of the base include inorganic bases such as sodium hydroxide, potassium hydroxide and the like, basic salts such as sodium carbonate, potassium carbonate, cesium carbonate, sodium hydrogen carbonate etc., and the like. The amount of the base to be used is about 0.1 to about 10 mol, preferably about 0.1 to about 5 mol, per 1 mol of compound (III).

The hydrolysis is advantageously performed using a solvent inert to the reaction. While such solvent is not particularly limited as long as the reaction proceeds, alcohols (e.g., methanol, ethanol, propanol, butanol and the like), aromatic hydrocarbons (e.g., benzene, toluene, xylene, chlorobenzene and the like), halogenated hydrocarbons (e.g., dichloromethane, chloroform and the like), ethers (e.g., diethyl ether, dioxane, tetrahydrofuran and the like), amides (e.g., N,N-dimethylformamide, N,N-dimethylacetamide and the like), carboxylic acids (e.g., acetic acid and the like), water and a mixture thereof can be mentioned. The amount of the solvent to be used is generally about 1 to about 100 ml, preferably about 1 to about 50 ml, per 1 g of compound (III).

The reaction temperature is generally about −20° C. to about 100° C., preferably about 0° C. to about 50° C. The reaction time is generally about 1 to about 48 hr, preferably about 1 to about 24 hr.

Step 4

Compound (VI) or a salt thereof can be produced by subjecting compound (IV) or a salt thereof to a reaction with compound (V) or a salt thereof.

The amount of compound (V) to be used is preferably about 1 to about 10 mol, more preferably about 1 to about 5 mol, per 1 mol of compound (IV).

This reaction is advantageously performed using a solvent inert to the reaction. While such solvent is not particularly limited as long as the reaction proceeds, alcohols (e.g., methanol, ethanol, propanol, butanol and the like), aromatic hydrocarbons (e.g., benzene, toluene, xylene, chlorobenzene and the like), halogenated hydrocarbons (e.g., dichloromethane, chloroform and the like), ethers (e.g., diethyl ether, dioxane, tetrahydrofuran and the like), esters (e.g., ethyl acetate and the like), amides (e.g., N,N-dimethylformamide, N,N-dimethylacetamide and the like), acid nitriles (e.g., acetonitrile, propionitrile and the like), water and a mixture thereof can be mentioned. The amount of the solvent to be used is generally 1 to 100 ml, preferably 1 to 50 ml, per 1 g of compound (IV).

This reaction is preferably performed in the presence of a base. Examples of the base include inorganic bases such as sodium hydride, sodium hydroxide, potassium hydroxide and the like, basic salts such as sodium carbonate, potassium carbonate, cesium carbonate, sodium hydrogen carbonate and the like, metal bases such as potassium ethoxide, potassium tert-butoxide, sodium methoxide, sodium ethoxide and the like, aromatic amines such as pyridine, lutidine and the like, tertiary amines such as diisopropylethylamine, triethylamine, tripropylamine, tributylamine, cyclohexyldimethylamine, 4-N,N-dimethylaminopyridine, N,N-dimethylaniline, N-methylpiperidine, N-methylpyrrolidine, N-methylmorpholine and the like, and a mixture thereof and the like. The amount of the base to be used is about 0.01 to about 10 mol, preferably about 0.1 to about 5 mol, per 1 mol of compound (IV).

The reaction can also be carried out in the co-presence of crown ether. As the crown ether, for example, 15-crown-5-ether, 18-crown-6-ether and the like can be mentioned. The amount of the crown ether to be used is about 1 to about 10 mol, preferably about 1 to about 5 mol, per 1 mol of compound (IV).

The reaction time is generally about 30 min to about 24 hr, preferably about 30 min to about 8 hr. The reaction temperature is generally about 0° C. to about 100° C., preferably about 10° C. to about 50° C.

Step 5

Compound (VIII) or a salt thereof can be produced by reacting compound (VI) or a salt thereof with compound (VII) or a salt thereof, and reducing the imine formed. Alternatively, compound (VIII) or a salt thereof can be produced without isolating the imine formed by performing the reaction of compound (VI) or a salt thereof with compound (VII) or a salt thereof in the presence of a reducing agent.

This reaction can be performed according to the conventional reaction conditions known as reductive amination reaction. For example, the reaction can be performed according to the method described in Jikken Kagaku Koza (Courses in Experimental Chemistry), vol. 14-III, pages 1380-1385 (Maruzen Co., Ltd.).

The amount of compound (VII) to be used is preferably about 1 to about 10 mol, more preferably about 1 to about 5 mol, per 1 mol of compound (VI).

This reaction is advantageously carried out using a solvent inert to the reaction. While the solvent is not particularly limited as long as the reaction proceeds, and alcohols (e.g., methanol, ethanol, propanol, butanol and the like), aromatic hydrocarbons (e.g., benzene, toluene, xylene, chlorobenzene and the like), halogenated hydrocarbons (e.g., dichloromethane, chloroform and the like), ethers (e.g., diethyl ether, dioxane, tetrahydrofuran and the like), esters (e.g., ethyl acetate and the like), amides (e.g., N,N-dimethylformamide, N,N-dimethylacetamide and the like), water and a mixture thereof can be mentioned. The amount of the solvent to be used is generally 1 to 100 ml, preferably 1 to 50 ml, per 1 g of compound (VI).

The reaction time is generally about 0.5 to about 24 hr, preferably about 0.5 to about 10 hr. The reaction temperature is generally about −50° C. to about 100° C., preferably about −10° C. to about 50° C.

As a reducing agent, sodium borohydride, sodium cyanoborohydride, sodium triacetoxyborohydride and the like can be used. The amount of the reducing agent to be used is preferably about 0.2 to about 10 mol, more preferably about 0.2 to about 5 mol, per 1 mol of compound (VI).

The reduction can also be performed by catalytic hydrogenation.

The catalytic hydrogenation can be performed in the presence of a hydrogen source and a metal catalyst. Examples of the metal catalyst include palladium catalyst (e.g., palladium carbon, palladium hydroxide carbon, palladium oxide and the like), nickel catalyst (e.g., Raney-nickel and the like), platinum catalyst (e.g., platinum oxide, platinum carbon and the like), rhodium catalyst (e.g., rhodium carbon and the like), cobalt catalyst (e.g., Raney-cobalt and the like) and the like. Of these, palladium carbon or Raney-nickel is preferable. The amount of the metal catalyst to be used is about 0.01 to about 10 mol, preferably about 0.01 to about 5 mol, per 1 mol of compound (VI).

As a hydrogen source, hydrogen gas, formic acid, ammonium formate, triethylammonium formate, sodium phosphinate, hydrazine and the like can be mentioned. When a hydrogen source other than hydrogen gas is used, a compound of a hydrogen source is used in about 1 to about 100 mol, preferably about 1 to about 50 mol, more preferably about 1 to about 10 mol, for example, about 1 to about 5 mol, per 1 mol of compound (VI).

The reduction is advantageously performed using a solvent inert to the reaction. Such solvent is not particularly limited as long as the reaction proceeds, and alcohols (e.g., methanol, ethanol, propanol, butanol and the like), hydrocarbons (e.g., benzene, toluene, xylene and the like), halogenated hydrocarbons (e.g., dichloromethane, chloroform and the like), ethers (e.g., diethyl ether, dioxane, tetrahydrofuran and the like), esters (e.g., ethyl acetate and the like), amides (e.g., N,N-dimethylformamide, N,N-dimethylacetamide and the like), water and a mixture thereof can be mentioned. The amount of the solvent to be used is generally 1 to 100 ml, preferably 1 to 50 ml, per 1 g of compound (VI).

The reaction time is generally about 0.5 to about 24 hr, preferably about 0.5 to about 10 hr. The reaction temperature is generally about −50° C. to about 100° C., preferably about −20° C. to about 50° C.

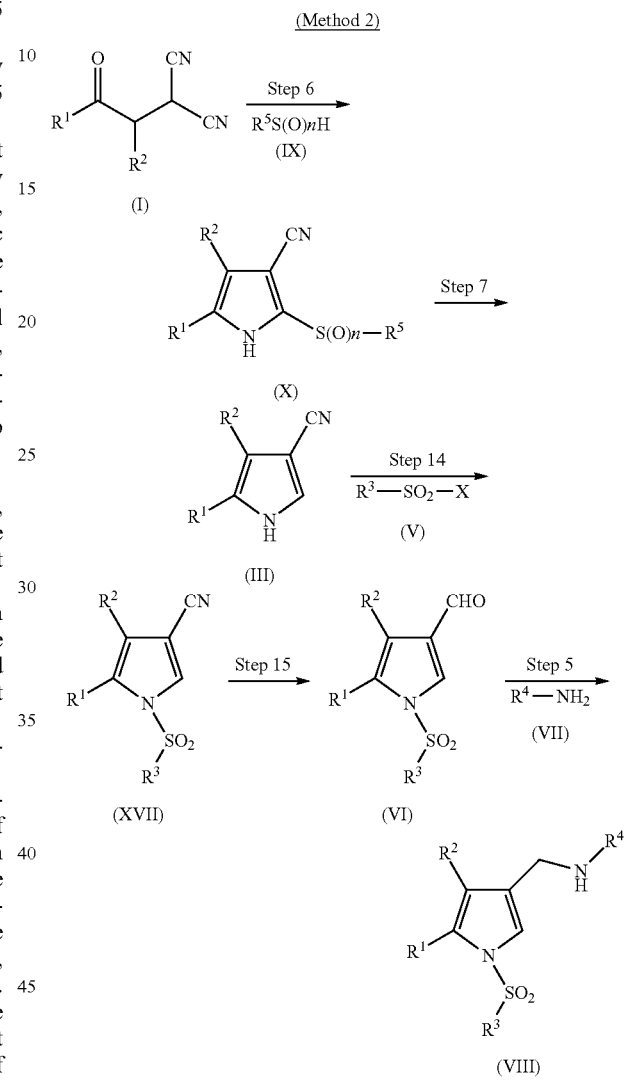

wherein each symbol is as defined above.

Step 6

Compound (X) or a salt thereof can be produced by reacting compound (I) or a salt thereof with compound (IX) or a salt thereof.

As compound (IX) or a salt thereof, thiocarboxylic acid (e.g., thiobenzoic acid), sodium thiomethoxide, a thiol compound represented by $R^5SH$ ($R^5$ is as defined above) and the like can be used. The amount of compound (IX) to be used is preferably about 1 to about 10 mol, more preferably about 1 to about 5 mol, per 1 mol of compound (I).

When sodium thiomethoxide is used as compound (IX) or a salt thereof, the reaction is preferably performed in the presence of an acid. As the acid, carboxylic acid such as acetic acid and the like, and the like can be mentioned. Preferred is acetic acid. The amount of the acid to be used is about 0.1 to about 10 mol, preferably about 1 to about 5 mol, per 1 mol of compound (I).

When thiocarboxylic acid or a thiol compound is used as compound (IX) or a salt thereof, the reaction is preferably performed in the presence of a base. Examples of the base include inorganic bases such as sodium hydride, sodium hydroxide, potassium hydroxide and the like, basic salts such as sodium carbonate, potassium carbonate, cesium carbonate, sodium hydrogen carbonate and the like, metal bases such as potassium ethoxide, potassium tert-butoxide, sodium methoxide, sodium ethoxide and the like, aromatic amines such as pyridine, lutidine and the like, tertiary amines such as diisopropylethylamine, triethylamine, tripropylamine, tributylamine, cyclohexyldimethylamine, 4-N,N-dimethylaminopyridine, N,N-dimethylaniline, N-methylpiperidine, N-methylpyrrolidine, N-methylmorpholine and the like, and the like. Preferred are tertiary amines such as triethylamine, diisopropylethylamine and the like. The amount of the base to be used is about 0.05 to about 10 mol, preferably about 0.1 to about 5 mol, per 1 mol of compound (I).

This reaction is advantageously carried out using a solvent inert to the reaction. While the solvent is not particularly limited as long as the reaction proceeds, solvents such as alcohols (e.g., methanol, ethanol, propanol, butanol and the like), aromatic hydrocarbons (e.g., benzene, toluene, xylene and the like), halogenated hydrocarbons (e.g., dichloromethane, chloroform, chlorobenzene and the like), ethers (e.g., diethyl ether, dioxane, tetrahydrofuran and the like), esters (e.g., ethyl acetate and the like), amides (e.g., N,N-dimethylformamide, N,N-dimethylacetamide and the like), ketones (e.g., acetone, methyl ethyl ketone and the like) and the like and a mixed solvent thereof and the like are preferable. The amount of the solvent to be used is generally 1 to 50 ml, preferably 1 to 20 ml, per 1 g of compound (I).

The reaction time is generally about 1 to about 50 hr, preferably about 1 to about 20 hr. The reaction temperature is generally about 0° C. to about 150° C., preferably about 15° C. to about 100° C.

Step 7

Compound (III) or a salt thereof can be produced by subjecting compound (X) or a salt thereof to a desulfurization reaction.

The desulfurization reaction can be performed by reaction with metals (e.g., Raney-nickel) or reaction with a combination of sodium borohydride and a metal salt (e.g., nickel chloride).

The desulfurization reaction is generally performed in a solvent inert to the reaction. Examples of such solvent include alcohols (e.g., methanol, ethanol, propanol, butanol and the like), aromatic hydrocarbons (e.g., benzene, toluene, xylene, chlorobenzene and the like), halogenated hydrocarbons (e.g., dichloromethane, chloroform and the like), ethers (e.g., diethyl ether, dioxane, tetrahydrofuran and the like), esters (e.g., ethyl acetate and the like), amides (e.g., N,N-dimethylformamide, N,N-dimethylacetamide and the like), carboxylic acids (e.g., acetic acid and the like), water and a mixture thereof. The amount of the solvent to be used is generally about 1 to about 50 ml, preferably about 1 to about 20 ml, per 1 g of compound (X).

The desulfurization reaction using Raney-nickel is preferably performed in the presence of a base. As the base, secondary amine such as morpholine and the like can be mentioned. The amount of the base to be used is about 0.1 to about 10 mol, preferably about 0.5 to about 5 mol, per 1 mol of compound (X).

The reaction time is generally about 1 to about 50 hr, preferably about 1 to about 20 hr. The reaction temperature is generally about 0° C. to about 200° C., preferably about 20° C. to about 150° C.

Step 14

Compound (XVII) or a salt thereof can be produced by reacting compound (III) or a salt thereof with compound (V) or a salt thereof, as in step 4.

Step 15

Compound (VI) or a salt thereof can be produced by reducing compound (XVII) or a salt thereof, followed by hydrolysis, as in step 3.

Then, the obtained compound (VI) or a salt thereof is reacted with compound (VII) or a salt thereof, in the same manner as in the aforementioned step 5, whereby compound (VIII) or a salt thereof can be produced.

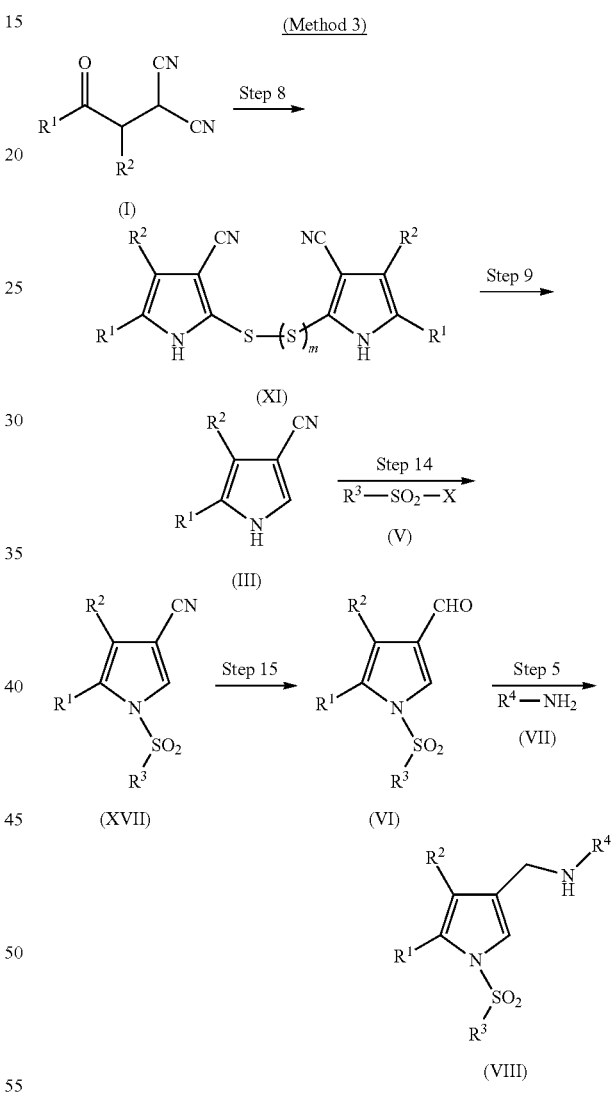

wherein each symbol is as defined above.

Step 8

Compound (XI) or a salt thereof can be produced by reacting compound (I) or a salt thereof with a sulfur reagent.

Examples of the sulfur reagent include hydrogen sulfide, thioacetic acid, thiouric acid, thioacetamide and the like. The amount of the sulfur reagent to be used is about 1 to about 10 mol, preferably about 1 to about 5 mol, per 1 mol of compound (I).

This reaction is advantageously performed using a solvent inert to the reaction. Such solvent is not particularly limited as long as the reaction proceeds, and solvents such as alcohols (e.g., methanol, ethanol, propanol, butanol and the like), aromatic hydrocarbons (e.g., benzene, toluene, xylene, chlorobenzene and the like), halogenated hydrocarbons (e.g., dichloromethane, chloroform and the like), ethers (e.g., diethyl ether, dioxane, tetrahydrofuran and the like), esters (e.g., ethyl acetate and the like), amides (e.g., N,N-dimethylformamide, N,N-dimethylacetamide and the like), ketones (e.g., acetone, methyl ethyl ketone and the like) and the like and a mixed solvent thereof, and the like are preferable. The amount of the solvent to be used is generally 1 to 50 ml, preferably 1 to 20 ml, per 1 g of compound (I).

This reaction is preferably performed in the presence of a base. Examples of the base include inorganic bases such as sodium hydride, sodium hydroxide, potassium hydroxide and the like, basic salts such as sodium carbonate, potassium carbonate, cesium carbonate, sodium hydrogen carbonate and the like, metal bases such as potassium ethoxide, potassium tert-butoxide, sodium methoxide, sodium ethoxide and the like, aromatic amines such as pyridine, lutidine and the like, tertiary amines such as diisopropylethylamine, triethylamine, tripropylamine, tributylamine, cyclohexyldimethylamine, 4-N,N-dimethylaminopyridine, N,N-dimethylaniline, N-methylpiperidine, N-methylpyrrolidine, N-methylmorpholine and the like, and the like. Preferred are tertiary amines such as triethylamine, diisopropylethylamine and the like. The amount of the base to be used is about 0.1 to about 10 mol, preferably about 0.1 to about 5 mol, per 1 mol of compound (I).

The reaction time is generally about 1 to about 50 hr, preferably about 1 to about 20 hr. The reaction temperature is generally about 0° C. to about 150° C., preferably about 0° C. to about 100° C.

Step 9

Compound (III) or a salt thereof can be produced by subjecting compound (XI) or a salt thereof to a desulfurization reaction.

The desulfurization reaction can be performed by a method similar to Method 2, step 7.

Compound (VIII) or a salt thereof can be produced from compound (III) or a salt thereof by a method similar to the aforementioned step 14, step 15 and step 5.

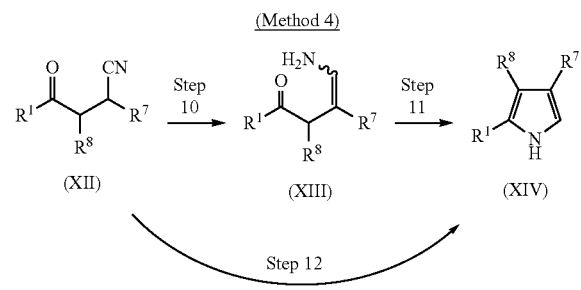

(Method 4)

wherein each symbol is as defined above.

Step 10

Compound (XIII) or a salt thereof can be produced by subjecting compound (XII) or a salt thereof to a reduction reaction.

The reduction reaction can be performed by a catalytic hydrogenation and the like.

The catalytic hydrogenation can be performed in the presence of a hydrogen source and a metal catalyst. Examples of the metal catalyst include palladium catalyst (e.g., palladium carbon, palladium hydroxide carbon, palladium oxide, palladium supported by carrier such as ceramic, cellulose, resin and the like, and the like), nickel catalyst (e.g., Raney-nickel and the like), platinum catalyst (e.g., platinum oxide, platinum carbon and the like), rhodium catalyst (e.g., rhodium carbon and the like), cobalt catalyst (Raney-cobalt and the like) and the like. Of these, palladium carbon or Raney-nickel is preferable. The amount of the metal catalyst to be used is about 0.001 to about 10 mol, preferably about 0.01 to about 5 mol, per 1 mol of compound (XII).

As the hydrogen source, hydrogen gas, formic acid, ammonium formate, triethylammonium formate, sodium phosphinate, hydrazine and the like can be mentioned. When a hydrogen source other than hydrogen gas is used, a compound of a hydrogen source is used in about 0.1 to about 100 mol, preferably about 0.1 to about 50 mol, more preferably about 1 to about 50 mol, particularly preferably about 1 to about 5 mol, per 1 mol of compound (XII).

The catalytic hydrogenation is generally performed in a solvent inert to the reaction. Examples of such solvent include alcohols (e.g., methanol, ethanol, propanol, butanol and the like), aromatic hydrocarbons (e.g., benzene, toluene, xylene, chlorobenzene and the like), halogenated hydrocarbons (e.g., dichloromethane, chloroform and the like), ethers (e.g., diethyl ether, dioxane, tetrahydrofuran and the like), esters (e.g., ethyl acetate and the like), amides (e.g., N,N-dimethylformamide, N,N-dimethylacetamide and the like), carboxylic acids (e.g., acetic acid and the like), water and a mixture thereof. The amount of the solvent to be used is generally about 1 to about 1000 ml, preferably about 3 to about 100 ml, per 1 g of compound (XII).

The hydrogen pressure under which the reaction is performed is generally about 0 to about 10 atm, preferably about 0 to about 5 atm. The reaction temperature is generally about −10° C. to about 200° C., preferably about 5° C. to about 80° C. The reaction time is generally about 0.5 to about 48 hr, preferably about 1 to about 12 hr.

Compound (XII) or a salt thereof can be produced according to the method described in, for example, JP-A-6-9554 and the like, or a method analogous thereto.

Step 11

Compound (XIV) or a salt thereof can be produced by cyclizing compound (XIII) or a salt thereof.

The cyclization reaction is preferably performed under acidic conditions. As the acid to be used, organic carboxylic acid (formic acid, acetic acid, propionic acid, trifluoroacetic acid, citric acid and the like), organic sulfonic acid (methanesulfonic acid, benzenesulfonic acid, p-toluenesulfonic acid, trifluoromethanesulfonic acid and the like), inorganic acid (hydrochloric acid, sulfuric acid, nitric acid and the like) and the like can be mentioned. The amount of the acid to be used is about 0.01 to about 100 mol, preferably about 0.1 to about 50 mol, per 1 mol of compound (XIII).

This reaction is advantageously performed using a solvent inert to the reaction. Such solvent is not particularly limited as long as the reaction proceeds, and alcohols (e.g., methanol, ethanol, propanol, butanol and the like), aromatic hydrocarbons (e.g., benzene, toluene, xylene, chlorobenzene and the like), halogenated hydrocarbons (e.g., dichloromethane, chloroform and the like), ethers (e.g., diethyl ether, dioxane, tetrahydrofuran and the like), esters (e.g., ethyl acetate and the like), amides (e.g., N,N-dimethylformamide, N,N-dimethylacetamide and the like), carboxylic acids (e.g., acetic acid and the like), water and a mixture thereof can be mentioned. The amount of the solvent to be used is generally about 1 to about 1000 ml, preferably about 3 to about 100 ml, per 1 g of compound (XIII).

The reaction time is generally about 0.1 to about 48 hr, preferably about 0.5 to about 6 hr. The reaction temperature is generally about −10° C. to about 100° C., preferably about 25° C. to about 60° C.

Step 12

Compound (XIV) or a salt thereof can also be obtained by subjecting compound (XIII) or a salt thereof obtained in the aforementioned step 10, without isolation, to a cyclization reaction in the next step 11.

For example, the catalyst is filtered off from the reaction mixture obtained in step 10, the filtrate is concentrated as necessary, and an acid is added to cause reaction, whereby compound (XIV) or a salt thereof can be obtained. The kind and amount of the reaction solvents and reagents, reaction time and reaction temperature are similar to those in step 10 and step 11.

Compound (VIII) or a salt thereof can be produced from compound (XIV) or a salt thereof by the aforementioned method of converting compound (III) to compound (VIII) or a method known per se.

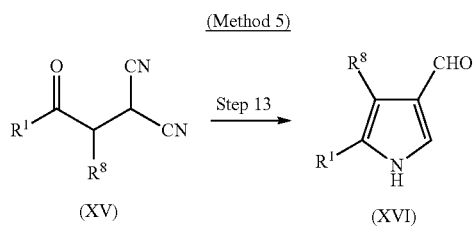

(Method 5)

(XV)  Step 13  (XVI)

wherein each symbol is as defined above.

Step 13

Compound (XVI) or a salt thereof can be produced by cyclizing compound (XV) or a salt thereof in the presence of a reducing agent.

As a reducing agent, a hydrogen source and a metal catalyst can be used. Examples of the metal catalyst include palladium catalyst (e.g., palladium carbon, palladium hydroxide carbon, palladium oxide, or palladium supported by carrier such as ceramic, cellulose, resin and the like, and the like), nickel catalyst (e.g., Raney-nickel and the like), platinum catalyst (e.g., platinum oxide, platinum carbon and the like), rhodium catalyst (e.g., rhodium carbon and the like), cobalt catalyst (Raney-cobalt and the like) and the like. Of these, palladium carbon or Raney-nickel is preferable. The amount of the metal catalyst to be used is about 0.001 to about 100 mol, preferably about 0.01 to about 10 mol, per 1 mol of compound (XV).

As a hydrogen source, hydrogen gas, formic acid, ammonium formate, triethylammonium formate, sodium phosphinate, hydrazine and the like can be mentioned. When a hydrogen source other than hydrogen gas is used, a compound of a hydrogen source is used in about 1 to about 1000 mol, preferably about 3 to about 30 mol, per 1 mol of compound (XV).

This reaction is advantageously performed using a solvent inert to the reaction. Such solvent is not particularly limited as long as the reaction proceeds, and alcohols (e.g., methanol, ethanol, propanol, butanol and the like), aromatic hydrocarbons (e.g., benzene, toluene, xylene, chlorobenzene and the like), halogenated hydrocarbons (e.g., dichloromethane, chloroform and the like), ethers (e.g., diethyl ether, dioxane, tetrahydrofuran and the like), esters (e.g., ethyl acetate and the like), amides (e.g., N,N-dimethylformamide, N,N-dimethylacetamide and the like), carboxylic acids (e.g., acetic acid and the like), water and a mixture thereof can be mentioned. The amount of the solvent to be used is generally about 1 to about 1000 ml, preferably about 3 to about 100 ml, per 1 g of compound (XV).

The cyclization reaction is preferably performed in the presence of an acid. Examples of the acid include organic carboxylic acid (formic acid, acetic acid, propionic acid, trifluoroacetic acid, citric acid and the like), organic sulfonic acid (methanesulfonic acid, benzenesulfonic acid, p-toluenesulfonic acid, trifluoromethanesulfonic acid and the like), inorganic acid (hydrochloric acid, sulfuric acid, nitric acid and the like) and the like. The amount of the acid to be used is about 0.01 to about 100 mol, preferably about 0.1 to about 50 mol, per 1 mol of compound (XV).

The reaction time is generally about 0.5 to about 48 hr, preferably about 1 to about 12 hr. The reaction temperature is generally about −10° C. to about 100° C., preferably about 10° C. to about 50° C.

Compound (VIII) or a salt thereof can be produced from compound (XVI) or a salt thereof by the aforementioned method of converting compound (IV) to compound (VIII) or a method known per se.

Of the 3-cyanopyrrole compounds used for the production method of the present invention, a compound represented by the formula

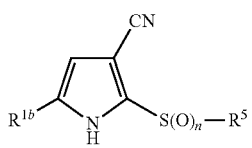

wherein $R^{1a}$ is an aryl group having substituent(s), or a salt thereof, and a compound represented by the formula

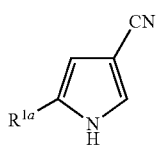

wherein $R^{1b}$ is an optionally substituted hydrocarbon group or an optionally substituted heterocyclic group, $R^5$ is an optionally substituted hydrocarbon group, an optionally substituted heterocyclic group, an acyl group or a group represented by —S—$R^6$ ($R^6$ is an optionally substituted hydrocarbon group or an optionally substituted heterocyclic group), and n is 0, 1 or 2 (excluding 2,2'-dithiobis(5-methyl-1H-pyrrole-3-carbonitrile), 2,2'-dithiobis(5-phenyl-1H-pyrrole-3-carbonitrile), 2,2'-dithiobis[5-(4-chlorophenyl)-1H-pyrrole-3-carbonitrile], 2,2'-dithiobis[5-(4-methylphenyl)-1H-pyrrole-3-carbonitrile] and 2,2'-dithiobis[5-(4-methoxyphenyl)-1H-pyrrole-3-carbonitrile]) or a salt thereof are novel compounds.

In a compound represented by the formula

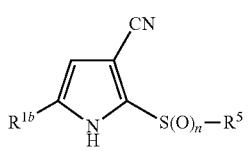

wherein each symbol is as defined above, when $R^5$ is —S—$R^6$ ($R^6$ is as defined above), a preferable embodiment of $R^6$ is

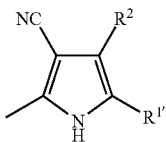

wherein $R^{1'}$ is as defined for the aforementioned $R^1$, preferably [1] a phenyl group optionally substituted by 1 to 5 substituents selected from (i) a halogen atom and (ii) $C_{1-6}$ alkyl optionally substituted by 1 to 5 halogen atoms, or [2] a pyridyl group optionally substituted by 1 to 4 substituents selected from lower ($C_{1-6}$)alkyl, a halogen atom, alkoxy ($C_{1-6}$ alkoxy), cyano, acyl (e.g., acetyl), nitro and amino, which is a preferable example of $R^1$, and further preferably [1] a phenyl group having one substituent selected from (i) a halogen atom and (ii) $C_{1-6}$ alkyl optionally substituted by 1 to 5 halogen atoms, at the 2-position, or [2] a pyridyl group optionally substituted 1 to 4 substituents selected from lower ($C_{1-6}$) alkyl, a halogen atom, alkoxy ($C_{1-6}$ alkoxy), cyano, acyl (e.g., acetyl), nitro and amino, and $R^2$ is as defined above, and

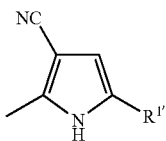

wherein the symbol in the formula is as defined above, is more preferable.

As $R^{1'}$, 2-position substituted phenyl (e.g., 2-fluorophenyl, 2-methylphenyl etc.) is particularly preferable.

$R^5$ in the formula

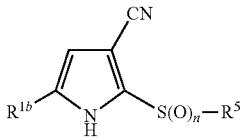

wherein each symbol is as defined above, is a preferable embodiment of the aforementioned $R^5$. Particularly, $R^5$ is

[1] a $C_{1-6}$ alkyl group (e.g., methyl, ethyl, propyl, isopropyl, butyl, isobutyl, sec-butyl, tert-butyl, pentyl, hexyl etc.) optionally substituted by 1 to 3 substituents selected from (i) a halogen atom (e.g., fluorine atom, chlorine atom, bromine atom, iodine atom etc.), (ii) nitro, (iii) amino and (iv) carboxyl,

[2] a $C_{6-14}$ aryl group (e.g., phenyl, 1-naphthyl, 2-naphthyl, 2-biphenylyl, 3-biphenylyl, 4-biphenylyl, 2-anthryl etc.) optionally substituted by 1 to 3 substituents selected from (i) a halogen atom (e.g., fluorine atom, chlorine atom, bromine atom, iodine atom etc.), (ii) nitro, (iii) amino and (iv) carboxyl,

[3] a heterocyclic group (e.g., pyridyl (e.g., 2-, 3- or 4-pyridyl) etc.),

[4] an optionally substituted $C_{6-14}$ aryl-carbonyl group (e.g., benzoyl, naphthalenecarbonyl etc.), or

[5] a group represented by the formula

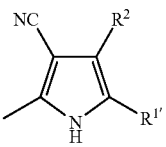

wherein the symbols in the formula are as defined above.

EXAMPLES

The present invention is explained in detail in the following by referring to Reference Examples and Examples, which are not to be construed as limitative.

In the following Reference Examples and Examples, the "room temperature" generally means about 10° C. to about 35° C., but it is not particularly strictly limited. The mixing ratio of liquids shows a volume ratio. Unless otherwise specified, "%" means weight %. The yield is in mol/mol %. Silica gel column chromatography was performed using silica gel 60 (0.063-0.200 mm) manufactured by MERCK or Fuji Silysia Chemical Ltd. Chromatorex (trade name) NH (described as basic silica gel column chromatography). The melting point was measured using Yanagimoto trace melting point measurement apparatus or Büchi trace melting point measurement apparatus (B-545), and uncorrected. For $^1$H-NMR spectrum, tetramethylsilane was used as the internal standard, and Bruker DPX-300 (300 MHz) or Bruker AVANCEIII500 (500 MHz) were used for the measurement.

The following abbreviations in Examples and Reference Examples mean as follows.

s: singlet, d: doublet, dd: double doublet, dt: double triplet, t: triplet, q: quartet, m: multiplet, br: broad, brs: broad singlet, J: coupling constant, Hz: Hertz, THF: tetrahydrofuran, HPLC: high performance liquid chromatography.

Reference Example 1

2-chloro-5-(2-fluorophenyl)-1H-pyrrole-3-carbonitrile

[2-(2-Fluorophenyl)-2-oxoethyl]propanedinitrile (135.0 g, 667.7 mmol) and ethyl acetate (540 ml) were added in a four neck flask, 4 N hydrochloric acid-ethyl acetate (417 ml, 1.67 mol) was added, and the mixture was stirred at the internal temperature of 40-50° C. for 2.5 hr. Ethyl acetate (270 ml) was added, and the mixture was stirred at the internal temperature of 70-80° C. for 2 hr. The internal temperature was cooled to 50° C., and seed crystals (68 mg) of the title compound were added. The mixture was continuously stirred at the internal temperature of 20-30° C. for 0.5 hr and at the internal temperature of 0-10° C. for 1 hr. The precipitated crystals were collected by filtration, washed with cold ethyl acetate (270 ml), and dried under reduced pressure at 50° C. until a constant weight was reached to give the title compound (73.9 g, yield 50.2%).

$^1$H-NMR (300 MHz, DMSO-$d_6$) δ (ppm): 6.91 (d, J=2.0 Hz, 1H), 7.27-7.42 (m, 3H), 7.70-7.75 (m, 1H), 13.05 (brs, 1H).

elemental analysis ($C_{11}H_6N_2ClF$)

Calculated: C, 59.88; H, 2.74; N, 12.70; Cl, 16.06; F, 8.61.
Found: C, 59.74; H, 2.75; N, 12.75; Cl, 16.02; F, 8.51.
melting point 218-220° C.

Reference Example 2

2-chloro-5-(2-fluorophenyl)-1H-pyrrole-3-carbonitrile

[2-(2-Fluorophenyl)-2-oxoethyl]propanedinitrile (5.0 g, 24.7 mmol) and THF (50 ml) were added in a four neck flask, and then hydrochloric acid gas (5 g, 137 mmol) was added. The mixture was stirred at the internal temperature of 55-65° C. for 3 hr. Acetonitrile (20 ml) was added, and the mixture was concentrated to about 17.5 g. Acetonitrile (20 ml) was added, and the mixture was concentrated again to about 17.5 g. Acetonitrile (17.5 ml) was added, and water (15 ml) was added dropwise at the internal temperature of 55-65° C. The mixture was continuously stirred at the internal temperature of 55-65° C. for 1 hr and at the internal temperature of 20-30° C. for 1 hr. The precipitated crystals were collected by filtration, washed with a cold mixed solution of acetonitrile and water (1:1, 10 ml), and dried under reduced pressure at 50° C. until a constant weight was reached to give the title compound (4.59 g, yield 84.2%).

$^1$H-NMR (500 MHz, CDCl$_3$) δ (ppm): 6.77-6.78 (m, 1H), 7.14-7.23 (m, 2H), 7.28-7.31 (m, 1H), 7.51-7.55 (m, 1H), 9.21 (brs, 1H).

Reference Example 3

[2-(2-methylphenyl)-2-oxoethyl]propanedinitrile

2-Methylacetophenone (466 mmol, 62.5 g) and ethyl acetate (375 ml) were added in a four neck flask. The internal temperature was maintained at 25±5° C., and a solution of bromine (489 mmol, 78.1 g) in ethyl acetate (180 ml) was slowly added dropwise. After the completion of the dropwise addition, the mixture was stirred at the same temperature for 1 hr. Tap water (375 ml) was added dropwise at the internal temperature of not more than 35° C., sodium sulfite (89.4 mmol, 11.3 g) was added, and the mixture was stirred at room temperature for 1 hr. The organic layer was separated, and washed successively with 3% aqueous sodium hydrogen carbonate solution (375 ml) and 10% brine (375 ml) to give a solution of 2-bromo-1-(2-methylphenyl)ethanone in ethyl acetate.

The solution of 2-bromo-1-(2-methylphenyl)ethanone in ethyl acetate obtained above was cooled, malononitrile (466 mmol, 30.8 g) was added at the internal temperature of 5±5° C., and the dropping funnel was washed with ethyl acetate (40 ml) and the washing was added. Diisopropylethylamine (513 mmol, 87.8 ml) was added dropwise at the internal temperature of 10±5° C. After the dropwise addition, the mixture was stirred at the internal temperature of 5±5° C. for 2 hr. Tap water (375 ml) was added, and the mixture was partitioned at room temperature. The aqueous layer was further extracted with ethyl acetate (188 ml). The organic layers were combined, and washed with a mixture of 1 N hydrochloric acid (18.8 ml) and 10% brine (188 ml), and 10% brine (188 ml) in this order. The organic layer was concentrated to about half amount under reduced pressure. Methanol (375 ml) was added to the concentrate, and the mixture was concentrated to about 239 g. This operation was performed 3 times in total. Water (27.7 ml) was added while stirring the concentrate with heating to 55±5° C., and the mixture was stirred at the same temperature for 1 hr. The reaction mixture was gradually cooled to not more than 30° C., further cooled to the internal temperature of 5±5° C., and stirred for 1 hr. The precipitated crystals were collected by filtration, cooled, and washed with a mixture of methanol (24 ml) and water (3.6 ml). The wet crystals were dried under reduced pressure at 50° C. to give the title compound (70.3 g, yield 76%).

melting point 92.0-93.0° C.

$^1$H-NMR (300 MHz, DMSO-d$_6$) δ (ppm): 2.47 (s, 3H), 4.01 (d, J=6.04 Hz, 2H), 5.08 (t, J=6.04 Hz, 1H), 7.33-7.40 (m, 2H), 7.48-7.54 (m, 1H), 7.90 (d, J=7.84 Hz, 1H).

elemental analysis (C$_{12}$H$_{10}$N$_2$O)

Calculated: C, 72.71; H, 5.08; N, 14.13; O, 8.07.

Found: C, 72.87; H, 5.06; N, 13.95.

Reference Example 4

[2-(2-methylphenyl)-2-oxoethyl]propanedinitrile

2-Methylacetophenone (466 mmol, 62.5 g) and ethyl acetate (375 ml) were added in a four neck flask. While maintaining the internal temperature at 25±5° C., a solution of bromine (489 mmol, 78.1 g) in ethyl acetate (180 ml) was slowly added dropwise. After the completion of the dropwise addition, the mixture was stirred at the same temperature for 1 hr. Tap water (375 ml) was added dropwise at the internal temperature of not more than 35° C., sodium sulfite (89.4 mmol, 11.3 g) was added, and the mixture was stirred at room temperature for 1 hr. The organic layer was separated, and washed successively with 3% aqueous sodium hydrogen carbonate solution (375 ml) and 10% brine (375 ml) to give a solution of 2-bromo-1-(2-methylphenyl)ethanone in ethyl acetate.

The solution of 2-bromo-1-(2-methylphenyl)ethanone in ethyl acetate obtained above was cooled, malononitrile (466 mmol, 30.8 g) was added at the internal temperature of 5±5° C., and the dropping funnel was washed with ethyl acetate (40 ml) and the washing was added. Diisopropylethylamine (513 mmol, 87.8 ml) was added dropwise at the internal temperature of 10±5° C. After the dropwise addition, the mixture was stirred at the internal temperature of 5±5° C. for 2 hr. Tap water (375 ml) was added, and the mixture was partitioned at room temperature. The aqueous layer was further extracted with ethyl acetate (188 ml). The organic layers were combined, and washed with a mixture of 1 N hydrochloric acid (18.8 ml) and 10% brine (188 ml), and 10% brine (188 ml) in this order. The organic layer was concentrated to about half amount under reduced pressure. Methanol (375 ml) was added to the concentrate, and the mixture was concentrated to about 388 g. This operation was performed 3 times in total to give a slurry of the title compound and methanol.

Reference Example 5

[2-(2-methylphenyl)-2-oxoethyl]propanedinitrile

2-Methylacetophenone (30 g, 223.5 mmol) and ethyl acetate (180 ml) were mixed, and a mixture of bromine (39 g) and ethyl acetate (90 ml) was added dropwise at room temperature over about 3 hr. Then, water (180 ml) was added dropwise, and the mixture was stirred at room temperature for about 1 hr. Aqueous sodium sulfite solution (186 ml) was added dropwise to the reaction mixture over about 1 hr, the mixture was partitioned, and the organic layer was washed with 3% aqueous sodium hydrogen carbonate solution (186 ml) and 10% aqueous sodium chloride solution (198 ml) to give a solution of 2-bromo-1-(2-methylphenyl)ethanone in ethyl acetate.

Malononitrile (14.8 g) was added, and ethyl acetate (20 ml) was added. Diisopropylethylamine (42.1 ml) was added dropwise at about 10° C., and the mixture was stirred for about 3 hr. Water (180 ml) was added, and the organic layer was separated, and washed with a mixture of 1 N hydrochloric acid (9 ml) and water (90 ml), and then with 10% aqueous sodium chloride solution (198 ml). The organic layer was concentrated under reduced pressure, methanol (180 ml) was added, and the mixture was concentrated again under reduced pressure to about 187 g. Water (13 ml) was added at about 55° C., and the mixture was stirred at about 10° C. for about 1 hr. The precipitated crystals were collected by filtration, and washed with a mixture of methanol (23.1 ml) and water (3.5 ml). The wet crystals were dried under reduced pressure to give the title compound (32.1 g, yield 72.5%).

Example 1

5-(2-fluorophenyl)-1H-pyrrole-3-carbonitrile

2-Chloro-5-(2-fluorophenyl)-1H-pyrrole-3-carbonitrile (5.0 g, 22.7 mmol), methanol (150 ml) and diisopropylethylamine (3.8 g, 29.5 mmol) were added in an autoclave, and the autoclave was purged with nitrogen. 5% Palladium carbon (N.E. CHEMCAT, Standard, 0.5 g) was added. Then, under a hydrogen atmosphere (0.1 MPa), the mixture was vigorously stirred at the internal temperature of 15-25° C. for about 4 hr. After purging with nitrogen gas, the catalyst was filtered off, and washed with methanol (15 ml). The organic layer was concentrated under reduced pressure to about 13 g. The amount of the content was adjusted to about 28 g with ethanol. Water (40 ml) was added dropwise at the internal temperature of 15-25° C., and the mixture was stirred at the same temperature for 1 hr. The mixture was cooled to the internal temperature of 0-10° C. and stirred for 1 hr. The precipitated crystals were collected by filtration, washed with a cold mixed solution of ethanol and water (1:2, 15 ml) and dried under reduced pressure at 50° C. until a constant weight was reached to give the title compound (3.8 g, yield 88%).

$^1$H-NMR (300 MHz, DMSO-$d_6$) δ (ppm): 6.86 (d, J=1.67 Hz, 1H), 7.22-7.29 (m, 3H), 7.71-7.74 (m, 2H), 12.18 (brs, 1H).

elemental analysis ($C_{11}H_7N_2F$)
Calculated: C, 70.96; H, 3.79; N, 15.05; F, 10.20.
Found: C, 70.77; H, 3.86; N, 15.04.
melting point 158.5-160.5° C.

Example 2

5-(2-fluorophenyl)-1H-pyrrole-3-carbonitrile

2-Chloro-5-(2-fluorophenyl)-1H-pyrrole-3-carbonitrile (25.0 g, 113 mmol), ethanol (350 ml) and diisopropylethylamine (19.0 g, 147 mmol) were added in an autoclave, and the autoclave was purged with nitrogen. A suspension of 5% palladium carbon (N.E. CHEMCAT, Standard, 2.5 g) in ethanol (25 ml) was added. Under a hydrogen atmosphere, the mixture was vigorously stirred at the internal temperature of 15-25° C. for about 7 hr. After purging with nitrogen gas, the catalyst was filtered off, and washed with ethanol (75 ml). The filtrates were combined and concentrated under reduced pressure to about 140 g. Water (200 ml) was added dropwise at the internal temperature of 20-30° C., and the mixture was stirred at the same temperature for 0.5 hr. The mixture was cooled to the internal temperature of 0-10° C. and stirred for 1 hr. The precipitated crystals were collected by filtration, washed with a cold mixed solution of ethanol and water (1:2, 75 ml), and dried under reduced pressure at 50° C. until a constant weight was reached to give the title compound (19.1 g, yield 90.7%).

$^1$H-NMR (500 MHz, CDCl$_3$) δ (ppm): 6.84-6.85 (m, 1H), 7.13-7.22 (m, 2H), 7.25-7.29 (m, 1H), 7.38-7.39 (m, 1H), 7.56-7.60 (m, 1H), 9.36 (brs, 1H).

Example 3

5-(2-fluorophenyl)-1H-pyrrole-3-carbaldehyde 5-(2-Fluorophenyl)-1H-pyrrole-3-carbonitrile (5.0 g, 26.9 mmol) and THF (33 ml) were added in a four neck flask, and the mixture was dissolved at the internal temperature of 15-25° C. Acetic acid (55 ml) and water (11 ml) were added. After purging with nitrogen gas, Raney-nickel (Kawaken Fine Chemicals Co., Ltd., NDHT-90, 2.5 ml, wet weight 4 g) was added. Under a hydrogen atmosphere, the mixture was vigorously stirred at the internal temperature of 15-25° C. for about 3 hr. After purging with nitrogen gas, Raney-nickel was filtered off, and washed with ethyl acetate (50 ml). 5 N Aqueous sodium hydroxide solution (about 180 ml) was added to the filtrate at the internal temperature of 10-35° C. to adjust the mixture to pH 7-8 and the mixture was partitioned. The organic layer was washed with 5% aqueous sodium hydrogen carbonate solution (25 ml) and 5% brine (25 ml). Water (25 ml) was added to the organic layer, and the mixture was adjusted with 6 N hydrochloric acid to pH 3.0-3.5 at the internal temperature of 15-25° C. After stirring overnight, the mixture was partitioned. The organic layer was washed with 5% brine (25 ml), concentrated under reduced pressure to about 18 g. After increasing the internal temperature to 65-70° C., the mixture was cooled to the internal temperature of 45-55° C., and further stirred for 1 hr. After cooling to the internal temperature of 15-25° C., n-heptane (25 ml) was added dropwise, and the mixture was stirred at the same temperature for 1 hr. Furthermore, the mixture was stirred at the internal temperature of 0-10° C. for 1 hr. The precipitated crystals were collected by filtration, washed with ethyl acetate:n-heptane (1:2, 15 ml), and dried under reduced pressure at 50° C. until a constant weight was reached to give the title compound (23.9 g, yield 78%).

$^1$H-NMR (300 MHz, DMSO-$d_6$) δ (ppm): 6.91 (d, J=1.6 Hz, 1H), 7.21-7.31 (m, 3H), 7.75-7.80 (m, 2H), 9.76 (s, 1H), 12.17 (brs, 1H).

elemental analysis ($C_{11}H_8NOF$)
Calculated: C, 69.83; H, 4.26; N, 7.40; O, 8.46; F, 10.04.
Found: C, 69.91; H, 4.27; N, 7.33.
melting point 123.0-126.0° C. dec.

Example 4

5-(2-fluorophenyl)-1-(pyridin-3-ylsulfonyl)-1H-pyrrole-3-carbaldehyde 5-(2-Fluorophenyl)-1H-pyrrole-3-carbaldehyde (5.00 g, 26.43 mmol), N,N-dimethylpyridin-4-amine (0.65 g, 5.29 mmol), diisopropylethylamine (4.78 g, 37.00 mmol) and acetonitrile (18.5 ml) were added in a four neck flask, and a solution of pyridine-3-sulfonyl chloride (5.63 g, 31.71 mmol) in acetonitrile (5 ml) was added. Acetonitrile (1.5 ml) was further added, and the mixture was stirred at the internal temperature of 40-50° C. for 1.5 hr. The internal temperature was cooled to 30° C., and water (15 ml) was added dropwise. The mixture was adjusted to pH 4-5 with 0.5 N hydrochloric acid. Seed crystals (2.5 mg) of the title compound were added, and then water (about 30 ml) was added dropwise. After stirring at the internal temperature of 20-30° C. for 0.5 hr, the internal temperature was cooled to 0-10° C., and the mixture was stirred for 1 hr. The precipitated crystals were collected by filtration, washed with a cold mixed solution of acetonitrile and water (1:2, 7.5 ml), and water (7.5 ml×2), and dried under reduced pressure at 50° C. until a constant weight was reached to give the title compound (7.57 g, yield 86.7%).

$^1$H-NMR (300 MHz, CDCl$_3$) δ (ppm): 6.68 (d, J=1.7 Hz, 1H), 7.01-7.05 (m, 1H), 7.16-7.18 (m, 2H), 7.37-7.40 (m, 1H), 7.45-7.51 (m, 1H), 7.69-7.72 (m, 1H), 8.15 (d, J=1.8 Hz, 1H), 8.58 (d, J=1.7 Hz, 1H), 8.82 (dd, J=4.8, 1.5 Hz, 1H), 9.90 (s, 1H).

elemental analysis (C$_{16}$H$_{11}$N$_2$O$_3$SF)

Calculated: C, 58.17; H, 3.36; N, 8.48; O, 14.53; S, 9.71; F, 5.75.

Found: C, 58.32; H, 3.46; N, 8.54; S, 9.76; F, 5.62.

melting point 106-108° C.

Example 5

1-[5-(2-fluorophenyl)-1-(pyridin-3-ylsulfonyl)-1H-pyrrol-3-yl]-N-methylmethanamine fumarate To a nitrogen-purged flask were added N,N-dimethylacetamide (108 ml) and sodium borohydride (3.06 g, 81.74 mmol), and the mixture was dissolved (solution A). To another nitrogen-purged flask were added 5-(2-fluorophenyl)-1-(pyridin-3-ylsulfonyl)-1H-pyrrole-3-carbaldehyde (60.00 g, 181.64 mmol) and methanol (300 ml), and then a solution (18.34 g, 236.13 mmol) of 40% methylamine in methanol was added dropwise at room temperature. The mixture was further stirred at the internal temperature of 20-30° C. for 30 min. The internal temperature was cooled to −10° C., and solution A previously prepared was added dropwise at the internal temperature of not more than 0° C. N,N-Dimethylacetamide (12 ml) was added, and the mixture was stirred at the internal temperature of −10 to 0° C. for 1 hr. 1 N HCl (360 ml) was added dropwise at the internal temperature of not more than 20° C., and the mixture was stirred at the internal temperature of 10-20° C. for 30 min. 12.5% Aqueous ammonia (240 ml), ethyl acetate (600 ml) and water (180 ml) were added, and the mixture was partitioned. Water (240 ml) and ethyl acetate (360 ml) were added to the aqueous layer and the mixture was extracted again. The organic layers were combined and washed twice with 5% brine (360 ml). The organic layer was concentrated to about 253 g, and N,N-dimethylacetamide (480 ml) was added. The mixture was heated to the internal temperature of 50° C., and fumaric acid (21.08 g, 181.64 mmol) was added. The mixture was stirred at the internal temperature of 50° C. for 30 min, cooled, and stirred at room temperature for 1 hr. The precipitated crystals were filtered, washed with a mixed solution of ethyl acetate and N,N-dimethylacetamide (1:2, 90 ml), and then ethyl acetate (120 ml), and dried under reduced pressure at 50° C. to give a crude product (62.73 g).

The crude product (55.00 g) obtained above was suspended in a mixed solution of methanol and water (7:3, 550 ml), and dissolved at the internal temperature of 60-65° C. Activated carbon SHIRASAGI A (registered trade mark, 2.75 g) was added, and the mixture was stirred for 10 min, filtered, and washed with a mixed solution of methanol and water (7:3, 110 ml). The combined filtrate was heated to the internal temperature of about 55° C., cooled to room temperature, and further stirred at the internal temperature of 0-10° C. for 1 hr. The precipitated crystals were filtered, washed with a mixed solution of methanol and water (1:1, 110 ml), and dried under reduced pressure at 50° C. to give the title compound (47.50 g, yield 64.6%).

$^1$H-NMR (300 MHz, DMSO-d$_6$) δ (ppm): 2.46 (s, 3H), 3.92 (s, 2H), 6.49 (s, 2H), 6.51 (d, J=1.7 Hz, 1H), 7.08-7.13 (m, 1H), 7.20-7.26 (m, 2H), 7.49-7.54 (m, 1H), 7.60-7.64 (m, 1H), 7.78 (s, 1H), 7.89 (dd, J=8.2, 1.6 Hz, 1H), 8.57 (d, J=2.2 Hz, 1H), 8.89 (d, J=4.7 Hz, 1H), 10.81 (brs, 2H), 1H not detected.

elemental analysis (C$_{21}$H$_{20}$N$_3$O$_6$SF)

Calculated: C, 54.66; H, 4.37; N, 9.11; O, 20.80; S, 6.95; F, 4.12.

Found: C, 54.68; H, 4.31; N, 9.07; S, 7.00; F, 4.15.

melting point 203-205° C.

Example 6

1-[5-(2-fluorophenyl)-1-(pyridin-3-ylsulfonyl)-1H-pyrrol-3-yl]-N-methylmethanamine fumarate N,N-Dimethylacetamide (18 ml) and sodium borohydride (0.52 g, 13.6 mmol) were added in a nitrogen-purged flask, and the mixture was dissolved (solution A). In another nitrogen-purged flask were added 5-(2-fluorophenyl)-1-(pyridin-3-ylsulfonyl)-1H-pyrrole-3-carbaldehyde (10.0 g, 30.3 mmol) and methanol (50 ml), and then a solution (3.06 g, 39.4 mmol) of 40% methylamine in methanol was added dropwise at room temperature, and the mixture was further stirred at the internal temperature of 20-30° C. for 30 min. The internal temperature was lowered to 5° C., and solution A previously prepared was added dropwise at the internal temperature of 0-10° C. N,N-Dimethylacetamide (2 ml) was added, and the mixture was stirred at the internal temperature of 0-10° C. for 1 hr. 1 N HCl (70 ml) was added dropwise at the internal temperature of not more than 20° C., and the mixture was stirred at the internal temperature of 15-25° C. for 30 min. 12.5% Aqueous ammonia (60 ml) and ethyl acetate (100 ml) were added to partition the mixture. 5% Brine (50 ml) and ethyl acetate (50 ml) were added to the aqueous layer and the mixture was extracted again. The organic layers were combined and washed twice with 5% brine (60 ml). The organic layer was concentrated to about 25 ml, ethyl acetate (70 ml) was added, and the mixture was concentrated again to about 38.0 ml. N,N-Dimethylacetamide (60 ml) was added, the mixture was heated to the internal temperature of 45° C., and fumaric acid (3.51 g, 30.3 mmol) was added. After stirring at the internal temperature of 40-50° C. for 30 min, ethyl acetate (30 ml) was added dropwise, and the mixture was stirred at the internal temperature of 40-50° C. for 30 min. The mixture was cooled, and stirred at room temperature for 1 hr. The precipitated crystals were collected by filtration, and washed with a mixed solution of ethyl acetate and N,N-dimethylacetamide (1:1, 15 ml), and then with ethyl acetate (30 ml) to give a crude product (wet product).

The crude product (wet product) obtained above was suspended in a mixed solution of methanol and water (1:1, 100 ml), and dissolved at the internal temperature of 60-70° C. Activated carbon SHIRASAGI A (registered trade mark, 0.30 g) was added, and the mixture was stirred for 10 min, filtered, and washed with a mixed solution of methanol and water (1:1, 20 ml). The combined filtrate was dissolved again at the internal temperature of about 55-65° C., cooled to room temperature, and further stirred at the internal temperature of 0-10° C. for 1 hr. The precipitated crystals were collected by filtration, washed with a mixed solution of methanol and water (1:1, 20 ml), and dried under reduced pressure at 50° C. to give the title compound (10.07 g, yield 72.1%).

$^1$H-NMR (500 MHz, DMSO-d$_6$) δ (ppm): 2.44 (s, 3H), 3.87 (s, 2H), 6.48-6.49 (m, 3H), 7.09-7.12 (m, 1H), 7.20-7.25

(m, 2H), 7.50-7.55 (m, 1H), 7.60-7.63 (m, 1H), 7.74-7.75 (m, 1H), 7.87-7.89 (m, 1H), 8.55-8.56 (m, 1H), 8.87-8.89 (m, 1H), 3H not detected.

Example 7

(1) S-{3-cyano-5-(2-fluorophenyl)-1H-pyrrol-2-yl}benzenecarbothioate

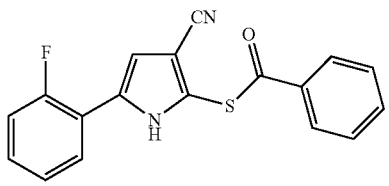 [SMILES: N#Cc1cc(-c2ccccc2F)[nH]c1SC(=O)c1ccccc1]

To a solution of [2-(2-fluorophenyl)-2-oxoethyl]propanedinitrile (30.1 g, 149 mmol) in methanol (200 ml) were added thiobenzoic acid (28.2 ml, 238 mmol) and triethylamine (2.08 ml, 14.9 mmol), and the mixture was stirred at 60-70° C. for 2 hr. The mixture was allowed to cool, and methanol (300 ml) and water (50 ml) were added at about 50° C. After stirring at room temperature for 1 hr and at 0-10° C. for 1 hr, the crystals were collected by filtration, washed with an ice-cooled mixed solution (120 ml) of water/methanol (4:1) and dried under reduced pressure at 50° C. to give the title compound (38.6 g, yield 80%).

$^1$H-NMR (300 MHz, TMS, DMSO-$d_6$) δ (ppm): 12.9 (brs, 1H), 8.06-8.03 (m, 2H), 7.82-7.77 (m, 2H), 7.69-7.64 (t, J=7.6 Hz, 2H), 7.41-7.32 (m, 3H), 7.09 (s, 1H).

(2) 5-(2-fluorophenyl)-1H-pyrrole-3-carbonitrile

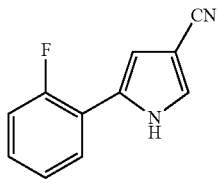

Under a nitrogen stream, a Raney-nickel catalyst (76 g), N,N-dimethylacetamide (206 ml) and morpholine (15.6 ml, 0.18 mol) were placed in a reactor, and the mixture was stirred at room temperature. While maintaining the internal temperature at not more than 40° C., a solution of S-{3-cyano-5-(2-fluorophenyl)-1H-pyrrol-2-yl}benzenecarbothioate (38.6 g, 0.12 mol) in N,N-dimethylacetamide (180 ml) was slowly added dropwise. The mixture was heated under reflux at the internal temperature of 100-110° C. for 1 hr. After allowing the mixture to cool to room temperature, the Raney-nickel catalyst was filtered off, and washed with ethyl acetate (120 ml). Ethyl acetate (280 ml) and 10% brine (600 ml) were added to the filtrate, and the mixture was extracted and partitioned. The aqueous layer was extracted 3 times with ethyl acetate (200 ml, 100 ml, 100 ml), the organic layers were combined, and washed with water (1 L). Ethanol (120 ml) was added to the concentrate, water (240 ml) was added while stirring with heating at 60-65° C., and the mixture was further stirred at the same temperature for 1 hr. The mixture was allowed to cool to 30° C. or below, and stirred at 0-10° C. for 1 hr. The crystals were collected by filtration, and washed with an ice-cooled mixed solution (40 ml) of water/ethanol (1:2), and dried under reduced pressure at 50° C. until a constant weight was reached to give the title compound (17.6 g, yield 79%).

$^1$H-NMR (DMSO-$d_6$, TMS, 300 MHz) δ (ppm): 9.3 (br, 1H), 7.6-7.5 (m, 1H), 7.4-7.3 (m, 1H), 7.3-7.1 (m, 3H), 6.84 (d, J=1.7 Hz, 1H).

Example 8

(1) 2,2'-disulfanediylbis[5-(2-fluorophenyl)-1H-pyrrole-3-carbonitrile]

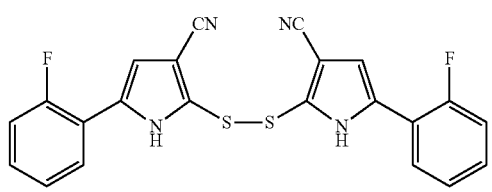 [SMILES: N#Cc1cc(-c2ccccc2F)[nH]c1SSc1[nH]c(-c2ccccc2F)cc1C#N]

[2-(2-Fluorophenyl)-2-oxoethyl]propanedinitrile (5.05 g, 25 mmol), methanol (50.5 ml), thioacetic acid (1.79 ml, 25 mmol) and triethylamine (0.7 ml, 5 mmol) were charged in a 100 ml four neck flask, and the mixture was heated under reflux for 10 hr. Water (10.2 ml) was added, and the mixture was refluxed for 1 hr. The mixture was allowed to cool and ice-cooled, and the precipitated crystals were collected by filtration and washed by sprinkling an ice-cooled mixed solution (20.2 ml) of water/methanol (1:10), and dried under reduced pressure at 50° C. to give the title compound (4.64 g, yield 85%).

(2) 5-(2-fluorophenyl)-1H-pyrrole-3-carbonitrile

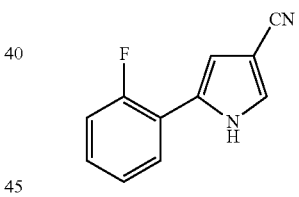

Under a nitrogen stream, Raney-nickel (12.6 g), N,N-dimethylacetamide (30 ml), morpholine (1.36 ml, 15.6 mmol) and a solution of 2,2'-dithiobis[5-(2-fluorophenyl)-1H-pyrrole-3-carbonitrile] (4.50 g, 10.4 mmol) in N,N-dimethylacetamide (15 ml) were charged in a 100 ml four neck flask, and the mixture was heated under reflux at 105° C. for 5.5 hr. The reaction mixture was cooled, and the catalyst was filtered off, and washed with N,N-dimethylacetamide and ethyl acetate in this order. 5% Brine was added to the filtrate and washings, the mixture was partitioned, and the aqueous layer was extracted 3 times with ethyl acetate. The organic layers were combined, washed with 5% brine, and concentrated to dryness under reduced pressure. Ethanol (22.5 ml) was added to the residue, and the mixture was dissolved by heating. Water (45 ml) was added to cause crystallization. The slurry was heated under reflux for 1 hr, and allowed to cool and ice-cooled, and the crystals were collected by filtration. The crystals were washed by sprinkling an ice-cooled mixed solution (10 ml) of water/ethanol (1:2) and dried under reduced pressure at 50° C. to give the title compound (3.45 g, yield 85%).

¹H-NMR (DMSO-d₆, TMS, 300 MHz) δ (ppm): 9.3 (br, 1H), 7.6-7.5 (m, 1H), 7.4-7.3 (m, 1H), 7.3-7.1 (m, 3H), 6.84 (d, J=1.7 Hz, 1H).
mass spectrometry (EI, m/z) (rel intensity): 186 (M+, 100), 158 (20), 132 (11).
elemental analysis (C₁₁H₇N₂F)
Calculated: C, 70.96; H, 3.79; N, 15.05.
Found: C, 70.69; H, 3.89; N, 14.86.

Example 9

2-(methylsulfanyl)-5-phenyl-1H-pyrrole-3-carbonitrile

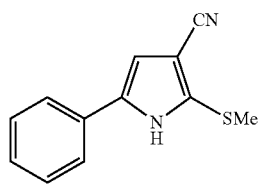 [SMILES: CSc1[nH]c(-c2ccccc2)cc1C#N]

(2-Phenyl-2-oxoethyl)propanedinitrile (2.0 g, 10.9 mmol), acetic acid (3.26 g, 54.3 mmol) and methanol (20 ml) were charged in a reactor, 15% aqueous sodium thiomethoxide solution (7.6 g) was added dropwise, and the mixture was heated under reflux for 6 hr. The reaction mixture was cooled to room temperature, and stirred at room temperature for 1 hr and at 0-10° C. for 1 hr. The crystals were collected by filtration, washed with an ice-cooled mixed solution (2 ml) of water/methanol (1:1) and dried under reduced pressure at 50° C. to give the title compound (2.1 g, yield 90%).
¹H-NMR (300 MHz, TMS, DMSO-d₆) δ (ppm): 12.5 (brs, 1H), 7.72-7.69 (m, 2H), 7.43-7.38 (m, 2H), 7.30-7.28 (m, 1H), 6.98 (s, 1H), 2.52 (s, 3H).

Example 10

5-(2-methylphenyl)-2-(methylsulfanyl)-1H-pyrrole-3-carbonitrile

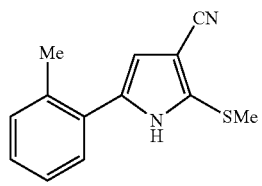 [SMILES: CSc1[nH]c(-c2ccccc2C)cc1C#N]

[2-(2-Methylphenyl)-2-oxoethyl]propanedinitrile (2.0 g, 10.9 mmol), acetic acid (3.26 g, 54.3 mmol) and methanol (20 ml) were charged in a reactor, 15% aqueous sodium thiomethoxide solution (7.6 g) was added dropwise, and the mixture was heated under reflux for 6 hr. The reaction mixture was cooled to room temperature, and stirred at room temperature for 1 hr and at 0-10° C. for 1 hr. The crystals were collected by filtration, and washed with an ice-cooled mixed solution (2 ml) of water/methanol (1:1). The crystals were dried under reduced pressure at 50° C. to give the title compound (1.8 g, yield 78%).
¹H-NMR (300 MHz, TMS, CDCl₃) δ (ppm): 8.5-8.7 (brs, 1H), 7.2-7.3 (m, 4H), 6.51 (d, J=2.8 Hz, 1H), 2.50 (s, 3H), 2.4 (s, 3H).

mass spectrometry (EI, m/z) 228 [M⁺].
elemental analysis (C₁₃H₁₂N₂S)
Calculated: C, 68.39; H, 5.30; N, 12.27; S, 14.04.
Found: C, 68.30; H, 5.26; N, 12.30; S, 14.11.
melting point 148-149° C.

Example 11

5-tert-butyl-2-(methylsulfanyl)-1H-pyrrole-3-carbonitrile

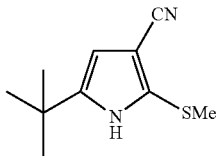

[2-(tert-Butyl)-2-oxoethyl]propanedinitrile (1.0 g, 6.1 mmol), acetic acid (1.1 g, 18.3 mmol) and methanol (10 ml) were charged in a reactor, 15% aqueous sodium thiomethoxide solution (5.7 ml, 12.2 mmol) was added dropwise, and the mixture was heated under reflux for 1 hr. Water and ethyl acetate were added to the reaction mixture, the mixture was partitioned, and the organic layer was washed with saturated aqueous sodium hydrogen carbonate. The organic layer was concentrated, a mixture of methanol and water was added to the concentrated residue, and the mixture was stirred at room temperature for 1 hr. The crystals were collected by filtration, washed with an ice-cooled mixed solution (1 ml) of water/methanol (1:1), and dried under reduced pressure at 50° C. to give the title compound (1.1 g, yield 84%).
¹H-NMR (300 MHz, TMS, CDCl₃) δ (ppm): 8.3 (brs, 1H), 6.18 (d, J=2.9 Hz, 1H), 2.47 (s, 3H), 1.29 (s, 9H).
high resolution mass spectrometry (EI, m/z) (C₁₀H₁₄N₂S)
Calculated 194.0878
Found 194.0877

Example 12

5-(3-methoxyphenyl)-2-(methylsulfanyl)-1H-pyrrole-3-carbonitrile

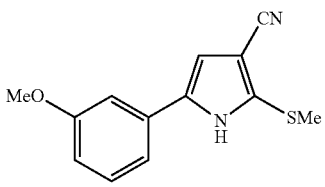 [SMILES: COc1cccc(-c2cc(C#N)c(SC)[nH]2)c1]

[2-(3-Methoxyphenyl)-2-oxoethyl]propanedinitrile (1.0 g, 4.67 mmol), acetic acid (0.84 g, 14.0 mmol) and methanol (10 ml) were charged in a reactor, 15% aqueous sodium thiomethoxide solution (4.35 ml, 9.33 mmol) was added dropwise, and the mixture was heated under reflux for 6 hr. The reaction mixture was cooled to room temperature, water (5 ml) was added, and the mixture was stirred at room temperature for 1 hr and at 0-10° C. for 1 hr. The crystals were collected by filtration, washed with an ice-cooled mixed solution (2 ml) of water/methanol (1:1), and dried under reduced pressure at 50° C. to give the title compound (0.74 g, yield 70%).

$^1$H-NMR (300 MHz, TMS, CDCl$_3$) δ (ppm): 8.90 (brs, 1H), 7.32 (t, J=8.0 Hz, 1H), 7.03 (d, J=7.7 Hz, 1H), 6.96-6.97 (m, 1H), 6.86 (dd, J=5.4 and 2.4 Hz, 1H), 6.68 (d, J=2.8 Hz, 1H), 3.83 (s, 3H), 2.52 (s, 3H).

high resolution mass spectrometry (EI, m/z) (C$_{13}$H$_{12}$N$_2$OS)

Calculated 244.0670
Found 244.0664
melting point 112-113° C.

Example 13

5-(4-bromophenyl)-2-(methylsulfanyl)-1H-pyrrole-3-carbonitrile

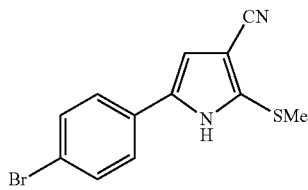 [SMILES: CSc1[nH]c(-c2ccc(Br)cc2)cc1C#N]

[2-(4-Bromophenyl)-2-oxoethyl]propanedinitrile (1.5 g, 5.70 mmol), acetic acid (1.7 g, 28.5 mmol) and methanol (15 ml) were charged in a reactor, 15% aqueous sodium thiomethoxide solution (10.7 ml, 22.8 mmol) was added dropwise, and the mixture was heated under reflux for 5 hr. The reaction mixture was cooled to room temperature, and the mixture was stirred at room temperature for 1 hr and at 0-10° C. for 1 hr. The crystals were collected by filtration, washed with an ice-cooled mixed solution (2 ml) of water/methanol (1:1), and dried under reduced pressure at 50° C. to give the title compound (1.14 g, yield 68%).

$^1$H-NMR (300 MHz, TMS, CDCl$_3$) δ (ppm): 8.7 (brs, 1H), 7.54 (d, J=8.6 Hz, 2H), 7.30 (d, J=6.7 Hz, 2H), 6.69 (d, J=2.3 Hz, 1H), 2.54 (s, 3H).

high resolution mass spectrometry (EI, m/z) (C$_{12}$H$_9$BrN$_2$S)

Calculated 291.9670
Found 291.9684

Example 14

2-(methylsulfanyl)-5-naphthalen-2-yl-1H-pyrrole-3-carbonitrile

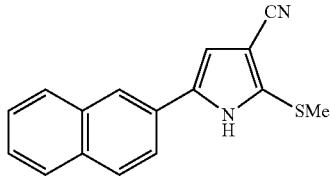 [SMILES: CSc1[nH]c(-c2ccc3ccccc3c2)cc1C#N]

(2-Naphthalen-2-yl-2-oxoethyl)propanedinitrile (1.0 g, 4.25 mmol), acetic acid (1.27 g, 21.3 mmol) and methanol (20 ml) were charged in a reactor, 15% aqueous sodium thiomethoxide solution (9.8 ml, 21.3 mmol) was added dropwise, and the mixture was heated under reflux for 5 hr. The reaction mixture was cooled to room temperature, and stirred at room temperature for 1 hr and at 0-10° C. for 1 hr. The crystals were collected by filtration, washed with an ice-cooled mixed solution (2 ml) of water/methanol (1:1), and dried under reduced pressure at 50° C. to give the title compound (0.97 g, yield 86%).

$^1$H-NMR (300 MHz, TMS, CDCl$_3$) δ (ppm): 8.86 (brs, 1H), 7.83-7.90 (m, 4H), 7.47-7.59 (m, 3H), 6.82 (d, J=2.7 Hz, 1H), 2.56 (s, 3H).

high resolution mass spectrometry (EI, m/z) (C$_{16}$H$_{12}$N$_2$S)

Calculated 264.0721
Found 264.0715

Example 15

(1) 5-(4-fluorophenyl)-2-(methylsulfanyl)-1H-pyrrole-3-carbonitrile

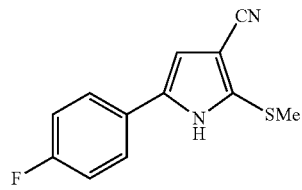 [SMILES: CSc1[nH]c(-c2ccc(F)cc2)cc1C#N]

[2-(4-Fluorophenyl)-2-oxoethyl]propanedinitrile (4.0 g, 19.8 mmol), acetic acid (6.0 g, 99.0 mmol) and methanol (40 ml) were charged in a reactor, 15% aqueous sodium thiomethoxide solution (14.0 ml, 29.7 mmol) was added dropwise, and the mixture was heated under reflux for 6 hr. The reaction mixture was cooled to room temperature, and stirred at room temperature for 1 hr and at 0-10° C. for 1 hr. The crystals were collected by filtration, washed with an ice-cooled mixed solution (2 ml) of water/methanol (1:1), and dried under reduced pressure at 50° C. to give the title compound (3.6 g, yield 78%).

$^1$H-NMR (300 MHz, TMS, DMSO-d$_6$) δ (ppm): 12.5 (brs, 1H), 7.77-7.72 (m, 2H), 7.26 (t, J=8.9 Hz, 2H), 6.96 (s, 1H), 2.51 (s, 3H).

elemental analysis (C$_{12}$H$_9$FN$_2$S)

Calculated: C, 62.05; H, 3.91; N, 12.06; S, 13.80; F, 8.18.
Found: C, 61.90; H, 3.75; N, 12.30; S, 13.79; F, 8.17.
melting point 187-188° C.

(2) 5-(4-fluorophenyl)-2-(methylsulfonyl)-1H-pyrrole-3-carbonitrile

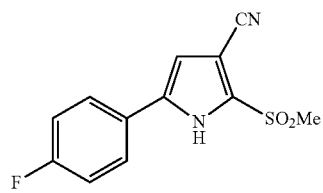

Under ice-cooling, to a solution of 5-(4-fluorophenyl)-2-(methylsulfanyl)-1H-pyrrole-3-carbonitrile (2 g, 8.61 mmol) in ethyl acetate (20 ml) was added m-chloroperbenzoic acid (3.26 g, 19 mmol), and the mixture was stirred at room temperature for 4 hr. The reaction mixture was washed successively with aqueous sodium sulfite solution, saturated aqueous sodium hydrogen carbonate and water. The organic layer was concentrated to give the title compound (2.0 g, yield 88%).

Example 16

2-[(2,4-dichlorophenyl)sulfanyl]-5-phenyl-1H-pyrrole-3-carbonitrile

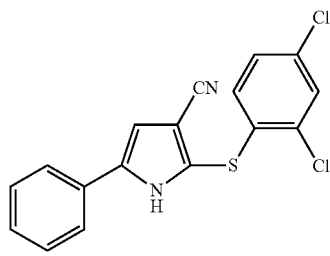 [SMILES: N#Cc1cc(-c2ccccc2)[nH]c1Sc1ccc(Cl)cc1Cl]

(2-Phenyl-2-oxoethyl)propanedinitrile (1.0 g, 5.43 mmol), triethylamine (0.08 ml, 0.543 mmol), methanol (10 ml) and 2,4-dichlorobenzenethiol (1.46 g, 8.15 mmol) were charged in a reactor, and the mixture was stirred at 40° C. for 4 hr. The mixture was allowed to cool and stirred at room temperature for 1 hr. The crystals were collected by filtration, and washed with an ice-cooled mixed solution (1 ml) of water/methanol (1:1). The crystals were dried under reduced pressure at 50° C. to give the title compound (1.46 g, yield 78%).

$^1$H-NMR (300 MHz, TMS, CDCl$_3$) δ (ppm): 9.0 (brs, 1H), 7.48-7.42 (m, 6H), 7.15-7.14 (m, 1H), 6.92 (d, J=8.5 Hz, 1H), 6.84 (d, J=2.8 Hz, 1H).

mass spectrometry (EI, m/z) 344 [M$^+$].
high resolution mass spectrometry (C$_{17}$H$_{10}$C$_{12}$N$_2$S)
Calculated 343.9942
Found 343.9944
melting point 169.0-170.0° C.

Example 17

2-(naphthalen-2-ylsulfanyl)-5-phenyl-1H-pyrrole-3-carbonitrile

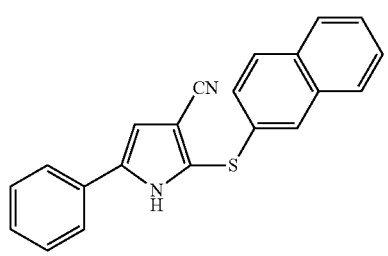 [SMILES: N#Cc1cc(-c2ccccc2)[nH]c1Sc1ccc2ccccc2c1]

(2-Phenyl-2-oxoethyl)propanedinitrile (1.0 g, 5.43 mmol), triethylamine (0.08 ml, 0.543 mmol), methanol (10 ml) and 2-naphthalenethiol (1.3 g, 8.15 mmol) were charged in a reactor, and the mixture was stirred at 40° C. for 0.5 hr. Water (2 ml) was added, and the mixture was stirred at room temperature for 1 hr. The crystals were collected by filtration, washed with an ice-cooled mixed solution (1 ml) of water/methanol (1:1), and dried under reduced pressure at 50° C. to give the title compound (0.63 g, yield 35%).

$^1$H-NMR (300 MHz, TMS, CDCl$_3$) δ (ppm): 9.0 (brs, 1H), 7.8-7.3 (m, 12H), 6.80 (d, J=2.8 Hz, 1H).

high resolution mass spectrometry (EI, m/z) (C$_{21}$H$_{14}$N$_2$S)
Calculated 326.0878
Found 326.0883
melting point 93.0-94.4° C.

Example 18

2-[(2-aminophenyl)sulfanyl]-5-phenyl-1H-pyrrole-3-carbonitrile

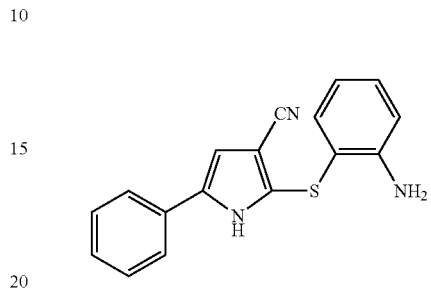

(2-Phenyl-2-oxoethyl)propanedinitrile (5.0 g, 27.1 mmol), triethylamine (0.4 ml, 2.71 mmol), methanol (50 ml) and o-aminobenzenethiol (5.0 ml, 40.7 mmol) were charged in a reactor, and the mixture was stirred at 40° C. for 1 hr. The reaction mixture was concentrated, and the concentrate was purified by silica gel column chromatography to give the title compound (2.3 g, yield 29%).

$^1$H-NMR (300 MHz, TMS, CDCl$_3$) δ (ppm): 9.60 (brs, 1H), 7.56-7.53 (m, 1H), 7.37-7.35 (m, 4H), 7.27-7.20 (m, 2H), 6.85-6.60 (m, 2H), 6.60 (d, J=2.9 Hz, 1H), 4.5-3.50 (br, 2H).

high resolution mass spectrometry (EI, m/z) (C$_{17}$H$_{13}$N$_3$S)
Calculated 291.0830
Found 291.0826
melting point 159.0-160.0° C.

Example 19

2-[(2-bromophenyl)sulfanyl]-5-phenyl-1H-pyrrole-3-carbonitrile

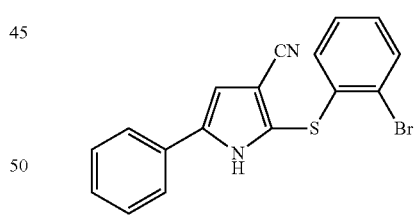

(2-Phenyl-2-oxoethyl)propanedinitrile (5.0 g, 27.1 mmol), triethylamine (0.4 ml, 2.71 mmol), methanol (50 ml) and o-bromobenzenethiol (5.0 ml, 40.7 mmol) were charged in a reactor, and the mixture was stirred at 40° C. for 1 hr. The mixture was allowed to cool, and stirred at room temperature for 1 hr. The crystals were collected by filtration, washed with an ice-cooled mixed solution (5 ml) of water/methanol (1:1), and dried under reduced pressure at 50° C. to give the title compound (6.9 g, yield 72%).

$^1$H-NMR (300 MHz, TMS, CDCl$_3$) δ (ppm): 9.2 (brs, 1H), 7.55-7.40 (m, 6H), 7.19-7.06 (m, 2H), 6.90-6.86 (m, 1H), 6.81 (d, J=2.8 Hz, 1H).

mass spectrometry (EI, m/z) 354 [M$^+$]
high resolution mass spectrometry (C$_{17}$H$_{11}$BrN$_2$S)

$^1$H-NMR (300 MHz, TMS, DMSO-d$_6$) δ (ppm): 7.90-7.85 (m, 2H), 7.32 (t, J=8.9 Hz, 2H), 7.23 (s, 1H), 3.34 (s, 3H).

Calculated 353.9826
Found 353.9816
melting point 126.0-127.0° C.

Example 20

2-[(3-bromophenyl)sulfanyl]-5-phenyl-1H-pyrrole-3-carbonitrile

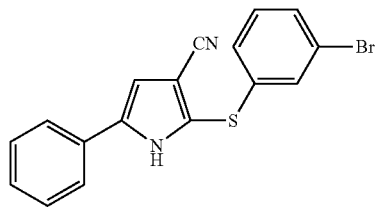 [SMILES: N#Cc1cc(-c2ccccc2)[nH]c1Sc1cccc(Br)c1]

(2-Phenyl-2-oxoethyl)propanedinitrile (1.0 g, 5.43 mmol), triethylamine (0.08 ml, 0.543 mmol), methanol (10 ml) and m-bromobenzenethiol (1.46 g, 8.15 mmol) were charged in a reactor, and the mixture was stirred at 40° C. for 4 hr. The mixture was allowed to cool, and stirred at room temperature for 1 hr. The crystals were collected by filtration, washed with an ice-cooled mixed solution (1 ml) of water/methanol (1:1), and dried under reduced pressure at 50° C. to give the title compound (1.6 g, yield 80%).

$^1$H-NMR (300 MHz, TMS, CDCl$_3$) δ (ppm): 9.0 (brs, 1H), 7.49-7.42 (m, 4H), 7.35-7.33 (m, 3H), 7.15-7.14 (m, 2H), 6.80 (d, J=2.8 Hz, 1H).
mass spectrometry (EI, m/z) 354 [M$^+$]
high resolution mass spectrometry (C$_{17}$H$_{11}$BrN$_2$S)
Calculated 353.9826
Found 353.9824
melting point 141.0-142.0° C.

Example 21

5-phenyl-2-(pyridin-4-ylsulfanyl)-1H-pyrrole-3-carbonitrile

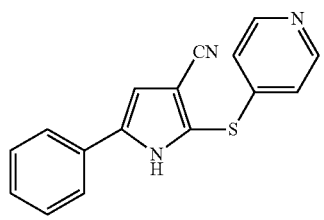 [SMILES: N#Cc1cc(-c2ccccc2)[nH]c1Sc1ccncc1]

(2-Phenyl-2-oxoethyl)propanedinitrile (1.0 g, 5.43 mmol), methanol (10 ml) and 4-mercaptopyridine (1.2 g, 8.15 mmol) were charged in a reactor, and the mixture was heated under reflux for 7 hr. The mixture was allowed to cool and stirred at room temperature for 1 hr. The crystals were collected by filtration, washed with an ice-cooled mixed solution (1 ml) of water/methanol (1:1), and dried under reduced pressure at 50° C. to give the title compound (1.2 g, yield 80%).

$^1$H-NMR (300 MHz, TMS, DMSO-d$_6$) δ (ppm): 13.0 (brs, 1H), 8.43 (d, J=6.2 Hz, 2H), 7.78 (d, J=7.2 Hz, 2H), 7.47-7.29 (m, 4H), 7.05 (d, J=6.5 Hz, 2H).
high resolution mass spectrometry (EI, m/z) (C$_{16}$H$_{11}$N$_3$S)
Calculated 277.0674
Found 277.0678
melting point 172-174° C.

Example 22

2-[(4-aminophenyl)sulfanyl]-5-phenyl-1H-pyrrole-3-carbonitrile

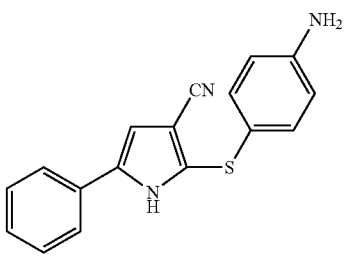

(2-Phenyl-2-oxoethyl)propanedinitrile (1.0 g, 5.43 mmol), methanol (10 ml) and p-aminobenzenethiol (1.26 g, 8.15 mmol) were charged in a reactor, and the mixture was heated under reflux for 4 hr. The mixture was allowed to cool, water (5 ml) was added, and the mixture was stirred at room temperature for 1 hr. The crystals were collected by filtration, washed with an ice-cooled mixed solution (1 ml) of water/methanol (1:1), and dried under reduced pressure at 50° C. to give the title compound (1.05 g, yield 66%).

$^1$H-NMR (300 MHz, TMS, DMSO-d$_6$) δ (ppm): 7.76 (d, J=7.2 Hz, 2H), 7.44 (t, J=7.5 Hz, 2H), 7.32 (t, J=7.4 Hz, 1H), 7.21 (d, J=8.6 Hz, 2H), 7.06 (s, 1H), 6.57 (d, J=8.6 Hz, 2H), 5.40 (s, 2H).
elemental analysis (C$_{17}$H$_{13}$N$_3$S)
Calculated: C, 70.08; H, 4.50; N, 14.42; S, 11.00.
Found: C, 69.93; H, 4.43; N, 14.49; S, 11.05.
melting point 146-147° C.

Example 23

2-[(2-fluorophenyl)sulfanyl]-5-phenyl-1H-pyrrole-3-carbonitrile

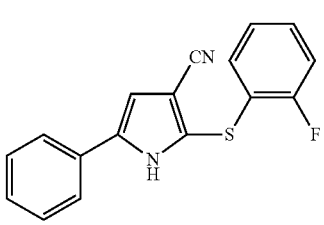 [SMILES: N#Cc1cc(-c2ccccc2)[nH]c1Sc1ccccc1F]

(2-Phenyl-2-oxoethyl)propanedinitrile (1.0 g, 5.43 mmol), triethylamine (0.08 ml, 0.543 mmol), methanol (10 ml) and 2-fluorobenzenethiol (1.04 g, 8.15 mmol) were charged in a reactor, and the mixture was stirred at 40° C. for 4 hr. The mixture was allowed to cool, and stirred at room temperature for 1 hr. The crystals were collected by filtration, washed with an ice-cooled mixed solution (1 ml) of water/methanol (1:1), and dried under reduced pressure at 50° C. to give the title compound (1.1 g, yield 69%).

$^1$H-NMR (300 MHz, TMS, DMSO-d$_6$) δ (ppm): 12.9 (brs, 1H), 7.77 (d, J=7.2 Hz, 2H), 7.43 (t, J=7.1 Hz, 2H), 7.34-7.29 (m, 3H), 7.21-7.17 (m, 2H), 6.93 (t, J=7.7 Hz, 1H).

mass spectrometry (EI, m/z) 294 [M+].
high resolution mass spectrometry ($C_{17}H_{11}FN_2S$)
Calculated 294.0627
Found 294.0620
melting point 152-153° C.

Example 24

2-[(4-nitrophenyl)sulfanyl]-5-phenyl-1H-pyrrole-3-carbonitrile

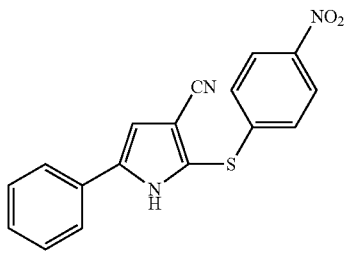 [SMILES: N#Cc1cc(-c2ccccc2)[nH]c1Sc1ccc([N+](=O)[O-])cc1]

(2-Phenyl-2-oxoethyl)propanedinitrile (1.0 g, 5.43 mmol), triethylamine (0.08 ml, 0.543 mmol), methanol (10 ml) and 4-nitrobenzenethiol (1.46 g, 8.15 mmol) were charged in a reactor, and the mixture was stirred at 40° C. for 4 hr. The mixture was allowed to cool and stirred at room temperature for 1 hr. The crystals were collected by filtration, washed with an ice-cooled mixed solution (1 ml) of water/methanol (1:1), and dried under reduced pressure at 50° C. to give the title compound (1.7 g, yield 80%).
$^1$H-NMR (300 MHz, TMS, DMSO-$d_6$) δ (ppm): 13.1 (brs, 1H), 8.20 (d, J=9.0 Hz, 2H), 7.78 (d, J=7.2 Hz, 2H), 7.45 (t, J=6.5 Hz, 2H), 7.33-7.30 (m, 4H).
high resolution mass spectrometry (EI, m/z) ($C_{17}H_{11}N_3O_2S$)
Calculated 321.0572
Found 321.0566
melting point 230-231° C.

Example 25

[(3-cyano-5-phenyl-1H-pyrrol-2-yl)sulfanyl]acetic acid

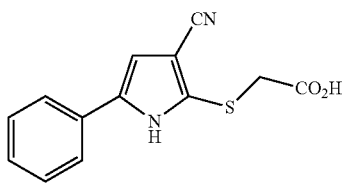 [SMILES: N#Cc1cc(-c2ccccc2)[nH]c1SCC(=O)O]

(2-Phenyl-2-oxoethyl)propanedinitrile (1.0 g, 54.3 mmol), methanol (150 ml) and thioglycolic acid (6.0 g, 52.6 mmol) were charged in a reactor, and the mixture was heated under reflux for 0.5 hr. The mixture was allowed to cool and stirred at room temperature for 0.5 hr and under ice-cooling for 0.5 hr. The crystals were collected by filtration. The wet crystals were washed with ethyl acetate (60 ml), and dried under reduced pressure at 50° C. to give the title compound (8.8 g, yield 60%).

$^1$H-NMR (300 MHz, TMS, DMSO-$d_6$) δ (ppm): 7.60 (d, J=8.0 Hz, 2H), 7.39 (t, J=7.6 Hz, 2H), 7.26-7.21 (m, 1H), 6.66 (s, 1H), 2.51 (s, 2H).
high resolution mass spectrometry (FAB) ($C_{13}H_{10}N_2O_2S$)
Calculated 257.0835 [M-H]$^-$
Found 257.0390 [M-H]$^-$

Example 26

4-(2-fluorophenyl)-2-(iminomethyl)-4-oxobutanenitrile

[2-(2-Fluorophenyl)-2-oxoethyl]propanedinitrile (3.00 g, 14.8 mmol) and THF (30 ml) were weighed, placed in a 50 ml flask and dissolved. The mixture was purged with an inert gas, 5% Pd—C (1.20 g, corresponding to 2 mol % based on Pd) was added, and washed with THF (5 ml). Then, the mixture was purged with hydrogen, and reacted at room temperature for 4 hr (catalytic reduction was performed until the starting material was less than 2%). The catalyst was filtered off, and washed with THF (15 ml), and concentrated to dryness under reduced pressure to give a crude product (3.32 g) of the title compound. Therefrom 2.44 g was suspended in ethyl acetate (5 ml)/n-hexane (5 ml), and the suspension was stirred for 0.5 hr. The suspension was suction filtered, washed with ethyl acetate (2 ml)/n-hexane (2 ml), and dried under reduced pressure at 50° C. to give the title compound (1.47 g, yield 65.9%).
$^1$H-NMR (300 MHz, DMSO-$d_6$) δ (ppm): 3.66 (d, J=2.3 Hz, 2H), 6.37 (m, 2H), 6.79 (t, J=11.1 Hz, 1H), 7.28-7.35 (m, 2H), 7.62-7.64 (m, 1H), 7.77-7.83 (m, 1H).
elemental analysis ($C_{11}H_9N_2OF$)
Calculated: C, 64.70; H, 4.44; N, 13.72; O, 7.84; F, 9.30.
Found: C, 64.78; H, 4.43; N, 13.66.
melting point 119.5-122.5° C.

Example 27

4-naphthalen-2-yl-2-(iminomethyl)-4-oxobutanenitrile

The reaction was performed by an operation similar to that in Example 26 and using (2-naphthalen-2-yl-2-oxoethyl)propanedinitrile (700 mg), and concentrated under reduced pressure. Ethyl acetate (10 ml) was added to the concentrate, and the mixture was stirred for 15 min. The crystals were collected by suction filtration, washed with ethyl acetate (2 ml), and dried under reduced pressure at 50° C. for 2 hr to give the title compound (617 mg, yield 61.2%).
$^1$H-NMR (300 MHz, DMSO-$d_6$) δ (ppm): 3.91 (s, 14/10H), 3.98 (s, 6/10H), 6.40 (brd, J=11.0 Hz, 14/10H), 6.55 (brd, J=11.2 Hz, 6/10H), 6.91 (t, J=11.0 Hz, 7/10H), 7.03 (t, J=11.2 Hz, 3/10H), 7.57-7.67 (m, 20/10H), 7.91-8.00 (m, 30/10H), 8.09 (d, J=7.5 Hz, 10/10H), 8.68 (brs, 10/10H).
elemental analysis ($C_{15}H_{12}N_2O$)
Calculated: C, 76.25; H, 5.12; N, 11.86; O, 6.77.
Found: C, 76.13; H, 5.19; N, 11.77.
melting point 154.0-157.0° C.

Example 28

4-(4-methoxyphenyl)-2-(iminomethyl)-4-oxobutanenitrile

The reaction was performed by an operation similar to that in Example 26 and using [2-(4-methoxyphenyl)-2-oxoethyl]propanedinitrile (5.00 g) to give the title compound (6.14 g). Ethyl acetate (3 ml) was added to 0.95 g thereof, and the mixture was stirred at room temperature for 0.5 hr. The crystals were collected by suction filtration, washed with ethyl acetate (2 ml), and dried under reduced pressure at 50° C. for 2 hr to give a further purified title compound (0.24 g).

$^1$H-NMR (300 MHz, DMSO-d$_6$) δ (ppm): 3.67 (s, 12/7H), 3.73 (s, 2/7H), 3.82 (s, 21/7H), 6.36 (brd, J=11.0 Hz, 12/7H), 6.45 (brd, J=11.0 Hz, 2/7H), 6.80 (t, J=11.0 Hz, 6/7H), 6.94 (t, J=11.0 Hz, 1/7H), 7.00-7.05 (m, 14/7H), 7.93 (d, J=8.9 Hz, 14/7H).

elemental analysis (C$_{12}$H$_{12}$N$_2$O$_2$)
Calculated: C, 66.65; H, 5.59; N, 12.96; O, 14.79.
Found: C, 66.61; H, 5.44; N, 13.09.
melting point 133.5-134.5° C.

Example 29

4-(4-methylphenyl)-2-(iminomethyl)-4-oxobutanenitrile

The reaction was performed by an operation similar to that in Example 26 and using [2-(4-methylphenyl)-2-oxoethyl]propanedinitrile (980 mg) to give the title compound (867 mg, yield 87.6%). Ethyl acetate (4 ml) was added thereto, and the mixture was stirred at room temperature for 1 hr. The crystals were collected by suction filtration, washed with ethyl acetate (2 ml), and dried under reduced pressure at room temperature for 2 hr to give a further purified title compound (345 mg).

$^1$H-NMR (300 MHz, DMSO-d$_6$) δ (ppm): 2.35 (s, 12/4H), 3.70 (s, 6/4H), 3.76 (s, 2/4H), 6.31 (brd, J=11.1 Hz, 6/4H), 6.45 (brd, J=11.1 Hz, 2/4H), 6.81 (t, J=11.1 Hz, 3/4H), 6.94 (t, J=11.1 Hz, 1/4H), 7.30 (d, J=8.1 Hz, 8/4H), 7.85 (d, J=8.1 Hz, 8/4H).

elemental analysis (C$_{12}$H$_{12}$N$_2$O)
Calculated: C, 71.98; H, 6.04; N, 13.99; O, 7.99.
Found: C, 71.94; H, 6.08; N, 13.95.
melting point 158.0-160.0° C.

Example 30

4-(2-methylphenyl)-2-(iminomethyl)-4-oxobutanenitrile

The reaction was performed by an operation similar to that in Example 26 and using [2-(2-methylphenyl)-2-oxoethyl]propanedinitrile (1.00 g). The THF solution was concentrated to dryness under reduced pressure. Ethyl acetate (2 ml) was added thereto, and the mixture was stirred at room temperature for 0.5 hr. The crystals were collected by suction filtration, washed with ethyl acetate (1 ml), and dried under reduced pressure at 50° C. for 2 hr to give a further purified title compound (498 mg, yield 49.3%).

$^1$H-NMR (300 MHz, DMSO-d$_6$) δ (ppm): 2.39 (s, 15/6H), 2.41 (s, 3/6H), 3.66 (s, 10/6H), 3.73 (s, 2/6H), 6.37 (brd, J=11.0 Hz, 10/6H), 6.50 (brd, J=11.0 Hz, 2/6H), 6.82 (t, J=11.0 Hz, 5/6H), 6.96 (t, J=11.0 Hz, 1/6H), 7.27-7.34 (m, 12/6H), 7.39-7.44 (m, 6/6H), 7.75 (d, J=7.7 Hz, 5/6H), 7.82 (d, J=7.8 Hz, 1/6H).

elemental analysis (C$_{12}$H$_{12}$N$_2$O)
Calculated: C, 71.98; H, 6.04; N, 13.99; O, 7.99.
Found: C, 72.06; H, 6.05; N, 14.00.
melting point 111.0-114.0° C.

Example 31

2-(iminomethyl)-4-oxo-4-phenylbutanenitrile

The reaction was performed by an operation similar to that in Example 29 and using (2-oxo-2-phenylethyl)propanedinitrile (1.82 g) to give the title compound (804 mg, yield 43.7%).

$^1$H-NMR (300 MHz, DMSO-d$_6$) δ (ppm): 3.75 (s, 10/8H), 3.81 (s, 6/8), 6.34 (brd, J=11.0 Hz, 10/8H), 6.47 (d, J=11.0 Hz, 6/8H), 6.82 (t, J=11.0 Hz, 5/8H), 6.96 (t, J=11.0 Hz, 3/8H), 7.48-7.56 (m, 16/8H), 7.59-7.65 (m, 8/8H), 7.94-7.98 (m, 16/8H).

elemental analysis (C$_{11}$H$_{10}$N$_2$O)
Calculated: C, 70.95; H, 5.41; N, 15.04; O, 8.59.
Found: C, 70.97; H, 5.34; N, 15.14.
melting point 89.0-90.0° C.

Example 32

5-(4-methylphenyl)-1H-pyrrole-3-carbonitrile

To 4-(4-methylphenyl)-2-(iminomethyl)-4-oxobutanenitrile (217 mg) were added THF (1 ml) and acetic acid (0.44 ml), and the mixture was reacted at the outer temperature of 50° C. The reaction mixture was extracted with ethyl acetate, and washed successively with aqueous sodium hydrogen carbonate solution and water. Ethyl acetate was concentrated under reduced pressure. The residue was crystallized from ethyl acetate (1 ml)/n-hexane (7 ml). The crystals were collected by suction filtration, washed with ethyl acetate (0.2 ml)/n-hexane (1.6 ml), and dried under reduced pressure at 45° C. for 3 hr to give the title compound (110 mg, yield 55.7%).

$^1$H-NMR (300 MHz, DMSO-d$_6$) δ (ppm): 2.27 (s, 3H), 6.84 (dd, J=1.6, 2.9 Hz, 1H), 7.18 (d, J=8.2 Hz, 2H), 7.54 (d, J=8.2 Hz, 2H), 7.65 (dd, J=1.6, 2.3 Hz, 1H), 12.13 (brs, 1H).

elemental analysis (C$_{12}$H$_{10}$N$_2$)
Calculated: C, 79.10; H, 5.53; N, 15.37.
Found: C, 79.00; H, 5.47; N, 15.50.
melting point 169.0-171.0° C.

Example 33

5-(2-fluorophenyl)-1H-pyrrole-3-carbonitrile

[2-(2-Fluorophenyl)-2-oxoethyl]propanedinitrile (10.0 g, 49.46 mmol) and THF (95 ml) were weighed, placed in a 200 ml flask and dissolved. The mixture was purged with an inert gas, 5% Pd—C (4.0 g, corresponding to 2 mol % based on Pd) was added, and washed with THF (5 ml). Then, the mixture was purged with hydrogen and reacted at room temperature. Catalytic reduction was performed until the starting material became less than 2%. The catalyst was filtered off, and washed twice with THF (20 ml). The THF solution was concentrated under reduced pressure to about 28 g. Acetic acid (20 ml) was added thereto, and the mixture was reacted at the outer temperature of 50° C. for 4 hr. Water (100 ml) was added dropwise to this reaction mixture. The crystals were aged at room temperature, collected by suction filtration, washed with cold aqueous ethanol solution (ethanol:water=1:4, 20 ml), and dried under reduced pressure at 50° C. to give 5-(2-fluorophenyl)-1H-pyrrole-3-carbonitrile (7.38 g).

7.00 g of the obtained 5-(2-fluorophenyl)-1H-pyrrole-3-carbonitrile was suspended in acetic acid (14 ml), and the suspension was stirred at room temperature for 1 hr. The solid was collected by suction filtration, washed with cold aqueous ethanol solution (ethanol:water=1:4, 10 ml), and dried under reduced pressure at 50° C. to give 5-(2-fluorophenyl)-1H-pyrrole-3-carbonitrile (5.96 g, yield 68.2%).

Example 34

5-naphthalen-2-yl-1H-pyrrole-3-carbonitrile (2-Naphthalen-2-yl-2-oxoethyl)propanedinitrile (2.00 g) was dissolved in THF (50 ml). The mixture was purged with an inert gas, 5% Pd—C (1.2 g) was added, and the mixture was purged with an inert gas. Then, the mixture was purged with hydrogen, and reacted at room temperature for 4.5 hr. Catalytic reduction was performed until the starting material became less than 2%. The catalyst was filtered off and washed with THF. The filtrate was concentrated under reduced pressure. Acetic acid (30 ml) was added thereto, and the mixture was reacted at the outer temperature of 50° C. for 4 hr. Ethyl acetate was added, and the mixture was partitioned. The organic layer was washed with water, saturated aqueous sodium hydrogen carbonate and saturated brine in this order. The organic layer was concentrated under reduced pressure to give a residue (1.66 g). This was quantified by HPLC to give the title compound (1.20 g, yield 65.8%). This was purified by column chromatography (ethyl acetate/n-hexane) to give the title compound (858 mg, yield 46.1%).

$^1$H-NMR (300 MHz, DMSO-$d_6$) δ (ppm): 7.08 (s, 1H), 7.42-7.52 (m, 2H), 7.76-7.93 (m, 5H), 8.20 (s, 1H), 12.40 (brs, 1H).

melting point 200.5-206.5° C.

Example 35

5-(2,4-dimethoxyphenyl)-1H-pyrrole-3-carbonitrile

The reaction was performed by an operation similar to that in Example 34 and using [2-(2,4-dimethoxyphenyl)-2-oxoethyl]propanedinitrile (700 mg). Quantification by HPLC gave the title compound (493 mg, yield 75.4%). Purification by column chromatography (ethyl acetate/n-hexane) gave the title compound (410 mg, yield 62.7%).

$^1$H-NMR (300 MHz, DMSO-$d_6$) δ (ppm): 3.77 (s, 3H), 3.85 (s, 3H), 6.57 (d, J=8.5 Hz, 1H), 6.62 (s, 1H), 6.75 (s, 1H), 7.50 (d, J=8.5 Hz, 1H), 7.56 (s, 1H), 11.68 (brs, 1H).

elemental analysis ($C_{13}H_{12}N_2O_2$)
Calculated: C, 68.41; H, 5.30; N, 12.27; O, 14.02.
Found: C, 68.44; H, 5.31; N, 12.43.
melting point 129.0-130.0° C.

Example 36

5-(4-methoxyphenyl)-1H-pyrrole-3-carbonitrile

The reaction was performed by an operation similar to that in Example 34 and using [2-(4-methoxyphenyl)-2-oxoethyl]propanedinitrile (5.0 g). Quantification by HPLC gave the title compound (3.4 g, yield 87.3%). This was recrystallized from ethyl acetate/n-hexane (1:2) to give the title compound (3.1 g, yield 80.4%).

$^1$H-NMR (300 MHz, DMSO-$d_6$) δ (ppm): 3.75 (s, 3H), 6.77 (s, 1H), 6.95 (d, J=8.7 Hz, 2H), 7.58 (d, J=8.7 Hz, 2H), 7.62 (d, J=0.6 Hz, 1H), 12.07 (brs, 1H).

elemental analysis ($C_{12}H_{10}N_2O$)
Calculated: C, 72.71; H, 5.08; N, 14.13; O, 8.07.
Found: C, 72.48; H, 5.06; N, 14.11.
melting point 185.0-186.0° C.

Example 37

5-(4-methylphenyl)-1H-pyrrole-3-carbonitrile

The reaction was performed by an operation similar to that in Example 34 and using [2-(4-methylphenyl)-2-oxoethyl]propanedinitrile (5.0 g). Quantification by HPLC gave the title compound (3.4 g, yield 73.8%).

Example 38

5-(2-methylphenyl)-1H-pyrrole-3-carbonitrile

The reaction was performed by an operation similar to that in Example 34 and using [2-(2-methylphenyl)-2-oxoethyl]propanedinitrile (1.00 g) to give the title compound (535 mg, yield 63.1%).

$^1$H-NMR (300 MHz, DMSO-$d_6$) δ (ppm): 2.37 (s, 3H), 6.63 (d, J=1.4 Hz, 1H), 7.23-7.31 (m, 3H), 7.38-7.41 (m, 1H), 7.71 (d, J=1.4 Hz, 1H), 11.98 (brs, 1H).

elemental analysis ($C_{12}H_{10}N_2$)
Calculated: C, 79.10; H, 5.53; N, 15.37.
Found: C, 78.94; H, 5.55; N, 15.26.
melting point 151.0-152.5° C.

Example 39

5-phenyl-1H-pyrrole-3-carbonitrile

The reaction was performed by an operation similar to that in Example 34 and using (2-oxo-2-phenylethyl)propanedinitrile (4.5 g). Quantification by HPLC gave the title compound (2.4 g, yield 58.3%).

$^1$H-NMR (300 MHz, DMSO-$d_6$) δ (ppm): 6.92 (dd, J=1.6, 2.3 Hz, 1H), 7.23-7.26 (m, 1H), 7.35-7.40 (m, 2H), 7.65 (s, 1H), 7.64-7.70 (m, 2H), 12.21 (brs, 1H).

elemental analysis ($C_{11}H_8N_2$)
Calculated: C, 78.55; H, 4.79; N, 16.66.
Found: C, 78.50; H, 4.78; N, 16.69.
melting point 150.0-151.0° C.

Example 40

5-(4-fluorophenyl)-1H-pyrrole-3-carbonitrile

The reaction was performed by an operation similar to that in Example 34 and using [2-(4-fluorophenyl)-2-oxoethyl]propanedinitrile (2.00 g). Quantification by HPLC gave the title compound (1.43 g, yield 77.8%).

$^1$H-NMR (300 MHz, DMSO-$d_6$) δ (ppm): 6.88 (dd, J=1.7, 2.2 Hz, 1H), 7.18-7.24 (m, 2H), 7.66-7.71 (m, 3H), 12.20 (brs, 1H).

elemental analysis ($C_{11}H_7N_2F$)
Calculated: C, 70.96; H, 3.78; N, 15.04; F, 10.20.
Found: C, 70.99; H, 3.74; N, 15.16.
melting point 158.4-159.3° C.

Example 41

5-(4-chlorophenyl)-1H-pyrrole-3-carbonitrile

The reaction was performed by an operation similar to that in Example 34 and using [2-(4-chlorophenyl)-2-oxoethyl]propanedinitrile (5.0 g). Quantification by HPLC gave the title compound (2.2 g, yield 48.8%).

$^1$H-NMR (300 MHz, DMSO-$d_6$) δ (ppm): 6.96 (dd, J=1.6, 2.5 Hz, 1H), 7.43 (d, J=8.7 Hz, 2H), 7.65 (s, 1H), 7.67 (d, J=8.7 Hz, 2H), 12.26 (brs, 1H).

elemental analysis ($C_{11}H_7N_2Cl$)
Calculated: C, 65.20; H, 3.47; N, 13.82; Cl, 17.50.
Found: C, 65.45; H, 3.49; N, 13.81.
melting point 174.2-175.1° C.

Example 42

4-methyl-5-phenyl-1H-pyrrole-3-carbonitrile

The reaction was performed by an operation similar to that in Example 34 and using (1-methyl-2-oxo-2-phenylethyl)

propanedinitrile (1.00 g). Quantification by HPLC gave the title compound (624 mg, yield 71.1%).

$^1$H-NMR (300 MHz, DMSO-d$_6$) δ (ppm): 2.23 (s, 3H), 7.27-7.30 (m, 1H), 7.39-7.50 (m, 4H), 7.59 (d, J=2.3 Hz, 1H), 11.88 (brs, 1H).

elemental analysis (C$_{12}$H$_{10}$N$_2$)
Calculated: C, 79.10; H, 5.53; N, 15.37.
Found: C, 79.02; H, 5.50; N, 15.42.
melting point 130.0-134.5° C. dec.

Example 43

4,5-diphenyl-1H-pyrrole-3-carbonitrile

The reaction was performed by an operation similar to that in Example 34 and using (2,2-diphenylethyl-2-oxo)propanedinitrile (1.00 g). Quantification by HPLC gave the title compound (556 mg, yield 45.2%).

$^1$H-NMR (300 MHz, DMSO-d$_6$) δ (ppm): 7.10-7.38 (m, 10H), 7.80 (d, J=3.1 Hz, 1H), 12.21 (brs, 1H).

elemental analysis (C$_{17}$H$_{12}$N$_2$)
Calculated: C, 83.58; H, 4.94; N, 11.47.
Found: C, 83.30; H, 5.08; N, 11.33.
melting point 163.0-166.0° C.

Example 44

5-tert-butyl-1H-pyrrole-3-carbonitrile

The reaction was performed by an operation similar to that in Example 34 and using (3,3-dimethyl-2-oxobutyl)propanedinitrile (1.00 g). Quantification by HPLC gave the title compound (682 mg, yield 75.5%). This was further purified by column chromatography (ethyl acetate/n-hexane) to give the title compound (0.54 g, yield 59.4%).

$^1$H-NMR (300 MHz, DMSO-d$_6$) δ (ppm): 1.20 (s, 9H), 6.07 (dd, J=2.3, 1.8 Hz, 1H), 7.42 (dd, J=2.9, 1.8 Hz, 1H), 11.46 (brs, 1H).

elemental analysis (C$_9$H$_{12}$N$_2$)
Calculated: C, 72.94; H, 8.16; N, 18.90.
Found: C, 72.68; H, 8.24; N, 19.03.
melting point 101.5-103.0° C.

Example 45

5-(2-fluorophenyl)-1H-pyrrole-3-carbonitrile

N,N-Dimethylacetamide (4 ml), [2-(2-fluorophenyl)-2-oxoethyl]propanedinitrile (500 mg, 2.47 mmol) and triethylamine (5.51 g, 54.41 mmol) were added in a flask, and ice-cooled. Formic acid (2.28 g, 49.46 mmol) was added dropwise while paying attention to heat generation. The mixture was warmed to room temperature, and purged with an inert gas. 5% Pd—C(N.E. CHEMCAT, 500 mg) was added, and the mixture was reacted at room temperature for 2.5 hr. Acetic acid (2 ml) was added to the reaction mixture, and the mixture was reacted at an outer temperature of 50° C. for 1 hr 10 min. The catalyst was filtered off, and washed with THF (about 5 ml). Quantification of the filtrate by HPLC gave the title compound (189 mg, yield 41.0%).

Example 46 methyl 5-(2-fluorophenyl)-1H-pyrrole-3-carboxylate

Methyl 2-cyano-4-(2-fluorophenyl)-4-oxobutanoate (500 mg, 2.13 mmol) was dissolved in THF (5 ml), and 5% Pd/C (50% wet, 200 mg) was added. Under a hydrogen atmosphere, the mixture was stirred at room temperature for 4 hr. The catalyst was filtered off, and washed with THF. The filtrate was concentrated under reduced pressure, THF (10 ml) and acetic acid (10 ml) were added, and the mixture was stirred at room temperature for 1 hr. Quantification of the reaction mixture by HPLC confirmed production of the title compound (249 mg, yield 53.5%).

$^1$H-NMR (300 MHz, CDCl$_3$) δ (ppm): 3.85 (3H, s), 7.01-7.27 (4H, m), 7.49-7.65 (2H, m), 9.30 (1H, brs).

elemental analysis (C$_{12}$H$_{10}$NO$_2$F)
Calculated: C, 65.75; H, 4.60; N, 6.39; O, 14.59; F, 8.66.
Found: C, 65.46; H, 4.62; N, 6.36.
melting point 152.3-152.7° C.

Example 47

[2-(2-Fluorophenyl)-2-oxoethyl]propanedinitrile (2.00 g, 9.89 mmol), acetic acid (30 ml) and THF (15 ml) were weighed and dissolved (under an argon atmosphere). Then, Raney-nickel (0.5 ml) and water (4.5 ml) were weighed and added, and the mixture was purged with hydrogen. This was reacted at room temperature for about 8 hr. Quantification of the filtrate by HPLC gave 5-(2-fluorophenyl)-1H-pyrrole-3-carbonitrile (654 mg, yield 35.6%).

Example 48

[2-(2-Fluorophenyl)-2-oxoethyl]propanedinitrile (2.00 g, 9.89 mmol), acetic acid (22 ml) and THF (22 ml) were weighed and dissolved (under an argon atmosphere). Then, Raney-nickel (0.5 ml) and water (4.5 ml) were weighed and added, and the mixture was purged with hydrogen. This was reacted at room temperature for about 9 hr. Quantification of the filtrate by HPLC gave 5-(2-fluorophenyl)-1H-pyrrole-3-carbonitrile (831 mg, yield 45.2%).

Example 49

[2-(2-Fluorophenyl)-2-oxoethyl]propanedinitrile (2.00 g, 9.89 mmol), acetic acid (6 ml) and THF (22 ml) were weighed and dissolved (under an argon atmosphere). Then, Raney-nickel (0.5 ml) and water (4.5 ml) were weighed and added, and the mixture was purged with hydrogen. This was reacted at room temperature for about 9 hr. Quantification of the filtrate by HPLC gave 5-(2-fluorophenyl)-1H-pyrrole-3-carbonitrile (682 mg, yield 37.1%).

Example 50

[2-(2-Fluorophenyl)-2-oxoethyl]propanedinitrile (2.00 g, 9.89 mmol), N,N-dimethylformamide (10 ml) and ammonium formate (3.2 g) were weighed and dissolved (under an argon atmosphere). Then, 5% Pd—C (600 mg) was added, and the mixture was reacted at room temperature for about 1 hr, and at an outer temperature of 50° C. for about 2 hr. The catalyst was filtered off, and the filtrate was quantified by HPLC to give 5-(2-fluorophenyl)-1H-pyrrole-3-carbonitrile (0.089 g, yield 9.70%).

Example 51

[2-(2-Fluorophenyl)-2-oxoethyl]propanedinitrile (2.00 g, 9.89 mmol) and formic acid (6 ml) were weighed and dissolved (under an argon atmosphere). Then, Raney-nickel (0.5 ml) and water (4.5 ml) were weighed and added, and the mixture was purged with hydrogen. 5% Pd—C (600 mg) was added, and the mixture was reacted at an outer temperature of 50° C. for about 5 hr (triethylamine (0.2 ml), formic acid (3 ml) and 5% Pd—C (600 mg) were added during reaction). The catalyst was filtered off, and the filtrate was quantified by HPLC to give 5-(2-fluorophenyl)-1H-pyrrole-3-carbonitrile (230 mg, yield 24.9%).

Example 52

[2-(2-Fluorophenyl)-2-oxoethyl]propanedinitrile (2.00 g, 9.89 mmol), acetic acid (22 ml) and THF (22 ml) were weighed and dissolved (under an argon atmosphere). Then, Raney-nickel (1 ml) and water (2 ml) were weighed and added, and the mixture was purged with hydrogen. This was reacted at 45-50° C. for about 5 hr. Quantification of the filtrate by HPLC gave 5-(2-fluorophenyl)-1H-pyrrole-3-carbonitrile (718 mg, yield 38.6%) and 5-(2-fluorophenyl)-1H-pyrrole-3-carbaldehyde (277 mg, yield 14.8%).

Example 53

2,2'-disulfanediylbis[5-(2-methylphenyl)-1H-pyrrole-3-carbonitrile]

To a slurry of [2-(2-methylphenyl)-2-oxoethyl]propanedinitrile obtained in Reference Example 4 and methanol were added thioacetic acid (66.6 ml, 932 mmol), triethylamine (13.0 ml, 93.2 mmol) and dimethyl sulfoxide (8.59 ml, 121 mmol), and the mixture was heated under reflux at the internal temperature of about 60° C. for 13 hr. The reaction mixture was gradually cooled to 30° C. or below, further cooled to an internal temperature of 5±5° C. and stirred for 1 hr. The precipitated crystals were collected by filtration, and washed with cold ethanol (62.5 ml). The wet crystals were dried under reduced pressure at 50° C. to give the title compound (56.4 g, yield 57%) as yellow crystals.

melting point 248.0-249.0° C.
$^1$H-NMR (300 MHz, DMSO-$d_6$) δ (ppm): 12.7 (s, 2H), 7.41 (d, J=6.0 Hz, 2H), 7.31-7.26 (m, 6H), 6.78 (d, J=2.4 Hz, 2H), 2.40 (s, 6H).
elemental analysis ($C_{24}H_{18}N_4S_2$)
Calculated: C, 67.58; H, 4.25; N, 13.13; S, 15.03.
Found: C, 67.40; H, 4.20; N, 13.04; S, 14.92.
LC-MS: 426 (M$^+$).

Example 54

5-(2-methylphenyl)-1H-pyrrole-3-carbonitrile

Raney-nickel (139 g), N,N-dimethylformamide (300 ml) and morpholine (15.5 ml, 178 mmol) were added in a four neck flask, and the mixture was stirred under a nitrogen stream at room temperature. While maintaining the internal temperature at 40° C. or below, a solution of 2,2'-disulfanediylbis[5-(2-methylphenyl)-1H-pyrrole-3-carbonitrile] (50 g, 117 mmol) in N,N-dimethylformamide (150 ml) was slowly added dropwise. The dropping funnel was washed with N,N-dimethylformamide (50 ml). The mixture was heated under reflux at the internal temperature of 100-110° C. for 1.5 hr. After cooling to room temperature, Raney-nickel was filtered off, and the residue was washed with ethyl acetate (150 ml). Ethyl acetate (350 ml) and 10% brine (750 ml) were added to the filtrate for extraction and partitioning. The aqueous layer was extracted with ethyl acetate (250 ml, 125 ml, 125 ml). The organic layers were combined, washed with water (1 L) and concentrated to about half amount under reduced pressure. Ethanol (250 ml) was added to the concentrate, and the mixture was concentrated to about 241 g. This operation was repeated 3 times. Water (250 ml) was added while stirring the concentrate with heating at 75-85° C., and the mixture was further stirred at the same temperature for 1 hr. The mixture was gradually cooled to not more than 30° C., further cooled to the internal temperature of 5±5° C., and stirred for 1 hr. The precipitated crystals were collected by filtration, and washed with a cold mixture of ethanol (37.5 ml) and water (37.5 ml). The wet crystals were dried under reduced pressure at 50° C. until a constant weight was reached to give the title compound (35.5 g, yield 83%).

melting point 151-152° C.
$^1$H-NMR (300 MHz, DMSO-$d_6$) δ (ppm): 2.37 (s, 3H), 6.61 (d, J=1.36 Hz, 1H), 7.23-7.31 (m, 3H), 7.38-7.41 (m, 1H), 7.71 (d, J=1.36 Hz, 1H), 11.98 (brs, 1H).
elemental analysis ($C_{12}H_{10}N_2$)
Calculated: C, 79.09; H, 5.52; N, 15.37.
Found: C, 78.94; H, 5.55; N, 15.26.

Example 55

S-[3-cyano-5-(2-methylphenyl)-1H-pyrrol-2-yl]benzenecarbonitrile

[2-(2-Methylphenyl)-2-oxoethyl]propanedinitrile (10 g, 50.4 mmol), thiobenzoic acid (11.2 g, 81.0 mmol), triethylamine (508 mg, 5.04 mmol) and methanol (100 ml) were mixed, and the mixture was stirred at about 60° C. for about 3 hr. Water (10 ml) was added at about 35° C., and the mixture was stirred at room temperature for 1 hr, and at about 10° C. for about 1 hr. The precipitated crystals were collected by filtration, and washed with a mixture of methanol (24 ml) and water (6 ml). The wet crystals were dried under reduced pressure to give the title compound (14.4 g, yield 90%).

$^1$H-NMR (300 MHz, DMSO-$d_6$) δ (ppm): 2.40 (s, 3H), 6.90 (s, 1H), 7.28-7.30 (m, 3H), 7.40-7.43 (m, 1H), 7.65 (t, J=7.6 Hz, 2H), 7.78-7.80 (m, 1H), 8.02-8.05 (m, 2H), 12.6 (brs, 1H)

Example 56

5-(2-methylphenyl)-1H-pyrrole-3-carbonitrile

Raney-nickel (73 g), N,N-dimethylformamide (150 ml) and morpholine (13.0 ml, 149 mmol) were added in a four neck flask, and the mixture was stirred under a nitrogen stream at room temperature. While maintaining the internal temperature at 40° C. or below, a solution of S-[3-cyano-5-(2-methylphenyl)-1H-pyrrol-2-yl]benzenecarbonitrile (31.6 g, 99.2 mmol) in N,N-dimethylformamide (130 ml) was slowly added dropwise. The dropping funnel was washed with N,N-dimethylformamide (30 ml). The mixture was heated under reflux at the internal temperature of 100-110° C. for 1.5 hr. After cooling to room temperature, Raney-nickel was filtered off, and the residue was washed with ethyl acetate (210 ml). Ethyl acetate (210 ml) and 10% brine (750 ml) were added to the filtrate for extraction and partitioning. The aqueous layer was extracted with ethyl acetate (150 ml, 75 ml, 75 ml). The organic layers were combined, washed with water (210 ml) and concentrated under reduced pressure. Ethanol (212 ml) was added to the concentrate, and the mixture was concentrated to about 204 g. This operation was repeated 3 times. Water (210 ml) was added while stirring the concentrate with heating at 75-85° C., and the mixture was further stirred at the same temperature for 1 hr. The mixture was gradually cooled to not more than 30° C., further cooled to the internal temperature of 5±5° C., and stirred for 1 hr. The precipitated crystals were collected by filtration, and washed with a cold mixture of ethanol (4.5 ml) and water (10.5 ml). The wet crystals were dried under reduced pressure at 50° C. until a constant weight was reached to give the title compound (14.1 g, yield 78%).

Example 57

5-(2-methylphenyl)-1-(pyridin-3-ylsulfonyl)-1H-pyrrole-3-carbonitrile 5-(2-Methylphenyl)-1H-pyrrole-3-carbonitrile (35.0 g, 192 mmol), acetonitrile (131 ml), 4-N,N-dimethylaminopyridine (4.69 g, 38.4 mmol) and diisopropylethylamine (269 mmol, 46.1 ml) were added in a four neck flask, and the mixture was stirred at room temperature. While maintaining an internal temperature at 40° C. or below, a solution of 3-pyridinesulfonyl chloride (40.9 g, 230 mmol) in acetonitrile (37 ml) was slowly added dropwise, the dropping funnel was washed with acetonitrile (7 ml). The mixture was reacted at room temperature for 1 hr, and tap water (87.5 ml) was added to the reaction mixture. 0.5 N HCl was added dropwise to adjust to pH 4.5, and the mixture was stirred at room temperature for 1 hr. The precipitated crystals were collected by filtration, and washed with a mixture of acetonitrile (21.2 ml) and water (21.2 ml). The wet crystals were dried under reduced pressure at 50° C. to give the title compound (54.8 g, yield 90%).

$^1$H-NMR (300 MHz, CDCl$_3$) δ (ppm): 8.81 (d, J=1.8 Hz, 1H), 8.52 (d, J=1.8 Hz, 1H), 8.01 (s, 1H), 7.60-7.56 (br, 1H), 7.38-7.18 (m, 4H), 6.88 (d, J=7.5 Hz, 1H), 6.56 (s, 1H), 1.82 (s, 3H).

Example 58

5-(2-methylphenyl)-1-(pyridin-3-ylsulfonyl)-1H-pyrrole-3-carbaldehyde hydrochloride 5-(2-Methylphenyl)-1-(pyridin-3-ylsulfonyl)-1H-pyrrole-3-carbonitrile (123.6 mmol, 40.0 g), tetrahydrofuran (160 ml), acetic acid (240 ml), water (240 ml) and Raney-nickel (32.0 g) were added in a four neck flask, and the mixture was reacted under slightly pressurized hydrogen at 17-25° C. for 9 hr. After completion of the reaction, the catalyst was filtered off, and washed with a mixture of tetrahydrofuran (15 ml), acetic acid (22.5 ml) and water (22.5 ml). The filtrate was extracted with ethyl acetate (400 ml) and tap water (400 ml). The organic layer was washed twice with tap water (200 ml), and partitioned. The organic layer was concentrated under reduced pressure to about 60 g, ethyl acetate (200 ml) was added to the concentrate, and the mixture was concentrated again under reduced pressure to about 60 g. This operation was performed twice in total. Ethyl acetate (300 ml) was added to adjust the liquid amount to about 330 g. To the ethyl acetate solution was slowly added dropwise 4 N hydrochloric acid/ethyl acetate solution (62 ml, 247 mmol) at 25-35° C. After the completion of the dropwise addition, the mixture was stirred at the internal temperature of 50-55° C. for 1 hr. The suspension was cooled to 20-30° C., and stirred at the same temperature for 1 hr, and further at 0-10° C. for 1 hr. The precipitated crystals were collected by filtration, and washed with ethyl acetate (80 ml). The wet crystals were dried under reduced pressure at 50° C. until a constant weight was reached to give the title compound (38 g, yield 85%).

$^1$H-NMR (500 MHz, DMSO-d$_6$) δ (ppm): 1.74 (s, 3H), 6.58 (d, J=1.58 Hz, 1H), 6.83-6.91 (m, 1H), 7.11-7.25 (m, 2H), 7.38 (td, J=7.57, 1.26 Hz, 1H), 7.62 (dd, J=8.20, 4.73 Hz, 1H), 7.85-7.94 (m, 1H), 8.47 (d, J=1.89 Hz, 1H), 8.56 (d, J=1.58 Hz, 1H), 8.91 (dd, J=4.73, 1.58 Hz, 1H), 9.90 (s, 1H), 1H not detected.

Example 59

N-methyl-1-[5-(2-methylphenyl)-1-(pyridin-3-ylsulfonyl)-1H-pyrrol-3-yl]methanamine fumarate Under a nitrogen stream, 40% methylamine methanol solution (21.2 ml, 207 mmol) and methanol (60 ml) were added in a four neck flask, and a solution of 5-(2-methylphenyl)-1-(pyridin-3-ylsulfonyl)-1H-pyrrole-3-carbaldehyde hydrochloride (30 g, 82.7 mmol) in N,N-dimethylformamide (90 ml) was added dropwise at 30° C. or below. The mixture was stirred at about 25° C. for 1 hr, Na$_2$CO$_3$ (8.76 g, 82.7 mmol) was added, and the mixture was further stirred for 1 hr. The mixture was ice-cooled to 0-5° C., a solution of sodium borohydride (1.56 g, 41.3 mmol) in N,N-dimethylformamide (30 ml) was slowly added dropwise at 10° C. or below. The mixture was stirred at 0-5° C. for 1 hr, 2 N hydrochloric acid (200 ml) was added dropwise at 15° C. or below to adjust to pH 2, and the mixture was stirred at room temperature for 1 hr. Ethyl acetate (300 ml) and 12.5% aqueous ammonia (180 ml) were added, and the mixture was stirred at room temperature for 30 min and partitioned. The aqueous layer was extracted with ethyl acetate (180 ml). The organic layers were combined, washed with about 5% brine (180 ml) and partitioned. The organic layer was concentrated to 40 g, ethyl acetate (300 ml) was added and the mixture was concentrated again. This operation was performed twice, and the mixture was concentrated to the total amount of 165 g. N,N-Dimethylformamide (150 ml) was added to the concentrated residue, and the mixture was heated to the internal temperature of 50-60° C. Fumaric acid (9.6 g, 82.7 mmol) was added. The mixture was stirred at the internal temperature of 50-60° C. for 30 min, allowed to cool and stirred at 20-30° C. for 1 hr, and further stirred at 0-10° C. for 1 hr. The precipitated crystals were collected by filtration, and washed with a cold mixture of N,N-dimethylformamide (30 ml) and ethyl acetate (30 ml). The wet crystals were dried under reduced pressure at 50° C. until a constant weight was reached to give the title compound as a crude product (24.5 g, yield 65%).

$^1$H-NMR (300 MHz, DMSO-d$_6$) δ (ppm): 8.88-8.86 (m, 1H), 8.44 (s, 1H), 7.81-7.78 (m, 1H), 7.67 (s, 1H), 7.61-7.56 (m, 1H), 7.34 (t, J=7.5 Hz, 1H), 7.21-7.12 (m, 2H), 6.84 (d, J=6.7 Hz, 1H), 6.47 (s, 2H), 6.32 (s, 1H), 3.85 (s, 2H), 2.43 (s, 3H), 1.81 (s, 3H), 1H not detected.

elemental analysis (C$_{22}$H$_{23}$N$_3$O$_6$S)
Calculated: C, 57.76; H, 5.07; N, 9.18; S, 7.01; O, 20.98.
Found: C, 57.87; H, 5.03; N, 9.24; S, 7.00.

A crude product (100 g) of N-methyl-1-[5-(2-methylphenyl)-1-(pyridin-3-ylsulfonyl)-1H-pyrrol-3-yl]methanamine fumarate and 10% hydrous methanol (900 ml) were added in a four neck flask, and the mixture was dissolved by heating. Insoluble material was filtered off, and washed with 10% hydrous methanol (100 ml). The filtrate was heated again to the refluxing temperature, and stirred for 30 min. After cooling to 40-45° C., the mixture was stirred at the same temperature for 1 hr, at room temperature for 16 hr, and further at 10° C. or below for 1 hr. The precipitated crystals were collected by filtration, and washed with cold 50% hydrous methanol (100 ml). The wet crystals were dried under reduced pressure at 50° C. until a constant weight was reached to give the title compound (72 g, yield 72%).

Example 60

S-[3-cyano-5-(2-methylphenyl)-1H-pyrrol-2-yl]benzenecarbonitrile

[2-(2-Methylphenyl)-2-oxoethyl]propanedinitrile (30 g, 151.3 mmol), thiobenzoic acid (28.5 ml, 243 mmol), triethylamine (2.1 ml, 15.1 mmol) and methanol (300 ml) were mixed, and stirred at about 60° C. for about 4 hr. Water (30 ml) was added at about 36° C., and the mixture was stirred at about 10° C. for about 2 hr. The precipitated crystals were collected by filtration, and washed with a mixture of methanol (72 ml) and water (18 ml). The wet crystals were dried under reduced pressure to give the title compound (44.2 g, yield 91.7%).

Example 61

5-(2-methylphenyl)-1H-pyrrole-3-carbonitrile

Raney-nickel (92 g), water (100 ml), N,N-dimethylacetamide (200 ml) and morpholine (16.4 ml, 187.1 mmol) were mixed. A solution of S—[3-cyano-5-(2-methylphenyl)-1H-pyrrol-2-yl]benzenecarbonitrile (40.0 g, 125.6 mmol) in N,N-dimethylacetamide (200 ml) was added dropwise to the mixture at room temperature. After stirring at about 100° C. for about 3 hr, the mixture was cooled to 30° C. under a nitrogen stream. Raney-nickel was filtered off and ethyl acetate (400 ml) was added to the filtrate. The mixture was washed with 10% aqueous sodium chloride solution (646 ml) and water (580 ml). The organic layer was concentrated under reduced pressure to about a one-fifth amount, ethanol (141 ml) was added, and the mixture was concentrated to about 134 ml. Water (188 ml) was added dropwise at about 80° C., and the mixture was stirred at about 5° C. for about 2 hr. The precipitated crystals were collected by filtration, and washed with a mixture of ethanol (35 ml) and water (47 ml). The wet crystals were dried under reduced pressure to give the title compound (20.9 g, yield 87.1%).

Example 62

5-(2-methylphenyl)-1-(pyridin-3-ylsulfonyl)-1H-pyrrole-3-carbonitrile 5-(2-Methylphenyl)-1H-pyrrole-3-carbonitrile (18.0 g, 98.8 mmol), acetonitrile (67 ml), diisopropylethylamine (23.7 ml, 138 mmol) and 4-N,N-dimethylaminopyridine (2.41 g, 19.7 mmol) were mixed. A solution of 3-pyridinesulfonyl chloride (21.3 g, 118 mmol) in acetonitrile (23 ml) was added dropwise at about 30° C. The mixture was stirred at room temperature for about 3 hr, water (50 ml) was added dropwise, and 0.5 N hydrochloric acid was added dropwise to adjust to pH 4. The precipitated crystals were collected by filtration, washed with a mixture of acetonitrile (11 ml) and water (11 ml). The wet crystals were dried under reduced pressure to give the title compound (25.8 g, yield 80.7%).

Example 63

5-(2-methylphenyl)-1-(pyridin-3-ylsulfonyl)-1H-pyrrole-3-carbaldehyde hydrochloride Under a nitrogen stream, water (60 ml), acetic acid (60 ml), tetrahydrofuran (40 ml), 5-(2-methylphenyl)-1-(pyridin-3-ylsulfonyl)-1H-pyrrole-3-carbonitrile (10.0 g) and Raney-nickel (8 g) were mixed. The mixture was stirred at about 25° C. and internal hydrogen pressure of 0.001-0.008 MPa for about 10 hr. After completion of the reaction, Raney-nickel was filtered off, and washed with a mixture of tetrahydrofuran (3.8 ml), acetic acid (5.6 ml) and water (5.6 ml). To the filtrate and washings were added ethyl acetate (100 ml) and water (100 ml) for partitioning, and the organic layer was concentrated under reduced pressure. Ethyl acetate (50 ml) was added, and the mixture was concentrated under reduced pressure to about 83 g. 4 N hydrochloric acid/ethyl acetate solution (15 ml) was added dropwise at room temperature, and the mixture was stirred at about 50° C. for about 1 hr and at about 10° C. for about 1 hr. The precipitated crystals were collected by filtration, and washed with ethyl acetate (20 ml). The wet crystals were dried under reduced pressure to give the title compound (9.5 g, yield 85%).

Example 64

N-methyl-1-[5-(2-methylphenyl)-1-(pyridin-3-ylsulfonyl)-1H-pyrrol-3-yl]methanamine fumarate 5-(2-Methylphenyl)-1-(pyridin-3-ylsulfonyl)-1H-pyrrole-3-carbaldehyde hydrochloride (20.0 g, 55.1 mmol), ethyl acetate (200 ml) and water (60 ml) were mixed and partitioned. The organic layer was concentrated under reduced pressure. N,N-Dimethylacetamide (60 ml) was added, and a mixture of 40% methylamine methanol solution (14.3 ml) and methanol (120 ml) was added dropwise at about 10° C. A mixture of sodium borohydride (834 mg) and N,N-dimethylacetamide (20 ml) was added dropwise at about −2° C. 4 N Hydrochloric acid was added dropwise at about 3° C. to adjust to around pH 2. Ethyl acetate (240 ml), water (190 ml) and 25% aqueous ammonia (80 ml) were added for partitioning, and the organic layer was washed with 5% brine (110 ml) and water (104 ml). The organic layer was concentrated under reduced pressure, N,N-dimethylformamide (40 ml) and fumaric acid (6.40 g) were added, and the mixture was stirred at about 60° C. for about 3 hr. Ethyl acetate (80 ml) was added at room temperature, and the mixture was stirred at about 5° C. for about 3 hr. The precipitated crystals were collected by filtration, and washed with ethyl acetate (120 ml). The wet crystals were dried under reduced pressure to give the title compound as a crude product (16.7 g, yield 65.7%).

To a crude product (15.0 g) of the title compound was added 20% hydrous methanol (120 ml), and the mixture was dissolved by heating. Activated carbon was added, and the mixture was stirred at about 60° C. for about 10 min. The activated carbon was filtered off, and purified water (200 ml) was added at about 30° C. After stirring for about 2 hr, the mixture was stirred at about 10° C. for about 1 hr. The precipitated crystals were collected by filtration, washed with 50% hydrous methanol (60 ml). The wet crystals were dried under reduced pressure, and dried crystals were pulverized to give the title compound (13.0 g, yield 86.7%).

INDUSTRIAL APPLICABILITY

Sulfonylpyrrole compound (VIII) obtained by the method of the present invention is useful as an acid secretion inhibitor (proton pump inhibitor). In addition, 3-cyanopyrrole compound (III) obtained by the method of the present invention is useful as an intermediate for producing sulfonylpyrrole compound (VIII).

This application is based on patent application No. 2009-042975 filed in Japan, the contents of which are encompassed in full herein.

The invention claimed is:
1. A method of producing a compound represented by the formula

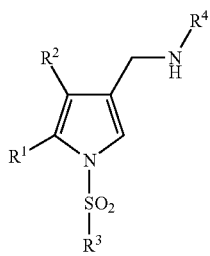

(VIII)

wherein $R^1$ is (1) a $C_{1-6}$ alkyl group or (2) a phenyl group optionally substituted by 1 substituent selected from the group consisting of (i) a halogen atom, (ii) $C_{1-6}$ alkyl optionally substituted by 1 to 5 halogens and (iii) $C_{1-6}$ alkoxy optionally substituted by 1 to 5 halogens, $R^2$ is a hydrogen atom or a $C_{1-6}$ alkyl group, $R^3$ is (i) a $C_{1-6}$ alkyl group, (ii) a phenyl group, or (iii) a pyridyl group, and $R^4$ is a $C_{1-4}$ alkyl group;
or a salt thereof, comprising
(I) reducing a compound represented by the formula

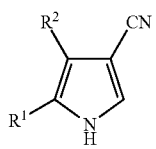

(III)

wherein each symbol is as defined above, or a salt thereof using metal hydride or in the presence of a hydrogen source and a metal catalyst, and hydrolyzing the reduced product in the presence of an acid or a base to give a compound represented by the formula

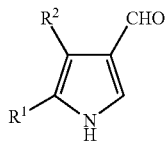

(IV)

wherein each symbol is as defined above, or a salt thereof, wherein the metal hydride is selected from the group consisting of sodium borohydride, lithium borohydride, zinc borohydride, sodium cyanoborohydride, sodium triacetoxyborohydride, lithium cyanoborohydride, diisobutylaluminum hydride, aluminum hydride, lithium aluminum hydride, borane-THF complex, borane-dimethylsulfide, borane-pyridine and catechol borane;

the hydrogen source is selected from the group consisting of hydrogen gas, formic acid, ammonium formate, triethylammonium format, sodium phosphinate and hydrazine;
the metal catalyst is selected from the group consisting of palladium carbon, palladium hydroxide carbon, palladium oxide, Raney-nickel, platinum oxide, platinum carbon and rhodium carbon;
the acid is selected from the group consisting of hydrochloric acid, sulfuric acid, nitric acid, phosphoric acid, boric acid, formic acid, acetic acid, propionic acid, methanesulfonic acid, benzenesulfonic acid, p-toluenesulfonic acid and trifluoromethanesulfonic acid; and
the base is selected from the group consisting of sodium hydroxide, potassium hydroxide, sodium carbonate, potassium carbonate, cesium carbonate and sodium hydrogen carbonate,
(II) reacting the obtained compound with a compound represented by the formula $$R^3—SO_2—X \qquad (V)$$

wherein $R^3$ is as defined above and X is a leaving group, or a salt thereof in the presence of a base, to give a compound represented by the formula

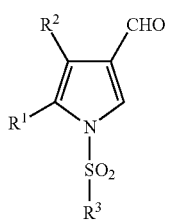

(VI)

wherein each symbol is as defined above, or a salt thereof, wherein the base is selected from the group consisting of sodium hydride, sodium hydroxide, potassium hydroxide, sodium carbonate, potassium carbonate, cesium carbonate, sodium hydrogen carbonate, potassium ethoxide, potassium tert-butoxide, sodium methoxide, sodium ethoxide, pyridine, lutidine, diisopropylethylamine, triethylamine, tripropylamine, tributylamine, cyclohexyldimethylamine, 4-N,N-dimethylaminopyridine, N,N-dimethylaniline, N-methylpiperidine, N-methylpyrrolidine and N-methylmorpholine, and
(III) reacting the obtained compound with a compound represented by the formula $$R^4—NH_2 \qquad (VII)$$

wherein $R^4$ is as defined above, or a salt thereof, in the presence of a reducing agent, wherein the reducing agent is selected from the group consisting of sodium borohydride, sodium cyanoborohydride and sodium triacetoxyborohydride.
2. The method according to claim 1, wherein the compound represented by the formula (VIII) is 1-[5-(2-fluorophenyl)-1-(pyridin-3-ylsulfonyl)-1H-pyrrol-3-yl]-N-methylmethanamine or a salt thereof.

* * * * *

UNITED STATES PATENT AND TRADEMARK OFFICE
CERTIFICATE OF CORRECTION

| | |
|---|---|
| PATENT NO. | : 8,822,694 B2 |
| APPLICATION NO. | : 13/203441 |
| DATED | : September 2, 2014 |
| INVENTOR(S) | : Tomomi Ikemoto et al. |

It is certified that error appears in the above-identified patent and that said Letters Patent is hereby corrected as shown below:

In the Claims:

At column 80, claim number 1, line number 3, replace "format" with --formate--.

Signed and Sealed this
Twenty-first Day of April, 2015

Michelle K. Lee
*Director of the United States Patent and Trademark Office*